United States Patent
Steere et al.

(10) Patent No.: US 10,429,379 B2
(45) Date of Patent: Oct. 1, 2019

(54) AUTOANTIGENS FOR DIAGNOSIS OF RHEUMATOID ARTHRITIS

(71) Applicant: THE GENERAL HOSPITAL CORPORATION, Boston, MA (US)

(72) Inventors: Allen C. Steere, Wellesley, MA (US); Elise E. Drouin, Boston, MA (US)

(73) Assignee: THE GENERAL HOSPITAL CORPORATION, Boston, MA (US)

( * ) Notice: Subject to any disclaimer, the term of this patent is extended or adjusted under 35 U.S.C. 154(b) by 0 days.

(21) Appl. No.: 15/571,734

(22) PCT Filed: May 12, 2016

(86) PCT No.: PCT/US2016/032077
§ 371 (c)(1),
(2) Date: Nov. 3, 2017

(87) PCT Pub. No.: WO2016/183310
PCT Pub. Date: Nov. 17, 2016

(65) Prior Publication Data
US 2018/0156778 A1     Jun. 7, 2018

Related U.S. Application Data

(60) Provisional application No. 62/160,320, filed on May 12, 2015, provisional application No. 62/162,295, filed on May 15, 2015.

(51) Int. Cl.
| | |
|---|---|
| *G01N 33/50* | (2006.01) |
| *G01N 33/564* | (2006.01) |
| *G01N 33/569* | (2006.01) |
| *G01N 33/68* | (2006.01) |

(52) U.S. Cl.
CPC ......... *G01N 33/505* (2013.01); *G01N 33/502* (2013.01); *G01N 33/564* (2013.01); *G01N 33/56972* (2013.01); *G01N 33/6866* (2013.01); *G01N 2333/47* (2013.01); *G01N 2333/4706* (2013.01); *G01N 2333/57* (2013.01); *G01N 2333/914* (2013.01); *G01N 2800/102* (2013.01); *G01N 2800/24* (2013.01)

(58) Field of Classification Search
None
See application file for complete search history.

(56) References Cited

U.S. PATENT DOCUMENTS

| | | | | |
|---|---|---|---|---|
| 4,208,479 | A | * | 6/1980 | Zuk ..................... C07J 41/0016 |
| | | | | 435/7.72 |
| 5,248,595 | A | | 9/1993 | Boyer |
| 2005/0130117 | A1 | | 6/2005 | Davis |
| 2011/0052488 | A1 | | 3/2011 | Dennis et al. |
| 2013/0302329 | A1 | | 11/2013 | Steere |
| 2015/0010631 | A1 | | 1/2015 | Getts |

FOREIGN PATENT DOCUMENTS

| | | |
|---|---|---|
| WO | 2002/048310 A2 | 6/2002 |
| WO | 2004/078098 A2 | 9/2004 |
| WO | 2017214180 A1 | 12/2017 |

OTHER PUBLICATIONS

Campbell (from Monoclonal AntibodyTechnology, Elsevier Sci Pub. 1984, total 16 pages) (Year: 1984).*
Ladd et al. (Cancer Res 2013 vol. 73, 1502-1513) (Year: 2013).*
Pianta et al., "(OP0116) Identification of N-Acetylglucosamine-6-Sulfatase and Filamin a as Novel Targets of Autoimmune T and B Cell Responses in Rheumatoid Arthritis." Annals of the Rheumatic Diseases 74(2):112.2 (2015).
Moen et al., "Immunoglobulin G and A antibody responses to Bacteroides forsythus and Prevotella intermedia in sera and synovial fluids of arthritis patients", Clin Diagn Lab Immunol 10(6) 1043-1050 (2003).
Schellekens et al., "The diagnostic properties of rheumatoid arthritis antibodies recognizing a cyclic citrullinated peptide", Arthritis Rheum 43(1) 155-163 (2000).
Behera et al., "Induction of host matrix metalloproteinases by Borrelia burgdorferi differs in human and murine lyme arthritis", Infect Immun 73(1) 126-134 (2005).
Extended European Search Report dated Oct. 18, 2018 in European Patent Application No. 16793518.8.

* cited by examiner

*Primary Examiner* — Changhwa J Cheu
(74) *Attorney, Agent, or Firm* — David S. Resnick; Shayne Y. Huff; Nixon Peabody LLP

(57) ABSTRACT

Disclosed herein are methods of diagnosing Rheumatoid arthritis in a subject comprising determining whether the subject is immunologically reactive with N-acetylglucosamine-6-sulfatase and/or filamin-A, wherein immunological reactivity of the subject to one or more of N-acetylglucosamine-6-sulfatase or filamin-A, as compared to an appropriate control, indicates the subject has rheumatoid arthritis. Examples of specific assays and kits for use with the methods are also disclosed.

12 Claims, 26 Drawing Sheets
Specification includes a Sequence Listing.

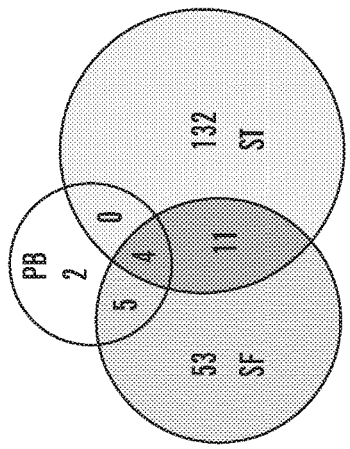
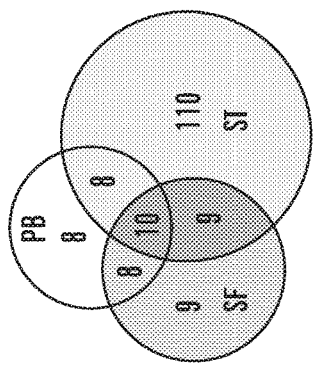
FIG. 1A

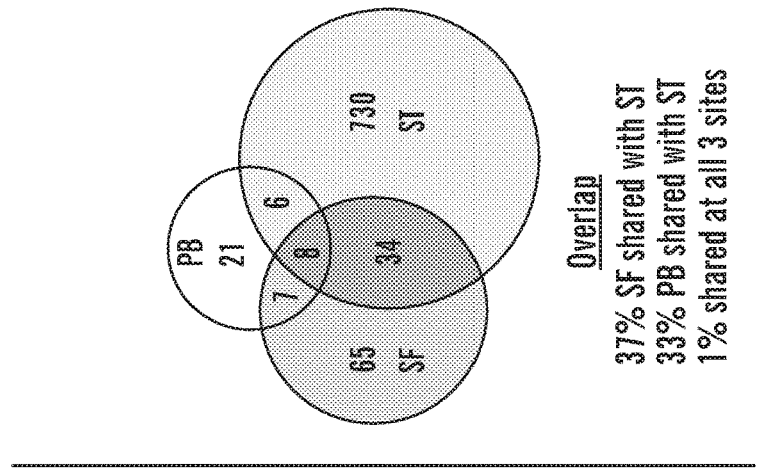
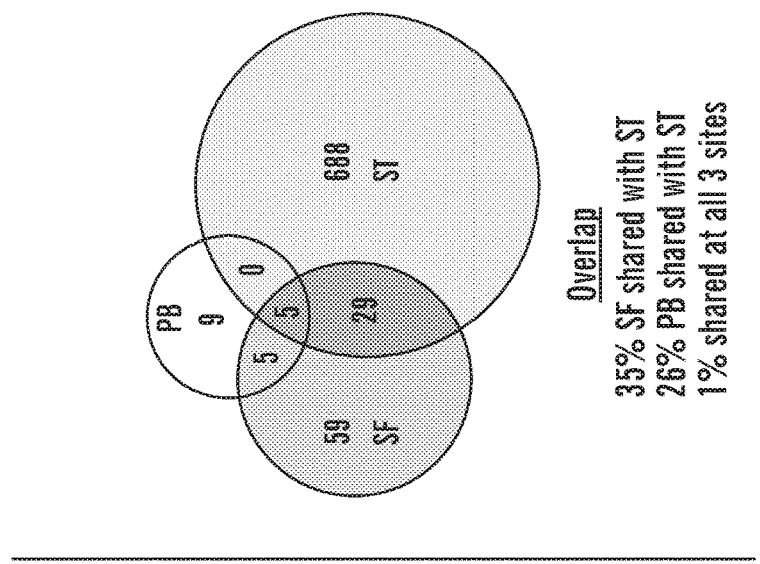
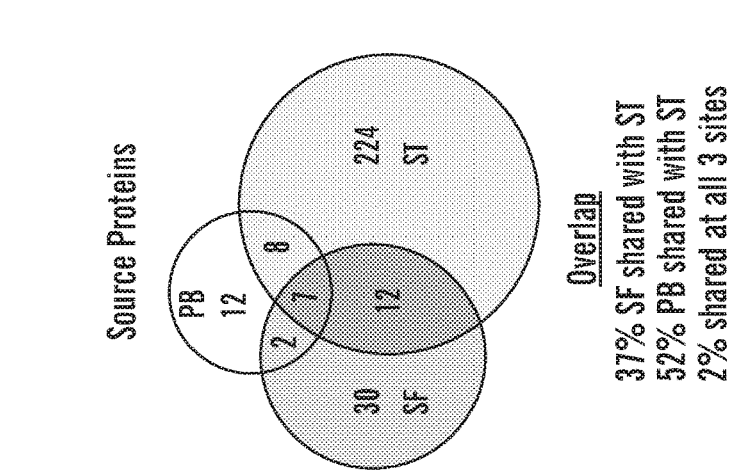
FIG. 1D

FIG. 4

| Case Patient | | RA2 |
|---|---|---|
| Gender | | F |
| Age (years) | | 37 |
| Arthritis Duration (years) | | 3 |
| Rheumatoid Factor | | pos |
| ACPA* | | pos |
| HLA-DR genotype | | 0101/0401 |
| Synovial tissue | # HLA-DR peptides | 89 |
| | # source Proteins | 86 |
| | # reactive peptides | 1 (GNS) |
| Synovial fluid | # HLA-DR peptides | 19 |
| | # source proteins | 13 |
| | # reactive peptides | 0 |
| Peripheral blood | # HLA-DR peptides | 15 |
| | # source proteins | 11 |
| | # reactive peptides | 1 (FLNA) |

*anti-citrullinated protein antibodies; # Number of; GNS, N-acetylglucosamine-6-sulfatase; FLNA, filamin A.

FIG. 9

1   MRLLPLAPGR LRRGSPRHLP SCSPALLLLV LGGCLGVFGV AAGTRRPNVV LLLTDDQDEV
61  LGGMTPLKKT KALIGEMGMT FSSAYVPSAL CCPSRASILT GKYPHNHHVV NNTLEGNCSS
121 KSWQKIQEPN TFPAILRSMC GYQTFFAGKY LNEYGAPDAG GLEHVPLGWS YWYALEKNSK
181 YYNYTLSING KARKHGENYS VDYLTDVLAN VSLDFLDYKS NFEPFFMMIA TPAPHSPWTA
241 APQYQKAFQN VFAPRNKNFN IHGTNKHWLI RQAKTPMTNS SIQFLDNAFR KRWQTLLSVD
301 DLVEKLVKRL EFTGELNNTY IFYTSDNGYH TGQFSLPIDK RQLYEFDIKV PLLVRGPGIK
361 PNQTSKMLVA NIDLGPTILD IAGYDLNKTQ MDGMSLLPIL RGASNLTWRS DVLVEYQGEG
421 RNVTDPTCPS LSPGVSQCFP DCVCEDAYNN TYACVRTMSA LWNLQYCEFD DQEVFVEVYN
481 LTADPDQITN IAKTIDPELL GKMNYRLMML QSCSGPTCRT PGVFDPGYRF DPRLMFSNRG
541 SVRTRRFSKH LL

FIG. 10

```
   1 MSSSHSRAGQ SAAGAAPGGG VDTRDAEMPA TEKDLAEDAP WKKIQQNTFT RWCNEHLKCV
  61 SKRIANLQTD LSDGLRLIAL LEVLSQKKMH RKHNQRPTFR QMQLENVSVA LEFLDRESIK
 121 LVSIDSKAIV DGNLKLILGL IWTLILHYSI SMPMWDEEED EEAKKQTPKQ RLLGWIQNKL
 181 PQLPITNFSR DWQSGRALGA LVDSCAPGLC PDWDSWDASK PVTNAREAMQ QADDWLGIPQ
 241 VITPEEIVDP NVDEHSVMTY LSQFPKAKLK PGAPLRPKLN PKKARAYGPG IEPTGNMVKK
 301 RAEFTVETRS AGQGEVLVYV EDPAGHQEEA KVTANNDKNR TFSVWYVPEV TGTHKVTVLF
 361 AGQHIAKSPF EVYVDKSQGD ASKVTAQGPG LEPSGNIANK TTYFEIFTAG AGTGEVEVVI
 421 QDPMGQKGTV EPQLEARGDS TYRCSYQPTM EGVHTVHVTF AGVPIPRSPY TVTVGQACNP
 481 SACRAVGRGL QPKGVRVKET ADFKVYTKGA GSGELKVTVK GPKGEERVKQ KDLGDGVYGF
 541 EYYPMVPGTY IVTITWGGQN IGRSPFEVKV GTECGNQKVR AWGPGLEGGV VGKSADFVVE
 601 AIGDDVGTLG FSVEGPSQAK IECDDKGDGS CDVRYWPQEA GEYAVHVLCN SEDIRLSPFM
 661 ADIRDAPQDF HPDRVKARGP GLEKTGVAVN KPAEFTVDAK HGGKAPLRVQ VQDNEGCPVE
 721 ALVKDNGNGT YSCSYVPRKP VKHTAMVSWG GVSIPNSPFR VNVGAGSHPN KVKVYGPGVA
 781 KTGLKAHEPT YFTVDCAEAG QGDVSIGIKC APGVVGPAEA DIDFDIIRND NDTFTVKYTP
 841 RGAGSYTIMV LFADQATPTS PIRVKVEPSH DASKVKAEGP GLSRTGVELG KPTHFTVNAK
 901 AAGKGKLDVQ FSGLTKGDAV RDVDIIDHHD NTYTVKYTPV QQGPVGVNVT YGGDPIPKSP
 961 FSVAVSPSLD LSKIKVSGLG EKVDVGKDQE FTVKSKGAGG QGKVASKIVG PSGAAVPCKV
1021 EPGLGADNSV VRFLPREEGP YEVEVTYDGV PVPGSPFPLE AVAPTKPSKV KAFGPGLQGG
1081 SAGSPARFTI DTKGAGTGGL GLTVEGPCEA QLECLDNGDG TCSVSYVPTE PGDYNINILF
1141 ADTHIPGSPF KAHVVPCFDA SKVKCSGPGL ERATAGEVGQ FQVDCSSAGS AELTIEICSE
1201 AGLPAEVYIQ DHGDGTHTIT YIPLCPGAYT VTIKYGGQPV PNFPSKLQVE PAVDTSGVQC
1261 YGPGIEGQGV FREATTEFSV DARALIQTGG PHVKARVANP SGNLTETYVQ DRGDGMYKVE
1321 YTPYEEGLHS VDVTYDGSPV PSSPFQVPVT EGCDPSRVRV HGPGIQSGTT NKPNKFTVET
1381 RGAGTGGLGL AVEGPSEAKM SCMDNKDGSC SVEYIPYEAG TYSLNVTYGG HQVPGSPFKV
```

FIG. 10 cont'd

```
1441 PVHDVTDASK VKCSGPGLSP GMVRANLPQS FQVDTSKAGV APLQVKVQGP KGLVEPVDVV
1501 DNADGTQTVN YVPSREGPYS ISVLYGDEEV PRSPFKVKVL PTHDASKVKA SGPGLNTTGV
1561 PASLPVEFTI DAKDAGEGLL AVQITDPEGK PKKTHIQDNH DGTYTVAYVP DVTGRYTILI
1621 KYGGDEIPFS PYRVRAVPTG DASKCTVTVS IGGHGLGAGI GPTIQIGEET VITVDTKAAG
1681 KGKVTCTVCT PDGSEVDVDV VENEDGTFDI FYTAPQPGKY VICVRFGGEH VPNSPFQVTA
1741 LAGDQPSVQP PLRSQQLAPQ YTYAQGGQQT WAPERPLVGV NGLDVTSLRP FDLVIPFTIK
1801 KGEITGEVRM PSGKVAQPTI TDNKDGTVTV RYAPSEAGLH EMDIRYDNMH IPGSPLQFYV
1861 DYVNCGHVTA YGPGLTHGVV NKPATFTVNT KDAGEGGLSL AIEGPSKAEI SCTDNQDGTC
1921 SVSYLPVLPG DYSILVKYNE QHVPGSPFTA RVTGDDSMRM SHLKVGSAAD IPINISETDL
1981 SLLTATVVPP SGREEPCLLK RLRNGHVGIS FVPKETGEHL VHVKKNGQHV ASSPIPVVIS
2041 QSEIGDASRV RVSGQGLHEG HTFEPAEFII DTRDAGYGGL SLSIEGPSKV DINTEDLEDG
2101 TCRVTYCPTE PGNYIINIKF ADQHVPGSPF SVKVTGEGRV KESITRRRRA PSVANVGSHC
2161 DLSLKIPEIS IQDMTAQVTS PSGKTHEAEI VEGENHTYCI RFVPAEMGTH TVSVKYKGQH
2221 VPGSPFQFTV GPLGEGGAHK VRAGGPGLER AEAGVPAEFS IWTREAGAGG LAIAVEGPSK
2281 AEISFEDRKD GSCGVAYVVQ EPGDYEVSVK FNEEHIPDSP FVVPVASPSG DARRLTVSSL
2341 QESGLKVNQP ASFAVSLNGA KGAIDAKVHS PSGALEECYV TEIDQDKYAV RFIPRENGVY
2401 LIDVKFNGTH IPGSPFKIRV GEPGHGGDPG LVSAYGAGLE GGVTGNPAEF VVNTSNAGAG
2461 ALSVTIDGPS KVKMDCQECP EGYRVTYTPM APGSYLISIK YGGPYHIGGS PFKAKVTGPR
2521 LVSNHSLHET SSVFVDSLTK ATCAPQHGAP GPGPADASKV VAKGLGLSKA YVGQKSSFTV
2581 DCSKAGNNML LVGVHGPRTP CEEILVKHVG SRLYSVSYLL KDKGEYTLVV KWGDEHIPGS
2641 PYRVVVP
```

AUTOANTIGENS FOR DIAGNOSIS OF RHEUMATOID ARTHRITIS

CROSS-REFERENCE TO RELATED APPLICATION

This application is a 35 U.S.C. § 371 National Phase Entry Application of International Application No. PCT/US2016/032077, filed May 12, 2016 which claims benefit under 35 U.S.C. § 119(e) of U.S. Provisional Application Nos. 62/160,320, filed May 12, 2015 and 62/162,295 filed May 15, 2015, the contents of each of which are incorporated herein by reference in their entireties.

GOVERNMENTAL SUPPORT

This invention was made with government support under Grant Nos. P41 GM104603, S10 RR020946, S10 OD010724 and R01 AI110175 awarded by the National Institutes of Health (NIH) and Grant No. HHSN268201000031C awarded by the NIH National Heart, Lung, and Blood Institute (NHLBI). The government has certain rights in the invention.

TECHNICAL FIELD

The present invention relates to the field of diagnostics using humoral and cellular autoimmune responses to disease-related autoantigens. In particular, it relates to autoantigenic biomarkers for rheumatoid arthritis.

BACKGROUND

Rheumatoid arthritis (RA) is a chronic autoimmune disease of unknown cause that affects primary joints. Human leukocyte antigen-antigen D related (HLA-DR) molecules play a central role in autoimmune diseases, as first reported by McDevitt in 1974, (1) HLA-DR molecules are highly expressed in synovial tissue (ST), the target of the immune response in chronic inflammatory forms of arthritis, including rheumatoid arthritis (RA) and Lyme arthritis (LA) (2, 3). The greatest known genetic risk factors for these diseases are certain HLA-DR alleles (4). HLA-DR molecules present foreign or self-peptides to CD4+ T cells, leading to their activation (5). After activation, T cells can supply the necessary help to B cells to produce sustained, high-titer antibodies against the same antigen. In RA, 10 HLA-DR alleles, including the HLA-DRB1*0101 and 0401 alleles (6, 7) convey the greatest risk. These alleles code for a similar sequence of amino acids, called the RA shared epitope, which line the P4 pocket of the HLA-DR molecule. Anti-citrullinated protein antibodies (ACPA), which are specific for RA, are significantly more frequent in patients who have the shared epitope (8-13).

In both RA and LA, synovial tissue shows marked synovial hypertrophy, vascular proliferation, mononuclear cell infiltration, and intense expression of HLA-DR molecules on synoviocytes and infiltrating cells (2, 3). The tissue is bathed in synovial fluid (SF), which contains a rich mixture of inflammatory cells, including large numbers of dendritic cells and macrophages; the latter also have increased expression of HLA-DR molecules (28, 29). However, the repertoire of specific self-peptides presented by HLA-DR molecules in synovial tissues in RA is unknown. Accordingly there is an unmet need of identifying autoantigens presented by HLA-DR and pathogenic T-cell epitopes in synovial tissues, synovial fluid as well as peripheral blood mononuclear cells of RA patients.

SUMMARY

Aspects of the invention relate to a method of diagnosing rheumatoid arthritis in a subject comprising determining whether the subject is immunologically reactive with one or more of filamin-A and N-acetylglucosamine-6-sulfatase, wherein immunological reactivity of the subject to one or more of filamin-A and N-acetylglucosamine-6-sulfatase, as compared to an appropriate control, indicates the subject has rheumatoid arthritis.

In one embodiment, the determining is by evaluating a biological sample obtained from the subject for immunological reactivity with the one or more of filamin-A and N-acetylglucosamine-6-sulfatase.

In one embodiment of the foregoing aspects, determining immunological reactivity is by detecting the presence of T cells reactive to one or more of filamin-A and N-acetylglucosamine-6-sulfatase, comprising the steps: a) stimulating peripheral blood mononuclear cells (PBMC) of the subject or the synovial fluid mononuclear cells (SFMC) of the subject in vitro with one or more of filamin-A and N-acetylglucosamine-6-sulfatase, whole protein or polypeptide fragments; b) measuring T cell proliferation in vitro or secretion of IFN-γ into cell culture supernatants; and c) identifying the subject as having T cells reactive to one or more of filamin-A and N-acetylglucosamine-6-sulfatase when T cell proliferation or secretion of IFN-γ is measured as significantly increased over that of an appropriate control.

In one embodiment, step b) is measuring T cell proliferation in vitro, and the subject is identified as having T cell reactive to one or more of filamin-A and N-acetylglucosamine-6-sulfatase when T cell proliferation is measured as significantly increased over that of an appropriate control. In one embodiment, step b) is measuring T cell secretion of IFN-γ into cell culture supernatants, and the subject is identified as having T cell reactive to one or more of filamin-A and N-acetylglucosamine-6-sulfatase when secretion of IFN-γ is measured as significantly increased over that of an appropriate control.

In one embodiment, determining immunological reactivity comprises determining if the subject has a B-cell response to one or more of filamin-A and N-acetylglucosamine-6-sulfatase resulting in the production of autoantibodies that specifically recognize the one or more filamin-A and N-acetylglucosamine-6-sulfatase, by contacting the sample with filamin-A protein or a polypeptide fragment thereof, and/or N-acetylglucosamine-6-sulfatase protein or a polypeptide fragment thereof, under conditions that allow an immunocomplex of the antibody and the filamin-A or N-acetylglucosamine-6-sulfatase form, and detecting the presence or absence of an immunocomplex, wherein the presence of an immunocomplex indicates the subject presents a B-cell response to filamin-A and/or N-acetylglucosamine-6-sulfatase and wherein the absence of an immunocomplex indicates the subject fails to present a B-cell response to filamin-A and/or N-acetylglucosamine-6-sulfatase.

In one embodiment, the assay is an enzyme-linked immunosorbent assay (ELISA), agglutination test, direct immunofluorescence assay, indirect immunofluorescence assay, or an immunoblot assay.

In one embodiment of the foregoing aspects, the polypeptide fragment of filamin-A comprises the amino acid sequence NPAEFVVNTSNAGAG (SEQ ID NO: 1) or an antigenic portion thereof.

In one embodiment, the polypeptide fragment of N-acetylglucosamine-6-sulfatase comprises the amino acid sequence of FEPFFMMIATPAPH (SEQ ID NO: 2) or an antigenic portion thereof.

In one embodiment of the foregoing aspects, the subject has been or is further tested for one or more of rheumatoid factor, anti-citrullinated protein antibodies (ACPA), and one or more HLA-DR alleles. In one embodiment, the HLA-DR allele is HLA-DRB1*0101 and/or HLA-DRB1*0401. In one embodiment, the subject is at risk for, or is suspected of having, rheumatoid arthritis.

In one embodiment of the various methods described herein, the method further comprises the step of treating the subject with one or more of a nonsteroidal anti-inflammatory drug (NSAIDs), a steroid, a disease modifying anti-rheumatic drug (DMARD), and a biologic.

In one aspect described herein is a kit comprising one or more potential antigen and/or potential epitope of filamin-A and/or N-acetylglucosamine-6-sulfatase, and reagents for conducting an assay for detecting the presence of an antibody in a sample that binds to the one or more potential antigen and/or potential epitope of the filamin-A and N-acetylglucosamine-6-sulfatase.

In one embodiment, the potential antigen and/or potential epitope of filamin-A comprises the amino acid sequence NPAEFVVNTSNAGAG (SEQ ID NO: 1) or an antigenic portion thereof in one embodiment, the potential antigen and/or potential epitope of N-acetylglucosamine-6-sulfatase comprises the amino acid sequence FEPFFMMIATPAPH (SEQ ID NO: 2) or an antigenic portion thereof.

In one embodiment of the foregoing aspects, the assay is an enzyme-linked immunosorbent assay (ELISA). In one embodiment, the assay is a western blot.

Another aspect of the invention relates to a kit or method disclosed above for use in identifying a subject with rheumatoid arthritis.

DEFINITIONS

Unless stated otherwise, or implicit from context, the following terms and phrases include the meanings provided below. Unless explicitly stated otherwise, or apparent from context, the terms and phrases below do not exclude the meaning that the term or phrase has acquired in the art to which it pertains. The definitions are provided to aid in describing particular embodiments, and are not intended to limit the claimed invention, because the scope of the invention is limited only by the claims. Further, unless otherwise required by context, singular terms shall include pluralities and plural terms shall include the singular.

As used herein, the terms "diagnose" or "diagnosis" or "diagnosing" refers to determining the nature or the identity of a condition or disease or disorder, detecting and/or classifying the disease and/or disorder in a subject. A diagnosis may be accompanied by a determination as to the severity of the disease. The term also encompasses assessing or evaluating the disease status (progression, regression, stabilization, response to treatment, etc.) in a patient known to have the disease). Diagnosis as it relates to the present invention, relates to the diagnosis of chronic inflammatory arthritis e.g., Rheumatoid arthritis. The diagnosis can be differential diagnosis. As used herein, "differential diagnosis" refers to determination of which two or more diseases with similar symptoms (e.g., RA, osteoarthritis, systemic lupus erythematosus, Lyme arthritis, reactive arthritis, psoriatic arthritis, ankylosing spondylitis) is the one from which a patient is suffering from based on an analysis of clinical data such as for example results obtained from methods described herein.

As used herein, the term "biological sample" refers to a sample obtained for evaluation in vitro. The biological sample can be any sample that is expected to contain antibodies and/or immune cells. The sample can be taken from a part of the body that is specifically affected by the disorder, such as taken specifically from a site of inflammation or pathology in the subject (e.g., synnovial fluid, synovial tissue, synovial fluid mononuclear cells (SFMC), spinal fluid, etc.) or can be a more systemic sample (e.g., peripheral blood, peripheral blood mononuclear cells (PBMC), whole blood or whole blood pre-treated with an anticoagulant such as heparin, ethylenediamine tetraacetic acid, plasma or serum). Sample can be pretreated prior to use, such as preparing plasma from blood, diluting viscous liquids, or the like; methods of treatment can also involve separation, filtration, distillation, concentration, inactivation of interfering components, and the addition of reagents.

As used herein, "immunologically reactive" or "immunoreactive" is defined as the capability of the molecule (e.g., whole protein or polypeptide fragments thereof) of the present invention to induce a specific immune response (e.g. T cell reactivity, B cell response) in appropriate subjects or cells and to bind with specific antibodies. The immunological reactivity can be assayed in a biological sample comprising immunological cells and/or antibodies obtained from a subject by methods described herein.

As used herein "autoantigen/self-antigen" is any substance normally found within a subject which, in an abnormal situation, is no longer recognized as part of the subject itself by the lymphocytes or antibodies of that subject, and is therefore attacked by the immune system as though it were a foreign substance. An autoantigen can be a naturally occurring molecule such as a protein (e.g., GNS, filamin A) normally produced and used by the subject itself, eliciting an immune response possibly leading to an autoimmune disease (e.g. RA) in the subject.

The term "antibody," as used herein, refers to an immunoglobulin molecule which is able to "specifically recognize" and/or "specifically bind" to a specific epitope on an antigen. Antibodies can be intact immunoglobulins derived from natural sources or from recombinant sources and can be immunoreactive portions of intact immunoglobulins. Antibodies are typically immunoglobulin molecules.

As used herein, "autoantibody" means an antibody produced by the immune system of a subject that is directed to, and specifically binds to an "autoantigen/self-antigen" or an "antigenic epitope" thereof.

As used herein, the term "epitope" refers to that portion of any molecule capable of being recognized by, and bound by, a T cell or an antibody (the corresponding antibody binding region may be referred to as a paratope), and/or eliciting an immune response. In general, epitopes consist of chemically active surface groupings of molecules, e.g., amino acids, and have specific three-dimensional structural characteristics as well as specific charge characteristics. As used herein, "immunogenic epitope", as determined by any method known in the art, is defined as a portion of a polypeptide that causes an immune response in a subject. As used herein, "antigenic epitope", as determined by any methods well known in the art, in that a given antibody or T cell receptor specifically recognizes and specifically binds to a given antigen. It can be, and is defined as a portion of a protein (e.g. GNS, filamin A). As used herein, "antigenic portion" refers to the portion of GNS and filamin A that includes the antigenic epitopes.

"Specifically bind" and/or "specifically recognize" as used herein, refers to the higher affinity of a binding molecule for a target molecule compared to the binding molecule's affinity for non-target molecules. A binding molecule that specifically binds a target molecule does not substantially recognize or bind non-target molecules. e.g., an antibody "specifically binds" and/or "specifically recognize" another molecule, meaning that this interaction is dependent on the presence of the binding specificity of the molecule structure, e.g., an antigenic epitope. For example, an antibody that specifically binds to the antigenic epitope of protein molecules such as GNS, filamin A, and/or polypeptide fragments thereof, instead of indiscriminately binding to cause non-specific binding and/or background binding. As used herein, "non-specific binding" and "background binding" refers to the interaction that does not depend on the presence of specific structure (e.g., a specific antigenic epitopes).

As used herein, an "immunoassay" refers to any binding assay that uses an antibody capable of binding specifically to a target molecule to detect and quantify the target molecule.

As used herein, an "appropriate control" refers to one or more biological samples obtained from a subject not afflicted with a disease or disorder that features abnormal level of the molecule and measurement of the molecule therein. An example of an appropriate control can be biological sample from a subject not afflicted from RA. As it relates to the present invention, an appropriate negative control sample would not be positive for T cell reactivity to and/or show presence of autoantibodies to GNS, filamin A and/or polypeptide fragments thereof when tested using the methods described herein.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also be related to a distemper, ailing, ailment, malady, disorder, sickness, illness, complaint, or affectation.

As used herein, the terms "treat," "treatment," "treating," or "amelioration" refer to therapeutic treatments, wherein the object is to reverse, alleviate, ameliorate, inhibit, slow down or stop the progression or severity of chronic inflammatory arthritis, (e.g., Rheumatoid arthritis), an associated condition and/or a symptom thereof. The term "treating" includes reducing or alleviating at least one adverse effect or symptom of RA. Treatment is generally "effective" if one or more symptoms or clinical markers (e.g. antibodies to one or more of GNS, filamin A or cyclic citrullinated peptide (anti-CCP) and/or rheumatoid factors) are reduced. Alternatively, or in addition, treatment is "effective" if the progression of a disease is reduced or halted. That is, "treatment" includes not just the improvement of symptoms or markers, but also a cessation of, or at least slowing of, progress or worsening of symptoms compared to what would be expected in the absence of treatment. Accordingly in case of chronic inflammatory arthritis such as RA, "effective treatment" can for example reduce inflammation, swelling and joint pain, bone deformity and/or result in reduction in T or B cell reactivity to GNS, filamin A and/or polypeptides thereof and/or reduction in autoantibodies to GNS, filamin A and/or polypeptides thereof compared to that observed pretreatment, as determined by methods described herein. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality. For example, treatment is considered effective if the condition is stabilized. The term "treatment" of a disease also includes providing relief from the symptoms or side-effects of the disease (including palliative treatment).

As used herein, a "subject", "patient", "individual" and like terms are used interchangeably and refers to a vertebrate, preferably a mammal, more preferably a primate, still more preferably a human. Mammals include, without limitation, humans, primates, rodents, wild or domesticated animals, including feral animals, farm animals, sport animals, and pets. Primates include, for example, chimpanzees, cynomologous monkeys, spider monkeys, and macaques, e.g., Rhesus. Rodents include, for example, mice, rats, woodchucks, ferrets, rabbits and hamsters. Domestic and game animals include, for example, cows, horses, pigs, deer, bison, buffalo, feline species, e.g., domestic cat, and canine species, e.g., dog, fox, wolf, avian species, e.g., chicken, emu, ostrich, and fish, e.g., trout, catfish and salmon. The terms, "individual," "patient" and "subject" are used interchangeably herein. In one embodiment the subject is male. In another embodiment, the subject is female.

Preferably, the subject is a mammal. The mammal can be a human, non-human primate, mouse, rat, dog, cat, horse, or cow, but is not limited to these examples. Mammals other than humans can be advantageously used as subjects that represent animal models of conditions or disorders associated with RA. Such models are known in the art and are described in (71). In addition, the compositions and methods described herein can be used to diagnose domesticated animals and/or pets.

A subject can be one who has been previously diagnosed with or identified as suffering from or under medical supervision for a chronic inflammatory and/or autoimmune disease (e.g., RA). A subject can be one who is diagnosed and currently being treated for, or seeking treatment, monitoring, adjustment or modification of an existing therapeutic treatment, or is at a risk of developing RA, e.g., due to family history, carrying alleles or genotype associated with RA (e.g. HLA-DRB1*0101 and DRB1*0401, HLA-DRB1*0405 and DRB1*0408). The subject can exhibit one or more symptoms of autoimmune disease (e.g., RA) (e.g. swollen joints, joint pains). The subject may have tested positive with other assays for RA associated factor. Such factors include rheumatoid factor, anti-citrullinated protein antibodies (ACPA), one or more of HLA-DR alleles associated with RA, or other autoantigens. The subject may lack one or more symptoms of autoimmune disease. The subject may be identified as testing negative for other RA associated factors (rheumatoid factor, anti-citrullinated protein antibodies (ACPA), one or more of HLA-DR alleles, and other autoantigens).

As used herein, the terms "protein", "peptide" and "polypeptide" are used interchangeably to designate a series of amino acid residues connected to each other by bonds between the alpha-amino and carboxy groups of adjacent residues. The terms "protein", "peptide" and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein", "peptide" and "polypeptide" are used interchangeably herein when referring to a gene product and fragments thereof.

The term "statistically significant" or "significantly" refers to statistical significance and generally means a difference of two standard deviations (2SD) or more.

Definitions of common terms in cell biology and molecular biology can be found in "The Merck Manual of Diagnosis and Therapy", 19th Edition, published by Merck Research Laboratories, 2006 (ISBN 0-911910-19-0); Robert S. Porter et al. (eds.), The Encyclopedia of Molecular Biology, published by Blackwell Science Ltd., 1994 (ISBN 0-632-02182-9); Immunology by Werner Luttmann, published by Elsevier, 2006. Definitions of common terms in molecular biology can also be found in Benjamin Lewin, Genes X, published by Jones & Bartlett Publishing, 2009 (ISBN-10: 0763766321); Kendrew et al. (eds.), Molecular Biology and Biotechnology: a Comprehensive Desk Reference, published by VCH Publishers, Inc., 1995 (ISBN 1-56081-569-8) and Current Protocols in Protein Sciences 2009, Wiley Intersciences, Coligan et al., eds.

Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

Although methods and materials similar or equivalent to those described herein can be used in the practice or testing of this disclosure, suitable methods and materials are described below. The abbreviation, "e.g.," is derived from the Latin exempli gratia, and is used herein to indicate a non-limiting example. Thus, the abbreviation "e.g.," is synonymous with the term "for example."

As used in this specification and appended claims, the singular forms "a," "an", and "the" include plural references unless the context clearly dictates otherwise. Thus for example, reference to "the method" included one or more methods, and/or steps of the type described herein and/or which will become apparent to those persons skilled in the art upon reading this disclosure and so forth.

In this application and the claims, the use of the singular includes the plural unless specifically stated otherwise. In addition, use of "or" means "and/or" unless stated otherwise. Moreover, the use of the term "including", as well as other forms, such as "includes" and "included", is not limiting. Also, terms such as "element" or "component" encompass both elements and components comprising one unit and elements and components that comprise more than one unit unless specifically stated otherwise.

BRIEF DESCRIPTION OF THE DRAWINGS

FIGS. 1A-1D show degree of overlap in HLA-DR-presented peptides and their source proteins identified in the synovial tissue (ST), synovial fluid mononuclear cells (SFMC) or peripheral blood mononuclear cells (PBMC) of RA or Lyme arthritis (LA) patients. The Venn diagrams depict the number of shared peptides or source proteins identified in the ST, SFMC or PBMC of individual RA or LA patients or in the entire RA and/or LA cohort. (FIG. 1A) Shared peptides or (FIG. 1B) shared source proteins identified in patients RA2 or LA5. (FIG. 1C) Shared peptides or (FIG. 1D) shared source proteins identified in the RA, LA, or RA and LA cohorts. All peptide comparisons were based upon consensus-matched, non-redundant identified peptides using in-house generated software. The consensus on source proteins matched between cohorts was assembled by matching the source protein accession numbers using a Microsoft Access query.

(FIG. 2A) CID MS2 spectrum, recorded using the ion trap on the LTQ-Orbitrap XL MS for analysis of the mixture of MHC class II-presented peptides recovered from the synovial tissue of patient RA3. The spectrum was assigned to a modified form of the peptide $^{27}$VNDTQFVRFDSDAASPRG$^{44}$ (SEQ ID NO: 5) derived from the source protein B6V6K3 MHC class I antigen (fragment). No sequence-defining fragment ions were observed between the second and eighth residues; nevertheless, the post-translational modification of arginine conversion to citrulline at R8 was assigned by two protein database search programs. (FIG. 2B) HCD MS2 spectrum of the same component, recorded with the Q Exactive plus MS, allowed unambiguous assignment of asparagine deamidation at N2 as the post-translational modification on the peptide sequence. Note: ° loss of H2O; * loss of NH3.

(FIG. 3A) $^{340}$LGRFERMLAAQGVDPG$^{355}$ (SEQ ID NO: 6) from endothelial cell growth factor was identified by OMSSA from LA1 ST (22). (FIG. 3B) $^{655}$IEGNLIFDPNNYLPK$^{669}$ (SEQ ID NO: 7) from apolipoprotein B-100 was consistently identified by Mascot and X!Tandem from LA5 ST (23). (FIG. 3C) $^{208}$GTNLFLVAAHELGHS$^{222}$ (SEQ ID NO: 8) from matrix metalloproteinase-10 (stromelysin 2) was identified by Mascot from LA4 ST (24) (FIG. 3D) $^{285}$DKVLIRIMVSRSEVD$^{299}$ (SEQ ID NO: 9) from annexin A2 was consistently identified by Mascot, OMSSA, and X!Tandem from RA1 ST (25). (FIG. 3E) $^{2446}$NPAEFVVNTSNAGAG$^{2460}$ (SEQ ID NO: 1) from filamin A was consistently identified by Mascot, OMSSA, and X!Tandem from RA2 ST (the same peptide was also identified consistently by Mascot, OMSSA, and X!Tandem from RA2 PB) (26) and (FIG. 3F) $^{222}$FEPFFMMIATPAPH$^{235}$ (SEQ ID NO: 2) from N-acetylglucosamine-6-sulfatase was consistently identified by Mascot, OMSSA, and X!Tandem from RA2 ST (26) Note: ° loss of H2O; * loss of NH3.

FIG. 4 shows clinical characteristics, number of HLA-DR-presented peptides and source proteins identified from the case patient RA2. 1 of 89 HLA-DR presented peptides identified from synovial tissue and 1 of 15 HLA-DR presented peptides identified from her peripheral blood of patient induced the patient's PBMC to secrete IFNγ. These reactive peptides were derived from the proteins GNS and filamin A respectively.

(FIG. 5A) PBMC from healthy control (HC) subjects or RA patients were tested for T cell autoreactivity against the filamin A peptide, plus three additional filamin A peptides predicted to be promiscuous HLA-DR binders (promiscuous T cell epitopes). Each assay also included a positive control (PHA) and a negative control (no peptides), T cell reactivity was measured using an IFNγ enzyme linked immunospot (ELISpot) assay. The spot forming units (SFU) per $10^5$ were calculated. A positive response was defined as 3 standard deviations above the mean SFU/$10^6$ cells of healthy control subjects (area above the gray shaded region). (FIG. 5B) The levels of IgG anti-filamin A in the sera of HC subjects, RA patients or Lyme arthritis (LA) patients were measured by enzyme-linked immunosorbent assay (ELISA). Plates were coated with recombinant human Filamin A and the wells were incubated with serum samples from each test subject. As controls, wells were also incubated with recombinant IgG anti-filamin A (positive control) or buffer (negative control). Bound IgG anti-filamin antibodies were detected using horseradish peroxidase-conjugated goat anti-human IgG followed by TMB substrate. The shaded gray area corresponds to 3 standard deviations above the mean of HC subjects. Percentage of positive response for each patient group are as shown below the graph. P values were calculated using an inpaired t-test. Horizontal line indicates the mean of each dataset. The method used to identify this disease associated autoantigen is described in references (22, 30).

(FIG. 6A) PBMC from healthy control (HC) subjects or RA patients were tested for T cell autoreactivity against the GNS peptide identified from the synovial tissue of patient with RA, plus three additional GNS peptides predicted to be promiscuous HLA-DR binders (promiscuous T cell epitopes). Each assay also included a positive control (PHA) and a negative control (no peptides), T cell reactivity was measured using an IFNγ enzyme linked immunospot (ELISpot) assay. The spot forming units (SFU) per $10^5$ were calculated. A positive response was defined as 3 standard deviations above the mean SFU/$10^6$ cells of healthy control subjects (area above the gray shaded region). (FIG. 6B) The levels of IgG anti-GNS in the sera of HC subjects, RA patients or Lyme arthritis (LA) patients were measured by enzyme-linked immunosorbent assay (ELISA). Plates were coated with recombinant human GNS and the wells were incubated with serum samples from each test subject. As controls, wells were also incubated with recombinant IgG anti-GNS (positive control) or buffer (negative control). Bound IgG anti-GNS antibodies were detected using horseradish peroxidase-conjugated goat anti-human IgG followed by TMB substrate. The shaded gray area corresponds to 3 standard deviations above the mean of HC subjects. Percentage of positive response for each patient group are as shown below the graph. P values were calculated using an inpaired t-test. Horizontal line indicates the mean of each dataset. The method used to identify this disease associated autoantigen is described in references (22, 30).

FIG. 9 shows the amino acid sequence of human GNS (Genbank Accession No. NP_002067.1) (SEQ ID NO: 3).

FIG. 10 shows the amino acid sequence of human filamin A (See Genbank Accession No. NP_001104026.1) (SEQ ID NO: 4).

DETAILED DESCRIPTION

Figure 1B:
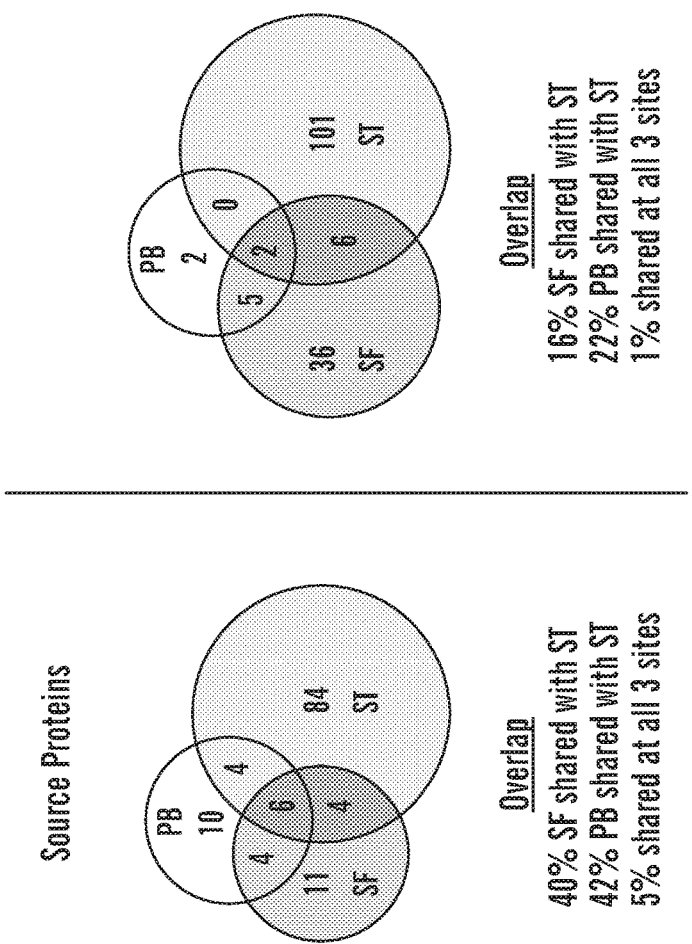

Aspects of the invention relate to the finding that N-acetylglucosamine-6-sulfatase (GNS), a lysosomal enzyme, and filamin A, an actin-binding protein, are autoantigenic in subsets of patients with rheumatoid arthritis. GNS and filamin A are targets of T cell and/or B cell responses in RA patients. This was shown by demonstrating that peripheral blood mononuclear cells (PBMC) or synovial fluid mononuclear cells (SFMC) from RA patients are stimulated by autoantigenic peptides of the GNS and filamin A. This was also shown by demonstrating that RA patients have antibodies that specifically bind to the GNS and filamin A. These findings indicate that GNS and filamin A, and immunogenic polypeptides thereof, can be used to identify immunoreactivity in a subject, with that immunoreactivity being indicative of RA disease.

One aspect of the invention relates to a method of diagnosing rheumatoid arthritis in a subject by determining whether the subject demonstrates immunological reactivity to filamin-A and/or N-acetylglucosamine-6-sulfatase. Immunological reactivity of the subject to one or more of filamin-A and N-acetylglucosamine-6-sulfatase, as compared to an appropriate control, indicates the subject has rheumatoid arthritis.

Immunoreactivity of a subject to the protein is determined, for example, by obtaining a biological sample from the subject containing antibodies or immune cells (e.g., T cells), and then assaying that biological sample for autoantigen immunoreactivity. Immunoreactivity to a molecule (e.g, a protein) can be determined using the full length molecule or one or more representative fragments or epitopes thereof. The immunological reactivity demonstrated by the subject can be T cell reactivity or B cell reactivity (e.g., has antibodies that specifically bind to the filamin-A and/or N-acetylglucosamine-6-sulfatase). T cell and B cell reactivity of a subject can be determined by various methods known in the art.

Typically, T cell reactivity is performed with an antigenic fragment of the full length molecule. B cell reactivity can be determined using a full length protein, however in some embodiment, shorter fragments may be used. Any method known in the art can be used to identify the immunological reactivity.

One aspect of the invention relates to a method for diagnosing rheumatoid arthritis in a subject by identifying the presence of antibodies in the subject that specifically bind to the filamin-A and/or N-acetylglucosamine-6-sulfatase protein or polypeptide fragment thereof. The assay involves contacting a biological sample obtained from the subject with the full length protein or representative fragments thereof (referred to as the test antigen), under conditions that allow an immunocomplex of the antibody and the polypeptide to form, and then assaying for the presence of the immunocomplex. Various methods of detecting the presence of an antibody-antigen complex are available in the art, and are suitable for use in the methods described herein, such as ELISA, agglutination test, direct immunofluorescence assay, indirect immunofluorescence assay, radioimmunoassay and immunoblot assay. A variety of immunoassay formats may be used to select antibodies specifically immunoreactive with a particular protein, (see, e.g., Harlow & Lane, Antibodies, A Laboratory Manual (1988), for a description of immunoassay formats and conditions that can be used to determine specific immunoreactivity). In one embodiment, the assay involves a detectable label that is used to facilitate detection of the complex through detection of the label. The label present in the test sample is compared to label present in a positive control and/or absent in a negative control. Appropriate controls can be determined by the skilled practitioner. In one embodiment, a negative control is the same type of biological sample obtained, for example, from a healthy subject. In one embodiment, a negative control is performed with the same sample of the subject, using a protein to which the subject has no immunoreactivity.

Reactivity that indicates detection of a significant level of the antibody complex above background (e.g., that in a negative control) indicates a positive result. In one embodiment, reactivity is identified by detection of the label. In one embodiment, a determination of reactivity that is ≥3 standard deviations (SD) above the mean of a sample of a control (e.g., of a healthy control subject) is considered a positive result. In one embodiment, a result that is at least 2-fold above background (e.g., of the signal of a sample obtained from a healthy control subject) is indicative of positive. In one embodiment, higher levels of detection are used to indicate a positive result (e.g., at least 3-fold, 4-fold, or 5-fold above background).

One aspect of the invention relates to a method for diagnosing rheumatoid arthritis in a subject by identifying the presence of T cells in the subject that are specifically reactive to GNS and/or filamin A. This is typically accomplished by obtaining a biological sample from the subject that contains T cells, and exposing the cells in the biological sample to one or more polypeptide fragments of filamin-A and/or N-acetylglucosamine-6-sulfatase (also referred to as the test fragment), and assaying for a response to the test fragment such as stimulation or proliferation. In one embodiment, peripheral blood mononuclear cells (PBMC) or synovial fluid mononuclear cells (SFMC) of the subject (e.g., in or obtained from the biological sample) are contacted with the test antigen in vitro under conditions conducive to stimulation. The cells are then monitored for a response that indicates stimulation. In one embodiment, T cell proliferation in vitro or cytokine production (e.g., IFN-γ) into the supernatant that indicates stimulation is monitored. Identification of a response (e.g., T cell proliferation or cytokine secretion) substantially over that of an appropriate control sample indicates stimulation has occurred. The level of one or more cytokines that are indicative of T cell activation can be monitored in the supernatant of the cells as an indication of T cell activation. One such cytokine is IFN-γ. Other cytokines to monitor include, without limitation IL-17, IL-12, and IL-10. The levels of one or more of such cytokines can be monitored. A significant increase in IFN-γ, IL-17, and/or IL-12, and/or a significant decrease in IL-10 levels indicates activation.

Detection of the stimulation indicates that the sample comprises immunological cells that are immunologically reactive to the test antigen, which in turn indicates that the subject from whom the sample was obtained is immunologically reactive to the test antigen. Put another way, a positive assay result indicates that the test antigen is an autoantigen in the subject, and that the subject has rheumatoid arthritis. Typical assays for use in this method are T cell proliferation assays, such as $^3$H-thymidine incorporation assay, CFSE dilution, or an ELISPOT, and also T cell reactivity assays. Methods of determining T cell reactivity are well known in the art and are described in for example U.S. Pat. No. 5,750,356A.

Reactivity that indicates a detection of a significant level of stimulation above background (e.g., that in a negative control) is expected to serve as a positive result. In one embodiment, a determination of stimulation that is ≥3 standard deviations (SD) above the mean of a sample of a healthy control subject is considered a positive result. In one embodiment, a result that is at least 2-fold above background (e.g., of the signal of a sample obtained from a healthy control subject) is indicative of positive. In one embodiment, higher levels of stimulation is used to indicate a positive result (e.g., at least 3-fold, 4-fold, or 5-fold above background).

Test antigen for use in the methods herein described include, without limitation, full length GNS, filamin A, and/or polypeptide fragments thereof.

GNS is a lysosomal enzyme, involved in the catabolism of heparin, heparan sulphate, and keratan sulphate. The GNS of the methods and kits disclosed herein can be full length GNS protein, a polypeptide fragment thereof, a derivative thereof or an antigenic portion thereof. The GNS polypeptide can be mammalian GNS. The GNS can also be an isoform of the full length GNS or a polypeptide fragment thereof. In some embodiments, the GNS of the methods and kits disclosed herein can be derived from human GNS having the amino acid sequence shown in FIG. 9 (SEQ ID NO: 3). (See Genbank Accession No. NP_002067.1, which is incorporated herein in its entirety).

In some embodiments the GNS of the methods and kits described herein can be a polypeptide fragment including or derived from human full length GNS having the amino acid sequence of SEQ ID NO: 3. The polypeptide fragment refers to fragment of the full length GNS of at least 5, at least 6, at least 7, at least 8, at least 9, at least 10, at least 11, at least 12, at least 13, at least 14, at least 15, at least 16, at least 17, at least 18, at least 19, at least 20 or more consecutive amino acids of SEQ ID NO:3, that has at least about 70%, 80%, 90%, 100% or more than 100% of the immunological reactivity of GNS of SEQ ID NO: 3. In some embodiments the polypeptide fragment comprises the amino acid FEPFF-MMIATPAPH (SEQ ID NO: 2). The immunological reactivity can be determined by T cell reactivity or B cell response to GNS and can be assayed by the skilled practitioner by the assays described herein. Examples of assays for T cell reactivity include, without limitation, measurement of in vitro T cell proliferation, measurement of in vitro IFN-γ secretion, induced in PBMC or SFMC of the subject in response to GNS. Example of assays for B cell responses include, without limitation, detection and/or measurement of autoantibodies in a biological sample that specifically recognize and/or specifically bind to GNS.

The GNS or fragment thereof used can be human GNS. The polypeptide and encoding nucleic acid sequences of GNS and of other isoforms of human origin and those of a number of animals are publically available, e.g., from the NCBI website.

The GNS or fragment thereof used can be a mammalian homolog of human GNS or a polypeptide fragment thereof. In some embodiments, the GNS polypeptide has an amino acid sequence at least 85%, at least 90%, at least 95%, at least 97% or at least 99% identical to the amino acid sequence of SEQ ID NO: 3 and has at least about 70%, 80%, 90%, 100% or more than 100% of the immunological reactivity of GNS of SEQ ID NO: 3. In some embodiments, the GNS polypeptide has an amino acid sequence that has at least 85%, at least 90%, at least 95%, at least 97% or at least 99% amino acid sequence homology to amino acid sequence of SEQ ID NO: 3 and has at least about 70%, 80%, 90%, 100% or more than 100% of the immunological reactivity of GNS of SEQ ID NO: 3. In some embodiments, the GNS is a polypeptide fragment of SEQ ID NO: 3 of at least 5, at least 6, at least 7, at least 8, at least 9, at least 10, at least 11, at least 12, at least 13, at least 14, at least 15, at least 16, at least 17, at least 18, at least 19, at least 20 consecutive amino acids of SEQ ID NO: 3, that has at least about 70%, 80%, 90%, 100% or more than 100% of the immunological reactivity of GNS of SEQ ID NO: 3.

Percent (%) amino acid sequence identity for a given polypeptide sequence relative to a reference sequence is defined as the percentage of identical amino acid residues identified after aligning the two sequences and introducing gaps if necessary, to achieve the maximum percent sequence identity, and not considering any conservative substitutions as part of the sequence identity. Percent (%) amino acid sequence homology for a given polypeptide sequence relative to a reference sequence is defined as the percentage of identical or strongly similar amino acid residues identified after aligning the two sequences and introducing gaps if necessary, to achieve the maximum percent homology. Non identities of amino acid sequences include conservative substitutions, deletions or additions that do not affect immunological reactivity of GNS or filamin a. Strongly similar amino acids can include, for example, conservative substitutions known in the art. Percent identity and/or homology can be calculated using alignment methods known in the art, for instance alignment of the sequences can be conducted using publicly available software such as BLAST, Align, ClustalW2. Those skilled in the art can determine the appropriate parameters for alignment, but the default parameters for BLAST are specifically contemplated.

Filamin A, alpha (filamin A) is an actin-binding protein that crosslinks actin filaments and links actin filaments to membrane glycoproteins. The encoded protein is involved in remodeling the cytoskeleton to effect changes in cell shape and migration. This protein interacts with integrins, transmembrane receptor complexes, and second messengers. The filamin A of the methods and kits disclosed herein can be full length filamin A protein, a polypeptide fragment thereof, a derivative thereof or an antigenic portion thereof. The filamin A or fragment thereof used can be human filamin A.

The filamin A polypeptide can be mammalian filamin A. The filamin A can also be an isoform of the full length filamin A or a polypeptide fragment thereof. In some embodiments, the filamin A of the methods and kits disclosed herein can be derived from human filamin A having the amino acid sequence shown in FIG. 10 (SEQ ID NO: 4). See Genbank Accession No. NP_001104026.1, which is incorporated herein in its entirety).

In some embodiments the filamin A of the methods and kits described herein can be a polypeptide fragment including or derived from human full length filamin A having the amino acid sequence of SEQ ID NO: 4. The polypeptide fragment refers to fragment of the full length filamin A of at least 5, at least 6, at least 7, at least 8, at least 9, at least 10, at least 11, at least 12, at least 13, at least 14, at least 15, at least 16, at least 17, at least 18, at least 19, at least 20 consecutive amino acids of SEQ ID NO: 4, that has at least about 70%, 80%, 90%, 100% or more than 100% of the immunological reactivity of filamin A of SEQ ID NO: 4. In some embodiments the polypeptide fragment comprises the amino acid sequence, NPAEFVVNTSNAGAG (SEQ ID NO: 1). The immunological reactivity can be determined by T cell reactivity or B cell response to filamin A by the skilled practitioner by assays known in the art, some of which are described herein. Examples of assays for T cell reactivity include, without limitation, measurement of in vitro T cell proliferation, measurement of in vitro IFN-γ secretion, induced in PBMC or SFMC of the subject in response to filamin A (e.g., using an immunogenic polypeptide fragment). Example of assays for B cell responses include, without limitation, detection and/or measurement of autoantibodies in a biological sample that specifically recognize and/or specifically bind to filamin A. Examples of assays for T cell reactivity include, without limitation, measurement of T cell proliferation and IFN-γ secretion by PBMC or SFMC of the subject by filamin A in vitro.

In some embodiments, human filamin A or a polypeptide fragment thereof is used. The polypeptide and coding nucleic acid sequences of filamin A and of other isoforms of human origin and those of a number of animals are publically available, e.g., from the NCBI website and are well known in the art.

In some embodiments, the filamin A of the methods and kits described herein is a mammalian homolog of human filamin A or a polypeptide fragment thereof. In some embodiments, the filamin A polypeptide has an amino acid sequence at least 85%, at least 90%, at least 95%, at least 97% or at least 99% identical to the amino acid sequence of SEQ ID NO: 4 and has at least about 70%, 80%, 90%, 100% or more than 100% of the immunological reactivity of filamin A of SEQ ID NO: 4. In some embodiments, the filamin A polypeptide has an amino acid sequence that has at least 85%, at least 90%, at least 95%, at least 97% or at least 99% amino acid sequence homology to amino acid sequence of SEQ ID NO: 4 and has at least about 70%, 80%, 90%, 100% or more than 100% of the immunological reactivity of filamin A of SEQ ID NO:4. In some embodiments, the filamin A is a functional fragment of SEQ ID NO: 4 of at least 5, at least 6, at least 7, at least 8, at least 9, at least 10, at least 11, at least 12, at least 13, at least 14, at least 15, at least 16, at least 17, at least 18, at least 19, at least 20 consecutive amino acids of SEQ ID NO: 4, that has at least about 70%, 80%, 90%, 100% or more than 100% of the immunological reactivity of filamin A of SEQ ID NO: 4.

The entire full length protein or protein fragments can be used in the assays described herein. Combinations of full length protein and protein fragments can also be used, as can combinations of proteins/fragments that represent the different autoantigens (e.g., testing for one or more of GNS and filamin A reactivity in the same assay, or side by side in the same patient). The appropriate polypeptide or fragment thereof for use in the specific method can be determined by the skilled practitioner. The proteins or fragments can be can be recombinant, purified, isolated, naturally occurring or synthetically produced. The term "recombinant" when used in reference to a nucleic acid, protein, cell or a vector indicates that the nucleic acid, protein, vector or cell containing them have been modified by introduction of a heterologous nucleic acid or protein or the alteration of a native nucleic acid or a protein, or that the cell is derived from a cell so modified. The term "heterologous" (meaning 'derived from a different organism') refers to the fact that often the transferred protein was initially derived from a different cell type or a different species from the recipient. Typically the protein itself is not transferred, but instead the genetic material coding for the protein (often the complementary DNA or cDNA) is added to the recipient cell.

Methods of generating and isolating recombinant polypeptides are known to those skilled in the art and can be performed using routine techniques in the field of recombinant genetics and protein expression. For standard recombinant methods, see Sambrook et al, Molecular Cloning: A Laboratory Manual, Cold Spring Harbor Laboratory Press, NY (1989); Deutscher, Methods in Enzymology 182:83-9 (1990); Scopes, Protein Purification: Principles and Practice, Springer-Verlag, NY (1982).

Either the full length protein, or protein fragments derived from the full length protein, can be used to identify immunoreactivity in a subject to the proteins disclosed herein. The specific molecules used in the assays described herein (e.g., full length protein(s), representative fragments thereof, or a combination of the full length and fragments) are referred to as the "test antigen" in the assay descriptions. Which fragments of a full length protein to use in the assay can be determined by the skilled practitioner. Typically, a cocktail of fragments derived from the same protein are used for determination of reactivity of a subject to that protein. Depending upon the length, the number of different protein fragments can be determined and optimized by the skilled practitioner. In one embodiment, 2 or more protein fragments are used. In one embodiment, 3 or more, 4, 5, 6, 7, 8, 9, or 10 or more protein fragments are used. In one embodiment, a protein fragment is at least 8 amino acids in length (e.g., ≥8, ≥9, ≥10, ≥11, ≥12, ≥13, ≥14, ≥15 amino acids).

Specific protein fragments can be identified for use in the herein described methods such as those predicted for presentation by HLA-DR. Such protein fragment can be identified by the methods described in the examples and also by a variety of software programs available to the skilled practitioner (Lin et al. BMC Immunology 2008, 9:8). In one embodiment, TEPITOPE 2000 (Sturniolo et al. 1999 Nature Biotechnology. 17; 555-561) is used. Other freely accessible online programs offered by the Immune Epitope Database and Analysis Resource (http://www.iedb.org/) are also available.

Examples of specific protein fragments of filamin A include, without limitation NPAEFVVNTSNAGAG (SEQ ID NO: 1).

Examples of specific protein fragments of GNS include, without limitation FEPFFMMIATPAPH (SEQ ID NO: 2).

Reactivity to one or both of GNS and filamin A can be assayed in a single subject. In one embodiment, reactivity to both GNS and filamin A are assayed in a subject. In one embodiment, reactivity in a subject to other suspected autoantigens is also performed in combination with the herein described assays. One such autoantigen is cyclic citrullinated peptide (CCP). Several assays for detecting anti-citrullinated protein antibody (ACPAs) are known in the art employing mutated citrullinated Vimentin (MCV-assay), filaggrin-derived peptides (CCP-assay) and viral citrullinated peptides (VCP-assay). Methods for determination of reactivity of a subject for anti-CCP and/or other markers for disease diagnosis are known in the art. Non limiting examples include WO 2005/085858 discloses a method of assessing RA by measuring CCP and serum amyloid A (SAA). WO 2005/064307 and US 2007/0264673 assess RA by measuring CCP and IL-6. WO 2005/029091 and US 2006/094056 provide methods to diagnose, treat, or evaluate inflammatory/autoimmune diseases such as RA by sampling fluids from a human with a suspected diagnosis by detecting CCP. US 2007/0148704 and WO 2007/039280 disclose use of CCP and antibodies as biomarkers in diagnosing RA. WO 2006/008183 discloses various biomarkers for RA.

Symptoms of RA

A subject suspected of having rheumatoid arthritis can be tested by the methods described herein. The subject may exhibit one or more symptoms of rheumatoid arthritis prior to performance of the methods. Rheumatoid arthritis (RA) is an autoimmune disease that causes the body's immune system to attack joint tissues, which leads to inflammation of joint lining Inflammation of the joints is the primary manifestation of RA. Early symptoms of RA include affected joints being swollen, tender, warm, painful and stiff especially in the morning. Morning stiffness may last for at least an hour. The pain associated with RA is induced at the site of inflammation. Non limiting examples of other symptoms for RA include presence of rheumatoid nodules in the skin, fatigue, joint deformity and reduction in range of motion of affected joints, dryness of eyes and mouth. Early symptoms associated with RA are also seen in patients with other autoimmune related diseases such as lupus, or in other forms of arthritis, such as osteoarthritis, or in the pain syndrome, fibromyalgia. Accordingly, in some embodiments of the present invention, the subject exhibits symptoms of RA and/or other autoimmune related disease manifestation known in the art e.g., Tenosynovitis, osteoporosis, carpal tunnel syndrome.

Diagnosis of Rheumatoid Arthritis in a Subject

There is no unique test or feature that is pathognomonic for RA. Rather, the diagnosis is made by recognizing a pattern of signs and symptoms. Classification criteria based on symptoms for identifying subjects suffering to early stages of RA and therefore aiding in disease diagnosis are known in the art and are for example set forth in 1987 American College of Rheumatology (ACR) criteria (72) and recently 2010 criteria by ACR and the European League Against Rheumatism (EULAR) (73).

The diagnostic methods of RA includes X-ray, MRI and/or ultrasound imaging of the affected joints and blood/serological tests. Non limiting examples of blood/serology tests known in the art to be conducted for diagnosis of RA include measurements of; Erythrocyte Sedimentation Rate (ESR), Rheumatoid factor (RF), Anti-cyclic Citrullinated Peptide (anti-CCP), Antinuclear Antibody (ANA), Uric Acid, complete blood count: measures the numbers of red and white cells in your blood, C-reactive protein (CRP). In RA, 10 HLA-DR alleles, including the HLA-DRB1*0101 and 0401 alleles (6, 7) convey the greatest risk. Accordingly, in some embodiments, the subject has been or is further tested for one or more of rheumatoid factor (RF), anti-citrullinated protein antibodies (ACPA), and one or more of HLA-DR alleles. Non-limiting examples of HLA-DR alleles that can be tested for include HLA-DRB1*0101, HLA-DRB1*0401.

In some embodiments, identification of immunoreactivity to one or more of the proteins described herein can be used in diagnosis of RA. In some embodiments, the methods disclosed herein can be used to identify a patient with RA. In some embodiments, the methods disclosed herein can be used for differential diagnosis of RA. Immunoreactivity of a subject to one or more of the proteins can determined in vitro using suitable biological samples disclosed herein by a variety of methods available to the skilled practitioner.

The discoveries presented herein indicate that reactivity to GNS and filamin A can be used as a biomarker for the diagnosis of a condition (e.g., RA and associated symptoms). More specifically, subject immunoreactivity (e.g., autoantigen reactive T cells, and/or anti-autoantigen antibodies) is indicative of the condition. As such, another aspect of the invention relates to a method of diagnosing the condition in a subject (e.g., RA) by determining whether the subject is immunologically reactive with one or more of GNS or filamin A by the herein described methods. The determination may be made in conjunction with the presence of other such symptoms of the condition present in the subject, for example, arthritic symptoms in a subject, or neurologic symptoms in a subject, or cardiac symptoms in a subject. The determination of immunological reactivity of a subject, as compared to an appropriate control, indicates the subject has, or is likely to develop, the condition. The condition can be further confirmed by the determination of immunological reactivity to additional proteins such as antibodies to citrullinated proteins (ACPA), antinuclear antibody (ANA), anti-neutrophil cytoplasmic antibodies (ANCA) and presence of rheumatoid factors and other diagnostic tests known to those skilled in the art and described above.

Various assays can be used to identify antibodies present in a serum sample that bind the test antigen (e.g., ELISA, agglutination test, direct immunofluorescence assay, indirect immunofluorescence assay, western blot, an immunoblot assay). For example, the assay could be an immunoblot that carries a recombinant test antigen (full length or peptide fragment(s)).

The methods described herein can also include determination of rheumatoid factor, ACPA and/or ANA. For example, the test antigens disclosed herein can be included in or used in conjunction with an assay such as the SureVue® RF (Fishersci), RFscan™ Card Test Kit (BD Biosciences), Anti-Rheumatoid Factor IgM ELISA Kit (abcam), AVITEX®-RF (Omega diagnostics) Citrullinated Protein Antibodies IgG ELISA Kit (Omega diagnostics) Anti-CCP EIA (Bio-Rad), BioPlex® 2200 Anti-CCP (Bio-Rad), CCPoint® (Eurodiagnostica), DIASTAT® anti-nuclear antibody (ANA) test (Eurodiagnostica), DIASTATR PR3-ANCA® (Eurodiagnostica). The protein Filamin A or GNS or fragments thereof may be included in such a kit.

Test-antigen reactive T cells in PBMC and SFMC can be assessed using a number of assays. For example, reactive T cells in PBMC and SFMC can be assessed using tetramer reagents comprising recombinant HLA-DR molecules and test antigen epitopes.

The test antigen may comprise naturally occurring or analog or derivative amino acids, as long as the immunoreactive or immunostimulatory nature of the peptide is retained to sufficient degree to allow T cell activation and/or antibody binding. Thus, some amino acids may be added to or subtracted from the native protein or polypeptide fragments as known in the art. Additionally, some amino acids of the native human protein or polypeptide fragments may be substituted with amino acids that occur in other species, or be substituted as known in the art. Amino acid substitution exchange groups and empirical similarities between amino acid residues, can be found in standard texts such as Schulz et al., Principles of Protein Structure, 14-16 (Springer-Verlag, New York, 1979). There is a limit to how much substitution can be tolerated before the original tertiary structure is lost. Typically, tertiary structure conservation would be lost when the amino acid sequence varies by more than 50%. See, e.g., Chothia & Lesk, *Relation between the divergence of sequence & structure in proteins*, 5 EMBO J. 823 (1986). Guidance concerning which amino acid changes are likely to be phenotypically silent is found in Bowie et al., 247 Science 1306 (1990). Amino acids that are essential for function can be identified by methods known in the art, such as site-directed mutagenesis or alanine-scanning mutagenesis. Cunningham et al., 244 Science 1081 (1989). The latter procedure introduces single alanine mutations at every residue in the molecule. The resulting mutant molecules are then tested for biological activity such as antibody binding and/or T cell stimulation. Sites that are critical for ligand-receptor binding can also be determined by structural analysis such as crystallography, nuclear magnetic resonance, or photoaffinity labeling. Smith et al., 224 J. Mol. Biol. 899 (1992); de Vos et al., 255 Science 306 (1992).

The genes and encoded proteins of the autoantigens described herein have been sequenced and are available at numerous sources. Further, the genes are conserved in human, chimpanzee, rat, and zebrafish. Hence, these peptides can include those derived from non-human sources or appropriate sequence information. In an aspect of the invention, the test peptide is predicted to be presented by HLA-DR molecules associated with chronic inflammatory arthritis (e.g., RA).

As noted above, generally, amino acid substitutions should be made conservatively; i.e., a substitute amino acid should replace an amino acid that has similar properties, such that one skilled in the art of peptide chemistry would expect the secondary structure and hydropathic nature of the polypeptide to be substantially unchanged. In general, the following groups of amino acids represent conservative changes: (1) ala, pro, gly, glu, asp, gln, asn, ser, thr; (2) cys, ser, tyr, thr; (3) val, ile, leu, met, ala, phe; (4) lys, arg, his; and (5) phe, tyr, trp, his. Variants within the scope of this invention may also, or alternatively, contain other modifications, including the deletion or addition of amino acids, that have minimal influence on the stimulatory properties, antibody binding, tertiary structure of the peptide. Thus, for example, conservative substitutions in a protein fragment can be made with the proviso that functional activity is retained to a meaningful degree such that the particular assay (e.g., T cell reactivity or immunoassay) works as intended to provide evidence in diagnosing subjects (e.g., with RA).

Moreover, peptides often contain amino acids other than the twenty "naturally occurring" amino acids. Further, many amino acids, including the terminal amino acids, may be modified by natural processes, such as processing and other post-translational modifications, or by chemical modification techniques well known in the art. Known modifications include, but are not limited to, acetylation, acylation, ADP-ribosylation, amidation, covalent attachment of flavin, covalent attachment of a heme moiety, covalent attachment of a nucleotide or nucleotide derivative, covalent attachment of a lipid or lipid derivative, covalent attachment of phosphotidylinositol, cross-linking, cyclization, disulfide bond formation, demethylation, formation of covalent crosslinks, formation of cystine, formation of pyroglutamate, formylation, gamma carboxylation, glycosylation, GPI anchor formation, hydroxylation, iodination, methylation, myristoylation, oxidation, proteolytic processing, phosphorylation, prenylation, racemization, selenoylation, sulfation, transfer-RNA mediated addition of amino acids to proteins such as arginylation, and ubiquitination.

Such modifications are well known to those of skill in the art and have been described in great detail in the scientific literature. Several particularly common modifications, glycosylation, lipid attachment, sulfation, gamma-carboxylation of glutamic acid residues, hydroxylation and ADP-ribosylation, for instance, are described in most basic texts, such as Creighton, PROTEINS—STRUCTURE & MOLECULAR PROPERTIES (2nd ed., W.H. Freeman & Co., New York, 1993). Many detailed reviews are available on this subject, such as by Wold, POSTTRANSLATIONAL COVALENT MODIFICATION OF PROTEINS, 1-12 (Johnson, ed., Academic Press, New York, 1983); Seifter et al. 182 Meth. Enzymol. 626 (1990); Rattan et al., 663 Ann. N.Y. Acad. Sci. 48 (1992). Accordingly, the peptides of the present invention also encompass derivatives or analogs in which a substituted amino acid residue is not one encoded by the genetic code.

Further, "derivatives" of a test antigen contain additional chemical moieties not normally a part of the protein. Covalent modifications of the autoantigens are included within the scope of this invention. Such modifications may be introduced into the molecule by reacting targeted amino acid residues of the antibody with an organic derivatizing agent that is capable of reacting with selected side chains or terminal residues. For example, derivatization with bifunctional agents, well-known in the art, is useful for cross-linking the antibody or fragment to a water-insoluble support matrix or to other macromolecular carriers. Derivatives also include radioactively labeled peptides that are labeled, for example, with radioactive iodine (125I, 131I), carbon (14C), sulfur (35S), tritium (3H) or the like; conjugates of peptides with biotin or avidin, with enzymes, such as horseradish peroxidase, alkaline phosphatase, β-D-galactosidase, glucose oxidase, glucoamylase, carboxylic acid anhydrase, acetylcholine esterase, lysozyme, malate dehydrogenase or glucose 6-phosphate dehydrogenase; and also conjugates of monoclonal antibodies with bioluminescent agents (such as luciferase), chemoluminescent agents (such as acridine esters), or fluorescent agents (such as phycobiliproteins).

Structural analogs of the autoantigens identified herein are provided by known method steps based on the teaching and guidance presented herein. Knowledge of the three-dimensional structures of proteins is crucial in understanding how they function. The three-dimensional structures of hundreds of proteins are currently available in protein structure databases (in contrast to the thousands of known protein sequences in sequence databases). Analysis of these structures shows that they fall into recognizable classes of motifs. It is thus possible to model a three-dimensional structure of a protein based on the protein's homology to a related protein of known structure. Many examples are known where two proteins that have relatively low sequence homology, can have very similar three dimensional structures or motifs.

It is possible to determine the three dimensional structures of proteins of up to about 15 kDa by nuclear magnetic resonance (NMR). The technique only requires a concentrated solution of pure protein. No crystals or isomorphous derivatives are needed. The structures of a number of proteins have been determined by this method. The details of NMR structure determination are well-known in the art. See, e.g., Wuthrich, NMR of Proteins & Nucleic Acids (Wiley, N.Y., 1986); Wuthrich, 243 Science 45 (1989); Clore et al., 24 Crit. Rev. Bioch. Molec. Biol. 479 (1989); Cooke et al., 8 Bioassays 52 (1988).

Thus, according to the present invention, use of NMR spectroscopic data can combined with computer modeling to arrive at structural analogs of at least portions of the autoantigen (peptides or epitopes) based on a structural understanding of the topography. Using this information, one of ordinary skill in the art can achieve structural analogs of autoantigens such as by rationally-based amino acid substitutions allowing the production of peptides in which the binding affinity or avidity is modulated in accordance with the requirements of the expected diagnostic use of the molecule, for example, the achievement of greater binding specificity or affinity.

The herein described methods may further be used to indicate a therapy for the subject who tests positive. The identification of GNS and/or filamin A for a biomarker in RA, as provided herein, is an important addition to the clinician's arsenal in combating chronic inflammatory arthritis, and assists the clinician in choosing the course of therapy. For example, when RA is diagnosed, nonsteroidal anti-inflammatory drugs (NSAIDs) (e.g., ibuprofen, naproxen sodium) or steroids (e.g., corticosteroid medication such as prednisone); or disease modifying anti-rheumatic drugs (DMARDs), such as hydroxychloroquine, sulfasalzine or methotrexate, may be prescribed. Additionally or alternatively, anti-TNF therapy (e.g., HUMIRA® (adalimumab), ENBREL® (etanercept), may be beneficial. Other non-limiting examples include Orencia® (abatacept), Kineret® (anakinra), Certolizumab® (Cimzia), Simponi® (golimumab), Remicade® (infliximab), Actemra® (tocilizumanb) and Xelijanz® (tofacitinib). It is also contemplated that GNS and/or filamin A-specific therapy, such as targeting GNS and/or filamin A e.g., GNS and/or filamin A-binding antibodies, may also be beneficial. In one embodiment, the subject is provided one or more therapies following an indication that they are immunoreactive to an autoantigen. As such, another aspect of the invention relate to a method of treating a subject diagnosed with a RA. The method comprises diagnosing the subject for the disorder by one or more of the herein described methods, and then treating the subject for said condition. Diagnosis may further include assessing the subject for other symptoms such as a neurological condition or heart condition typically seen with secondary RA symptoms. In some embodiments of the present invention, the methods to determine immunoreactivity to autoantigens disclosed herein can be conducted prior to, during and/or after a therapeutic treatment and therefore aid in assessment of effectiveness of the treatment and/or monitor disease progression.

Another aspect of the invention relates to a kit for identifying a subject with a condition such as chronic inflammatory arthritis. The kit comprises one or more of GNS, filamin A, or a portion or fragment thereof, such as a set of synthesized peptides, fragments, or epitopes thereof, and reagents necessary for conducting an assay capable of detecting the presence of immunoreactivity of a subject to that test antigen (e.g., an antibody in a sample obtained from said subject that binds to GNS and/or filamin A). The kit can be designed for any of the various assays described herein. In one embodiment, the assay in the kit is an enzyme-linked immunosorbent assay (ELISA) or immunoblot, the components for which are well-known in the art. The peptides may be synthesized or obtained from natural or recombinant sources, each of which is well-known in the art. The kit may further include other autoantigens known in the art, such as those described herein. (e.g., citrullinated protein/peptides such as citrullinated filaggrin, fibrinogen, fibronectin, α-enolase, collagen type II, histones, vimentin or fragments/epitopes thereof). The kit may alternately further comprise buffers, enzymes, and/or containers for performing the reactions or analyses. The various reagents within the kit may be provided separately or together as is convenient in a container such as a vial, test tube, flask, bottle or even syringe. The components may be suitably aliquotted for performance of the methods. The kit may further contain one or more positive and/or negative controls. The antigens or other components of the kit may be labeled with a detectable marker.

Unless otherwise defined herein, scientific and technical terms used in connection with the present application shall have the meanings that are commonly understood by those of ordinary skill in the art. Further, unless otherwise required by context, singular terms shall include pluralities and plural terms shall include the singular.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Other than in the operating examples, or where otherwise indicated, all numbers expressing quantities of ingredients or reaction conditions used herein should be understood as modified in all instances by the term "about." The term "about" when used to described the present invention, in connection with percentages means ±1%.

In one respect, the present invention relates to the herein described compositions, methods, and respective component (s) thereof, as essential to the invention, yet open to the inclusion of unspecified elements, essential or not ("comprising). In some embodiments, other elements to be included in the description of the composition, method or respective component thereof are limited to those that do not materially affect the basic and novel characteristic(s) of the invention ("consisting essentially of"). This applies equally to steps within a described method as well as compositions and components therein. In other embodiments, the inventions, compositions, methods, and respective components thereof, described herein are intended to be exclusive of any element not deemed an essential element to the component, composition or method ("consisting of").

All patents, patent applications, and publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Embodiments of various aspects described herein can be defined in any of the following numbered paragraphs:

1. A method of diagnosing rheumatoid arthritis in a subject comprising determining whether the subject is immunologically reactive with one or more of filamin-A and N-acetylglucosamine-6-sulfatase, wherein immunological reactivity of the subject to one or more of filamin-A and N-acetylglucosamine-6-sulfatase, as compared to an appropriate control, indicates the subject has rheumatoid arthritis.
2. The method of paragraph 1, wherein determining is by evaluating a biological sample obtained from the subject for immunological reactivity with the one or more of filamin-A and N-acetylglucosamine-6-sulfatase.
3. The method of any one of paragraphs 1-2, wherein determining immunological reactivity is by detecting the presence of T cells reactive to one or more of filamin-A and N-acetylglucosamine-6-sulfatase, comprising the steps:
   a) stimulating peripheral blood mononuclear cells (PBMC) of the subject or the synovial fluid mononuclear cells (SFMC) of the subject in vitro with one or more of filamin-A and N-acetylglucosamine-6-sulfatase, whole protein or polypeptide fragments;
   b) measuring T cell proliferation in vitro or secretion of IFN-γ into cell culture supernatants; and
   c) identifying the subject as having T cells reactive to one or more of filamin-A and N-acetylglucosamine-6-sulfatase when T cell proliferation or secretion of IFN-γ is measured as significantly increased over that of an appropriate control.
4. The method of paragraph 3, wherein step b) is measuring T cell proliferation in vitro, and the subject is identified as having T cell reactive to one or more of filamin-A and N-acetylglucosamine-6-sulfatase when T cells proliferation is measured as significantly increased over that of an appropriate control.
5. The method of paragraph 3, wherein step b) is measuring T cell secretion of IFN-γ into cell culture supernatants, and the subject is identified as having T cells reactive to one or more of filamin-A and N-acetylglucosamine-6-sulfatase when secretion of IFN-γ is measured as significantly increased over that of an appropriate control.
6. The method of any one of paragraphs 1-5, wherein determining immunological reactivity comprises determining if the subject has a B-cell response to one or more of filamin-A and N-acetylglucosamine-6-sulfatase resulting in the production of autoantibodies that specifically recognize the one or more filamin-A and N-acetylglucosamine-6-sulfatase, by contacting the sample with filamin-A protein or a polypeptide fragment thereof and/or N-acetylglucosamine-6-sulfatase protein or a polypeptide fragment thereof, under conditions that allow an immunocomplex of the antibody and the filamin-A or N-acetylglucosamine-6-sulfatase form, and detecting the presence or absence of an immunocomplex, wherein the presence of an immunocomplex indicates the subject presents a B-cell response to filamin-A and/or N-acetylglucosamine-6-sulfatase and wherein the absence of an immunocomplex indicates the subject fails to present a B-cell response to filamin-A and/or N-acetylglucosamine-6-sulfatase.
7. The method of paragraph 6, wherein the assay is an enzyme-linked immunosorbent assay (ELISA), agglutination test, direct immunofluorescence assay, indirect immunofluorescence assay, or an immunoblot assay.
8. The method of any one of paragraphs 3-7, wherein the polypeptide fragment of filamin-A comprises the amino acid sequence NPAEFVVNTSNAGAG (SEQ ID NO: 1) or an antigenic portion thereof.
9. The method of any one of paragraphs 3-8, wherein the polypeptide fragment of N-acetylglucosamine-6-sulfatase comprises the amino acid sequence of FEPFFMMIATPAPH (SEQ ID NO: 2) or an antigenic portion thereof.
10. The method of any one of paragraphs 1-9 wherein the subject has been or is further tested for one or more of rheumatoid factor, anti-citrullinated protein antibodies (ACPA), and one or more HLA-DR alleles.
11. The method of paragraph 10, wherein the HLA-DR allele is HLA-DRB1*0101 and/or HLA-DRB1*0401.
12. The method of any one of paragraphs 1-11, wherein the subject is at risk for, or is suspected of having, rheumatoid arthritis.

13. The method of any one of paragraphs 1-12, further comprising the step of treating the subject with one or more of a nonsteroidal anti-inflammatory drug (NSAIDs), a steroid, a disease modifying anti-rheumatic drug (DMARD), and a biologic.
14. A kit comprising, one or more potential antigen and/or potential epitope of filamin-A and/or N-acetylglucosamine-6-sulfatase, and reagents for conducting an assay for detecting the presence of an antibody in a sample that binds to the one or more potential antigen and/or potential epitope of the filamin-A and N-acetylglucosamine-6-sulfatase.
15. The kit of paragraph 14, wherein the potential antigen and/or potential epitope of filamin-A comprises the amino acid sequence NPAEFVVNTSNAGAG (SEQ ID NO: 1) or an antigenic portion thereof.
16. The kit of paragraph 14, wherein the potential antigen and/or potential epitope of N-acetylglucosamine-6-sulfatase comprises the amino acid sequence FEPFFMMIATPAPH (SEQ ID NO: 2) or an antigenic portion thereof.
17. The kit of any one of paragraphs 14-16, wherein the assay is an enzyme-linked immunosorbent assay (ELISA).
18. The kit of any one of paragraphs 14-16, wherein the assay is a western blot.
19. The kit or method of any one of paragraphs 1-18 for use in identifying a subject with rheumatoid arthritis.

The invention is further illustrated by the following examples, which should not be construed as further limiting.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The technology described herein is further illustrated by the following examples which in no way should be construed as being further limiting.

Example 1

Background

Identification of autoantigens has been a great challenge in autoimmune diseases such as rheumatoid arthritis (RA). To address this issue, a new method that combines discovery based proteomics to identify HLA-DR-presented peptides in patients' synovial tissues, joint fluid or peripheral blood (PB) and translational research to determine the immunogenicity of the identified peptides and their source proteins is described herein. With this approach, endothelial cell growth factor was recently identified as a target or T and B cell responses in Lyme arthritis (LA) (22) and annexin A2 as such a target in both LA and RA (26).

Objectives

To identify novel disease-associated autoantigens which induce T and B cell responses in patients with RA.

Methods

HLA-DR-presented self-peptides were isolated and identified from RA patients' tissue or fluids by tandem mass spectrometry, synthesized and tested for T cell autoreactivity with the matching patient's peripheral blood mononuclear cells (PBMC). Immunoreactive peptides or their source proteins were then tested for T cell autoreactivity by IFN-g ELISpot assay and for autoantibody responses by ELISA using cells and sera from our large cohort of RA patients and control subjects. All RA patients met the 2010 ACR/EULAR criteria for RA.

Results

In the RA patient, 1 of 89 HLA-DR-presented peptides identified from her synovial tissue and 1 of 15 HLA-DR-presented peptides identified from her PB induced her PBMC to secrete IFN-g. These reactive peptides were derived from the proteins N-acetylglucosamine-6-sulfatase (GNS), a lysosomal enzyme, and from filamin A (filamin A), an actin-binding protein, respectively. It was found that 8 of 25 RA patients (32%) had T cell reactivity with GNS that was >3 SD above the mean value of 10 healthy controls (HC) (p=0.004), and 13 of the 25 patients (52%) had T cell reactivity to filamin A (p=0.002). In addition, 35% of 92 RA patients had elevated autoantibody responses to GNS that were >3 SD above the mean value of 50 HC (p<0.0001), and 32% of the patients had high autoantibody responses to filamin A (p<0.0001).

Of the 92 patients, 52 (56%) had a response to one of these autoantigens, and 10 (11%), including the case patient, had reactivity with both autoantigens. Compared with patients with RA, none of 94 patients with other rheumatic diseases, including systemic lupus (SLE), psoriatic arthritis, spondyloarthritis, Lyme arthritis, or osteoarthritis had B cell reactivity with GNS (in each instance, p<0.0001), and only 3 patients with SLE (p=0.003) and 1 with psoriatic arthritis (p<0.0001) had responses to filamin A that were slightly above the cut-off value.

Conclusions

This approach is an effective way to identify novel autoantigens associated with autoimmune forms of arthritis. With this method, two previously unrecognized autoantigens were identified, each of which is a target of T and B cell responses in about ⅓ of patients with RA, but rarely in those with other types of arthritis. These findings suggest that testing for these newly recognized autoantibodies may have diagnostic utility in RA.

Example 2

With the advent of highly sensitive, nanoflow LC-MS/MS-based peptide sequencing (31), it has become possible to identify peptides presented by HLA-DR molecules in individual patients' tissues or cells. In 1992, Hunt et al. were the first to use LC-MS/MS to identify class I major histocompatibility complex (MHC) molecules in tumor tissue culture systems (32). They have continued to lead this rapidly growing field, and the identification of MHC-presented peptides has been widely undertaken primarily using cell lines (33-41). Moreover, advances in mass spectrometry techniques and bioinformatics have improved the efficiency and accuracy for identification of MHC-presented molecules (42, 43).

As a next step, a few laboratories have undertaken the direct analysis of class II HLADR-presented peptides in clinical samples of mixed cell lines (44-49). In previous study, 57-104 non-redundant, HLA-DR-presented self-peptides per patient from the ST of four patients, two with RA and two with LA were identified (30). However, large amounts of synovial tissue can only be obtained when patients undergo surgical procedures, such as synovectomy or joint replacement, and this limits the analysis to patients at the severe end of the spectrum, usually seen late in the illness.

In present study, the number of patients studied were increased to thirteen, five with RA and eight with LA. Moreover, it was demonstrated that HLA-DR-presented peptides could be identified in individual patients—not only from ST, but also from synovial fluid mononuclear cells (SFMC) and peripheral blood mononuclear cells (PBMC), which allow the analysis not only of a greater number of patients, but also of patients seen earlier in the illness. In addition, the increasing sensitivity of new mass spectrometers and improvements in computer programs for spectrum-to-peptide matches resulted in the identification of greater numbers of HLA-DR-presented peptides from each sample. In the current study, 18 new ST, PBMC and SFMC samples were analyzed and previous LC-MS/MS data were re-analyzed to compare with new data from SFMC and PBMC samples.

Altogether, from 22 samples that originated from 13 patients, we identified 1,593 nonredundant HLA-DR-presented, self-peptides derived from 870 source proteins. This experience shows that LC-MS/MS now has the sensitivity and specificity to identify large numbers of HLADR-presented self-peptides in tissues and fluids with mixed cell populations, obtained from individual patients. After the peptides were synthesized and tested with the matching patient's PBMC, it was determined that among these peptides were novel immunogenic T cell epitopes derived from the source proteins endothelial cell growth factor (ECGF) (22) apolipoprotein B-100 (apoB-100) (23), matrix metalloproteinase-10 (MMP-10) (24) in LA; from annexin A2 in both RA and LA (25) and from N-acetylglucosamine-6-sulfatase and filamin A in RA (26). Furthermore, it was shown that these epitopes or their source proteins were targets of T and B cell responses in many patients (22-26).

Results

Patients—All five patients with RA were women, ages 37 to 70 (Table 1), a distribution which reflects the gender bias associated with RA. Three of the five patients had classic, seropositive RA. They had the HLA-DRB1*0101 or 0401 alleles, which code for the RA shared epitope; these three patients had ACPA and two had rheumatoid factor (RF). The remaining two RA patients had chronic seronegative RA. They did not have shared epitope alleles, and their tests were negative for ACPA and RF. In four patients, ST from a hip or knee was obtained when arthroscopic synovectomy or joint replacement surgery was performed three to 66 years after disease onset. For one patient (RA2), samples were available from all three sites (ST, SFMC and PBMC), and, for patient RA4, SFMC and PBMC samples (but not ST) were collected at the time of diagnosis, prior to therapy with disease modifying anti-rheumatic drugs (DMARDs).

The eight patients with antibiotic-refractory LA included four teenage boys, three adult men and one woman (Table 1). Four of the eight patients had the HLA-DR*0101, 0401 or 1501 alleles, which are known to be increased in frequency in patients with refractory LA (58). All eight patients were treated with ≥two months of oral antibiotics, seven also received ≥one month of IV antibiotics, and seven subsequently received methotrexate. Due to incomplete resolution of synovitis, the eight patients underwent arthroscopic synovectomies of an affected knee six months to four years after the onset of arthritis, and ST samples were obtained during the surgeries. Additionally, SFMC samples were available from four patients and PBMC from two patients.

TABLE 1

Clinical characteristics, number of MS/MS spectra, peptide matches, decoy hits, non-redundant peptides, and source proteins identified from each patient's HLA-DR molecules in synovial tissue, synovial fluid or peripheral blood.

| | Rheumatoid Arthritis | | | | | Lyme Arthritis | | |
|---|---|---|---|---|---|---|---|---|
| Patient | RA1 | RA2 | RA3 | RA4 | RA5 | LA1 | LA2 | LA3 |
| Gender | F | F | F | F | F | M | M | M |
| Age (years) | 70 | 37 | 45 | 63 | 68 | 12 | 43 | 18 |
| Arthritis Duration (years) | 66 | 3 | 7 | 1 | 3 | 1.1 | 1.6 | 0.5 |
| Anti-citrullinated protein antibodies | neg | pos | pos | pos | neg | neg | neg | neg |
| Rheumatoid factor | neg | pos | pos | neg | neg | neg | neg | neg |
| HLA-DR*B1 genotype | 0402/1104 | 0101/0401 | 0101/0401 | 0401/1501 | 0801/1501 | 0101/0801 | 1001/1101 | 0301/1501 |
| Synovial tissue, No. of | | | | | | | | |
| MS/MS spectra | 1647[1] | 1712[1] | 5487[452] | 10220[2] | 10375[2] | 2237[1] | 1664[1] | 9637[2] |
| spectrum-to-peptide matches | 1031 | 1323 | 637 | 2538 | 1852 | 1082 | 696 | 4516 |
| consensus matched peptides | 248 | 292 | 107 | 471 | 145 | 282 | 135 | 481 |
| Decoy hits | 1 | 0 | 0 | 1 | 0 | 0 | 0 | 0 |
| consensus non-decoy non-redundant peptides | 95 | 94 | 61 | 172 | 68 | 95 | 57 | 167 |
| peptides tested for immune responses identified by only one program | 18 | 8 | | | | 12 | 2 | 10 |
| Immunogenic peptides | 1 | 2 | N/A | NYD | 1 | 0 | 0 | |
| Source proteins | 80 | 78 | 45 | 126 | 52 | 79 | 42 | 136 |
| Synovial fluid mononuclear cells, No. of | | | | | | | | |
| MS/MS spectra | | 20979[1] | 5120[4] | 16169[2] | | | 14244[2] | |
| spectrum-to-peptide matches | | 2461 | 254 | 1145 | | | 1694 | |
| consensus matched peptides | | 30 | 51 | 66 | | | 2 | |
| Decoy hits | | 1 | 0 | 0 | | | 0 | |
| consensus non-decoy non-redundant peptides | | 15 | 32 | 37 | | | 2 | |
| peptides tested for immune responses identified by only one program | | | | | | | | |

TABLE 1-continued

Clinical characteristics, number of MS/MS spectra, peptide matches, decoy hits, non-redundant peptides, and source proteins identified from each patient's HLA-DR molecules in synovial tissue, synovial fluid or peripheral blood.

| | | | | |
|---|---|---|---|---|
| Immunogenic peptides | 0 | 0 | 0 | 0 |
| Source proteins | 14 | 23 | 32 | 2 |
| Peripheral blood mononuclear cells, No. of | | | | |
| MS/MS spectra | 20931[2] | 6227[4] | 11060[2] | |
| spectrum-to-peptide matches | 1897 | 372 | 1216 | |
| consensus matched peptides | 22 | 60 | 7 | |
| Decoy hits | 0 | 0 | 0 | |
| consensus non-decoy non-redundant peptides | 14 | 31 | 7 | |
| peptides tested for immune responses identified by only one program | | | | |
| Immunogenic peptides | 1 | 1 | 0 | |
| Source proteins | 11 | 24 | 7 | |

| | | Lyme Arthritis | | | | | |
|---|---|---|---|---|---|---|---|
| Patient | LA4 | LA5 | LA6 | | LA7 | | LA8 | |
| Gender | M | F | M | | M | | M | |
| Age (years) | 38 | 51 | 14 | | 16 | | 15 | |
| Arthritis Duration (years) | 1.6 | 4 | 0.83 | | 0.83 | | 0.75 | |
| Anti-citrullinated protein antibodies | neg | neg | neg | | neg | | neg | |
| Rheumatoid factor | neg | neg | neg | | neg | | neg | |
| HLA-DR*B1 genotype | 1101/1302 | 0301/0305 | 0103/0301 | | 0403/1501 | | 0401/1001 | |
| Synovial tissue, No. of | | | | | | | | |
| MS/MS spectra | 11940[2] | 14141[2] | 5892[2] | 9195[3] | 6090[2] | 20249[3] | 29454[3] | 10936[4] |
| spectrum-to-peptide matches | 2531 | 2453 | 621 | 4445 | 1214 | 14807 | 20066 | 9927 |
| consensus matched peptides | 315 | 399 | 95 | 212 | 285 | 768 | 732 | 2226 |
| Decoy hits | 0 | 0 | 0 | 1 | 0 | 3 | 6 | 3 |
| consensus non-decoy non-redundant peptides | 115 | 135 | 36 | 84 | 115 | 252 | 271 | 765 |
| peptides tested for immune responses identified by only one program | 18 | 12 | | | | | | |
| Immunogenic peptides | 1 | 1 | NYD | | NYD | | NYD | |
| Source proteins | 106 | 109 | 36 | 70 | 84 | 177 | 176 | 479 |
| Synovial fluid mononuclear cells, No. of | | | | | | | | |
| MS/MS spectra | | 13030[2] | | | 1000[3] | 5948[4] | 7307[4] | |
| spectrum-to-peptide matches | | 1380 | | | 120 | 350 | 162 | |
| consensus matched peptides | | 107 | | | 6 | 113 | 45 | |
| Decoy hits | | 0 | | | 0 | 0 | 0 | |
| consensus non-decoy non-redundant peptides | | 61 | | | 5 | 57 | 26 | |
| peptides tested for immune responses identified by only one program | | 10 | | | | | | |
| Immunogenic peptides | | 0 | | | NYD | | NYD | |
| Source proteins | | 49 | | | 5 | 40 | 22 | |
| Peripheral blood mononuclear cells, No. of | | | | | | | | |
| MS/MS spectra | | 26146[2] | 3616[4] | | | | | |
| spectrum-to-peptide matches | | 1381 | 161 | | | | | |
| consensus matched peptides | | 15 | 40 | | | | | |
| Decoy hits | | 0 | 0 | | | | | |
| consensus non-decoy non-redundant peptides | | 11 | 28 | | | | | |
| peptides tested for immune responses identified by only one program | | | | | | | | |
| Immunogenic peptides | | 0 | NYD | | | | | |
| Source proteins | | 9 | 12 | | | | | |

[1]LC-MS/MS data acquired with a Sciex QSTAR mass spectrometer;
[2]Thermo LTQ-Orbitrap XL mass spectrometer;
[3]Agilene 6550 Q-TOP mass spectrometer; and
[4]Thermo Q Exactive plus mass spectrometer
[Ω]Results from a second time immune purification from the tissue cell lysate.
N/A: not available; NYD: not yet done.

Number of Peptides and Source Proteins Identified from HLA-DR-Presented Self Peptides—Overall, 1,647 to 40,390 MS/MS spectra were generated per sample from the in vivo HLA-DR-presented peptides isolated from the 22 samples of ST, SFMC or PBMC from the 13 patients (Table 1). Using three different MS/MS spectra search engines (Mascot, OMSSA, and X!Tandem), 161 to 29,993 spectrum-to-peptide matches were obtained per sample. The peptides identified by consensus match (i.e., ≥two search programs) are reported in Table 1. The spectra for these peptides were manually inspected and given priority for inclusion in immunological assays; this number ranged from 2 to 2,363 peptides per sample. As noted in Table 1, expert manual inspection of peptide MS/MS spectra assigned with high scores by only a single program led to the addition of 90 peptides to the inclusion list for immunological assays.

At this stringency level, 59 to 801 non-decoy, non-redundant HLA-DR-presented self-peptides were identified in the 12 individual ST samples; these peptides were derived from 42 to 493 different source proteins (Table 1). Using this same methodology for the six SFMC and four PBMC samples, 2 to 71 non-redundant peptides derived from 2 to 49 source proteins were identified per patient from SFMC, and 7 to 34 non-redundant peptides derived from 7 to 24 source proteins were identified per patient from PBMC. The lengths of the MHC class II HLA-DR-presented peptides ranged from seven to 27 amino acids; the typical length of the peptides was 13-17 amino acids. Altogether, from all three sites, 1,593 non-redundant HLA-DR-presented, self-peptides were identified; these were derived from 870 source proteins.

In the translational component of the research, all non-redundant peptides were synthesized and tested for reactivity with the matching patient's PBMC. To date, this step has been completed for three patients with RA and five with LA (Table 1). One immunogenic HLA-DR-presented peptide was identified in ST from patient RA1, and one immunogenic peptide was identified in ST from patient RA2 (25, 26). In this patient, an additional peptide was also found in both ST and PBMC in three different analyses. Similarly, among the five LA patients, at least one unique immunogenic HLA-DR-presented peptide was identified in each of three patients (LA1, LA4, and LA5) (22-24). Four of the six immunogenic peptides were identified by consensus match, and two were identified by manual inspection of sequences identified by only one program.

Comparison of Results from Different LC-MS/MS Instruments in the Identification of HLA-DR-Presented Self Peptides—During the 7-year period of this study, newer high sensitivity LC-MS/MS instruments became available in the laboratory. Therefore, over the course of the study, HLA-DR-presented peptides samples were analyzed by four types of LC-MS/MS instruments (Table 2). The average numbers of unique-consensus peptides identified from LA or RA patients' ST was 239 using the QSTAR, 313 using the LTQ-Orbitrap XL, 571 using the 6550 Q-TOF, and 2,226 using the Q Exactive plus MS. The average numbers from patients' SFMC were 51 using the LTQ-Orbitrap XL, 6 using the 6550 Q-TOF, and 70 using the Q Exactive plus MS. From patients' PBMC, the average numbers were 15 using the LTQ-Orbitrap XL, and 50 using the Q Exactive plus MS. Thus, as the sensitivity and data handling capacity of the LC-MS/MS instruments improved during the study, the number of identified HLA-DR-presented peptides steadily increased.

TABLE 2

Comparison of the spectra generated and identified by the four different mass spectrometers.

|  | Synovial tissue | Synovial fluid | Peripheral blood |
| --- | --- | --- | --- |
| QSTAR | N = 4* |  |  |
| # MS/MS spectra† | 1815 |  |  |
| # spectrum-to-peptide matches | 1033 |  |  |
| # consensus matched peptides | 239 |  |  |
| # Decoy hits | 0 |  |  |
| # non-decoy non-redundant peptides | 95 |  |  |
| # Source Proteins | 70 |  |  |
| LTQ-Orbitrap XL | N = 7 | N = 4 | N = 3 |
| # MS/MS spectra | 9756 | 16106 | 19379 |
| # spectrum-to-peptide matches | 2246 | 1670 | 1498 |
| # consensus matched peptides | 313 | 51 | 15 |
| # Decoy hits | 0 | 0 | 0 |
| # non-decoy non-redundant peptides | 121 | 31 | 11 |
| # Source Proteins | 93 | 24 | 9 |
| 6550 iFunnel Q-TOF | N = 3 | N = 1 |  |
| # MS/MS spectra | 19633 | 1000 |  |
| # spectrum-to-peptide matches | 13106 | 120 |  |
| # consensus matched peptides | 571 | 6 |  |
| # Decoy hits | 3 | 0 |  |
| # non-decoy non-redundant peptides | 202 | 5 |  |
| # Source Proteins | 141 | 5 |  |
| Q Exactive plus | N = 1 | N = 3 | N = 2 |
| # MS/MS spectra | 10936 | 6125 | 4922 |
| # spectrum-to-peptide matches | 9927 | 255 | 267 |
| # consensus matched peptides | 2226 | 70 | 50 |
| # Decoy hits | 3 | 0 | 0 |
| # non-decoy non-redundant peptides | 765 | 33 | 30 |
| # Source Proteins | 479 | 28 | 18 |

*Number of different samples analyzed. Only data for the first pass analysis are included.
†All numbers given indicate the average number of spectra identified based upon the number of samples analyzed.

Figure 1C:
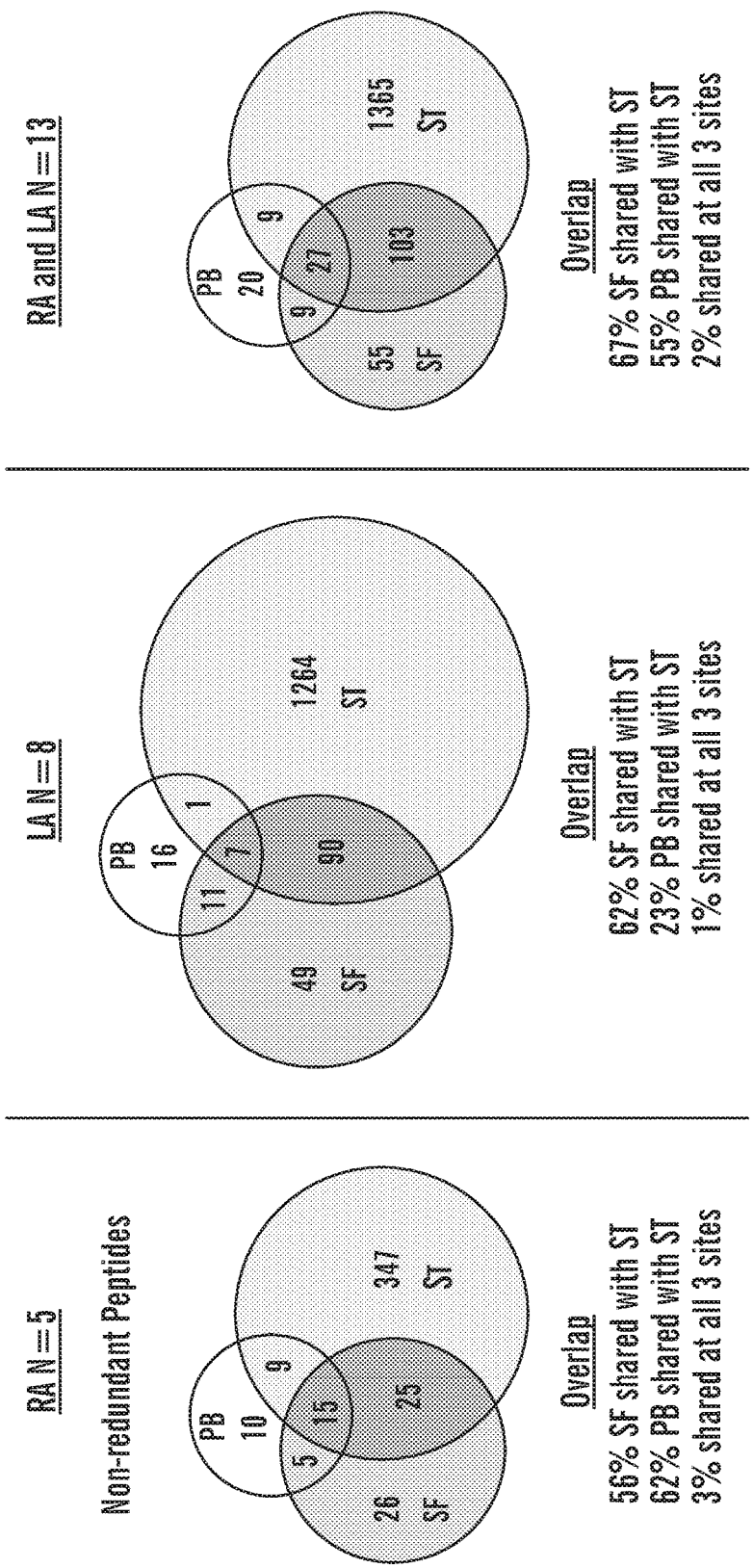

Comparison of HLA-DR-presented Peptides and Source Protein Repertoires in ST, SFMC, and PBMC—The identified HLA-DR-presented peptides from ST of RA1, RA2, LA1, and LA2 using IPI database were showed in reference (30). Since the SFMC sample from LA2, and SFMC and PBMC samples from RA2 were analyzed in this study, the original data from the four previous samples, which were reanalyzed using UniProt database, were included herein for comparison of the HLA-DR-presented peptides repertoires found in the three sample sites now being analyzed. In one patient each with RA or LA (RA2 and LA5), samples were available from all three compartments (ST, SFMC and PBMC), and this allowed for the degree of overlap in peptide presentation among these three sites to be determined for each of these patients (FIG. 1A). For patient RA2, 53% of the HLA-DR-presented peptides identified in SFMC and 53% of those found in PBMC were shared with those in ST, but only 6% were identified at all three sites. Analysis of the source proteins from which the peptides were derived gave similar frequencies (FIG. 1B). In comparison, patient LA5 had a smaller percentage of peptides shared between SFMC and ST (21%) than between PBMC and ST (36%), and the degree of overlap of source proteins between SFMC and ST (16%) was similar between PBMC and ST (22%). When the degree of overlap was compared between pairs of sample types available from the five RA patients or eight LA patients, a similar picture was found. In general, more than half of the peptides identified in SFMC were also found in ST (FIG. 1C). In RA, about half of the peptides identified in PBMC were also found in ST, whereas in LA, in which many more peptides were identified in ST, only about one-quarter of the PBMC peptides were also found in ST. There was a trend toward a lower percentage of source proteins than peptides being the same in SFMC or PBMC as in ST (FIG. 1D). Thus, in both diseases, HLA-DR-presented peptides in SFMC or PBMC provided some reflection of the peptides presented in ST, but also revealed additional peptides.

Source Proteins for HLA-DR-presented Peptides—The complete lists of consensus peptides were identified by at least two search engines from each site for each patient and the non-redundant HLA-DR-presented peptides and their source proteins were identified as described in methods. The most common source proteins of peptides from ST that were found in at least four patients, regardless of disease, are listed in alphabetical order in Table 3. These peptides (in order of frequency) were derived from cathepsin S, collagen α-1(I) chain, syntenin-1, serine carboxypeptidase CPVL (probable), albumin, pro-low-density lipoprotein receptor-related protein 1, apolipoprotein A2, complement C3, cytochrome c oxidase subunit 5B (mitochondrial), filamin-A, monocyte differentiation antigen CD14, and stromelysin-1. Since fewer SFMC and PBMC samples were analyzed, the list from these sites shows the source proteins identified in at least two patients rather than four patients. In SFMC, the list included keratin (type II cytoskeletal 1) and nuclease-sensitive element-binding protein 1. Keratin was commonly identified in both SFMC and PBMC. Because of the keratin type and the fact that the samples were not subjected to proteolysis during processing, it is unlikely that these peptides were sample-handling artifacts.

TABLE 3

The most abundant source proteins for the identified HLA-DR-presented peptides from three sites in RA and LA patients.

| Protein Name | Accession | RA# | LA# | Protein Name | Accession | RA# | LA# |
|---|---|---|---|---|---|---|---|
| Synovial tissue* | | | | | | | |
| Albumin | P02768 | 2 | 5 | Filamin-A | P21333 | 2 | 4 |
| Alpha-1B-glycoprotein | P04217 | 1 | 3 | Fructose-bisphosphate aldolase A | P04075 | 2 | 2 |
| Alpha-2-macroglobulin | P01023 | 2 | 3 | Hemopexin | P02790 | 1 | 3 |
| Alpha-enolase | P06733 | 1 | 3 | HLA class I histocompatibility antigen, A-2 alpha chain | P01892 | 2 | 2 |
| Angiotensinogen | P01019 | 1 | 3 | Inter-alpha-trypsin inhibitor heavy chain H4 | Q14624 | 1 | 3 |
| Annexin A2 | P07355 | 1 | 3 | Legumain | Q99538 | 1 | 3 |
| Apolipoprotein A-II | P02652 | 3 | 3 | Lysosome-associated membrane glycoprotein 1 | P11279 | 0 | 4 |
| C4b-binding protein alpha chain | P04003 | 1 | 3 | Macrophage mannose receptor 1 | Q5VSK2 | 1 | 3 |
| Calreticulin | P27797 | 1 | 3 | Monocyte differentiation antigen CD14 | P08571 | 2 | 4 |
| Cathepsin S | P25774 | 3 | 5 | Olfactomedin-like protein 2B | Q68BL8 | 0 | 4 |
| Caveolin-1 | Q03135 | 1 | 3 | Perilipin-3 | O60664 | 0 | 4 |
| Chondroadherin | O15335 | 1 | 3 | Phosphatidylcholine-sterol acyltransferase | P04180 | 2 | 2 |
| Coagulation factor XIII A chain | P00488 | 2 | 2 | Phosphoglycerate kinase 1 | P00558 | 3 | 1 |
| Cofilin-1 | P23528 | 2 | 3 | Plexin domain-containing protein 2 | Q6UX71 | 3 | 2 |
| Collagen alpha-1(I) chain | P02452 | 3 | 5 | Profilin-1 | P07737 | 2 | 3 |
| Collagen alpha-1(XI) chain | P12107 | 2 | 2 | Prolow-density lipoprotein receptor-related protein 1 | Q07954 | 3 | 4 |
| Collagen alpha-2(I) chain | P08123 | 2 | 3 | Proteoglycan 4 | Q92954 | 1 | 3 |
| Collagen alpha-2(V) chain | P05997 | 2 | 3 | Rho GDP-dissociation inhibitor 2 | P62566 | 1 | 4 |
| Complement C1q subcomponent subunit 8 | P02746 | 0 | 4 | 60S ribosomal protein L30 | P52888 | 3 | 1 |
| Complement C1s subcomponent | P09871 | 1 | 4 | 60S ribosomal protein L6 | Q02878 | 2 | 2 |
| Complement C3 | P01024 | 3 | 3 | Serine carboxypeptidase CPVL (probable) | O9H3G5 | 3 | 4 |
| Complement C5 | P01031 | 1 | 4 | SPARC-like protein 1 | Q14515 | 0 | 4 |
| C-reactive protein | P02741 | 2 | 3 | Stabilin-1 | Q9NY15 | 2 | 3 |
| Cytochrome c oxidase subunit 5B, mitochondrial | P10606 | 2 | 4 | Stromelysin-1 | P06254 | 2 | 4 |
| Cytochrome c oxidase subunit 8A, mitochondrial | P10176 | 2 | 2 | Syntenin-1 | O00560 | 2 | 6 |
| Decorin | P07585 | 1 | 4 | Talin-1 | Q9Y490 | 0 | 5 |
| Epididymal secretory protein E1 | P61916 | 1 | 3 | Vascular cell adhesion protein 1 | P19320 | 0 | 4 |
| ER-Golgi intermediate compartment protein 1 | Q969X5 | 1 | 3 | Vitronectin | P04004 | 2 | 3 |
| Fibrinogen beta chain | P02675 | 3 | 2 | | | | |
| Synovial fluid† | | | | | | | |
| Albumin | P02768 | 1 | 1 | Keratin, type I cytoskeletal 9 | P35527 | 1 | 1 |
| Alpha-2-macroglobulin | P01023 | 1 | 1 | Keratin, type II cytoskeletal 1 | P04264 | 1 | 2 |
| Annexin A6 | P08133 | 1 | 1 | Lysosomal alpha-mannosidase | O00754 | 1 | 1 |
| C4b-binding protein alpha chain | P04003 | 1 | 1 | MHC class I antigen | P01889 | 1 | 1 |
| Cathepsin S | P25774 | 1 | 1 | MHC class II antigen | P04229 | 1 | 1 |
| Cofilin-1 | P23528 | 1 | 1 | Nuclease-sensitive element-binding protein 1 | P67809 | 1 | 2 |
| Complement C3 | P01024 | 1 | 1 | Plasminogen | P00747 | 1 | 1 |
| Fibrinogen alpha chain | P02671 | 1 | 1 | Plexin domain-containing protein 2 | Q6UX71 | 1 | 1 |
| Ficolin-1 | O00602 | 0 | 2 | Stromelysin-1 | P08254 | 1 | 1 |
| Glutathione S-transferase P | P09211 | 1 | 1 | T-cell surface glycoprotein CD4 | P01730 | 1 | 1 |
| Hemoglobin subunit alpha | P69905 | 1 | 1 | Toll-like receptor 2 | O60603 | 1 | 1 |
| Histone H1 | Q02539 | 0 | 2 | | | | |

TABLE 3-continued

The most abundant source proteins for the identified HLA-DR-presented peptides from three sites in RA and LA patients.

| Protein Name | Accession | RA# | LA# | Protein Name | Accession | RA# | LA# |
|---|---|---|---|---|---|---|---|
| Peripheral Blood‡ | | | | | | | |
| Alpha-1-antitrypsin | P01009 | 0 | 2 | Keratin, type I cytoskeletal 9 | P35527 | 1 | 2 |
| Inter-alpha-trypsin inhibitor heavy chain H4 | Q14624 | 1 | 1 | Keratin, type II cytoskelelal 1 | P04264 | 1 | 1 |
| Keratin, type I cytoskeletal 10 | P13645 | 1 | 1 | Nuclease-sensitive element-binding protein 1 | P67809 | 1 | 1 |

The numbers in "RA#" and "LA#" columns indicate the number of patients from whom each source protein was identified.
*Source proteins identified in ST in at least four of the twelve patients.
†Source proteins identified in SF in at least two of the six patients tested.
‡Source proteins identified in PB in at least two of the four patients tested.

In most RA patients, the identified HLA-DR-presented peptides were derived from source proteins that are thought to serve as potential autoantigens in RA. These included cartilage glycoprotein 39, various types of collagen, enolase, fibrinogen, fibronectin, immunoglobulin, and vimentin (Table 4). Interestingly, HLA-DR-presented peptides from these source proteins were also commonly identified in patients with LA.

TABLE 4

Source proteins found both in RA and LA that are known or proposed to serve as autoantigens in RA*

| | Rheumatoid Arthritis Patient | Lyme Arthritis Patient |
|---|---|---|
| Cartilage glycoprotein 39 | RA2 | LA1/LA8 |
| Collagen- type I, a-1 | RA1/RA3 | LA3/LA5/LA6/LA7/LA8 |
| type I, a-2 | RA2†/RA3 | LA3/LA5/LA8 |
| type IV, a-1 | | LA8 |
| type V, a-1 | RA5 | LA3/LA8 |
| typeV, a-2 | RA2/RA3 | LA5/LA7/LA8 |
| type VI, a-1 | | LA8 |
| type VI, a-3 | RA3 | LA3/LA5/LA7/LA8 |
| type XI, a-1 | RA2/RA3 | LA5/LA8 |
| type XII, a-1 | RA3/RA5 | LA1/LA5/LA8 |
| type XIV, a-1 | RA2 | LA3/LA4/LA5/LA6/LA7/LA8 |
| type XV, a-1 | RA3 | LA7/LA8 |
| Enolase | RA4‡/RA5 | LA2/LA5†/LA6/LA7/LA8 |
| Fibrinogen - alpha | RA2†/RA3/RA5 | LA3/LA4/LA5/LA7†/LA8† |
| beta | RA2/RA3/RA5 | LA1/LA4/LA6/LA7‡/LA8 |
| gamma | RA2Ŧ/RA3/RA4‡ | LA2/LA4/LA5/LA7†/LA8 |
| Fibronectin | RA1/RA2/RA3/RA5 | LA1/LA2/LA3/LA4/LA5/LA6/LA7†/LA8 |
| Immunoglobulin | RA2/RA3 | LA1/LA3/LA4/LA8 |
| Vimentin | RA1/RA2/RA3/RA5 | LA1/LA3/LA7/LA8† |

*Unless marked otherwise, peptides from these source proteins were identified only in synovial tissue.
†Peptide(s) from this source protein identified in synovial tissue and synovial fluid
‡Peptide(s) from this source protein identified only in synovial fluid
Ŧ Peptide(s) from this source protein identified in synovial tissue, synovial fluid, and peripheral blood Search for citrullinated HLA-DR-presented peptides—Protein citrullination is considered to be an important post-translational modification in RA. The strong association between RA shared-epitope alleles and ACPA-positive RA has been hypothesized to result from the binding and presentation of citrullinated peptides by HLA-DR molecules (11). Therefore, the MS/MS spectra were searched carefully for evidence of this post-translational modification, which results in the gain of 0.984 D (NH2 vs. OH) when arginine is converted to citrulline. The search algorithms assigned several observed MS/MS spectra that had incomplete fragment ion series to citrullinated peptides. However, in each case, manual inspection and targeted tandem mass spectrometry yielded full sequence information that unambiguously defined that the peptide modification actually corresponded to hydrolysis of asparagine to aspartic acid or glutamine to glutamic acid.

Figure 2A:
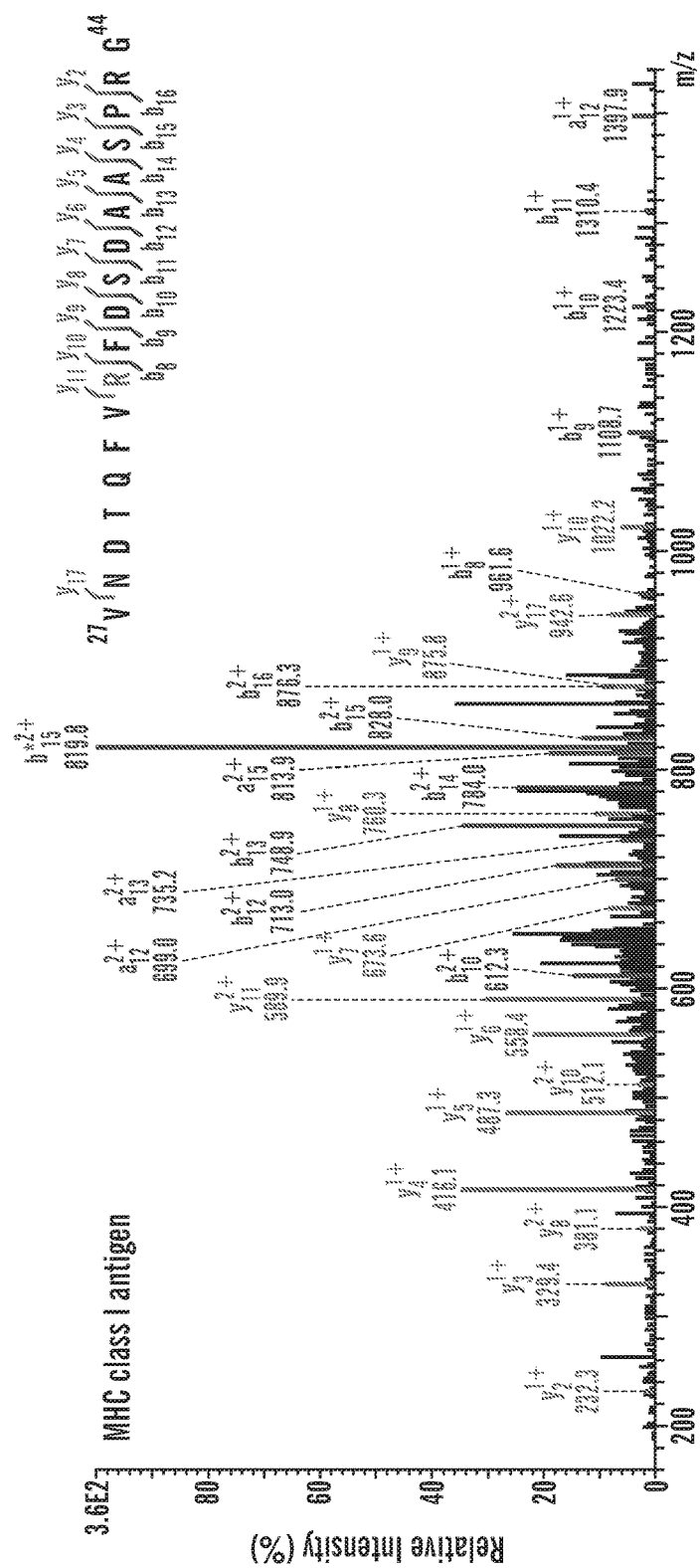
FIGS. 2A-2B show high abundance, high accuracy peptide fragment ions can provide full sequence coverage and clearly distinguish asparagine deamidation from arginine citrullination.
Figure 2B:
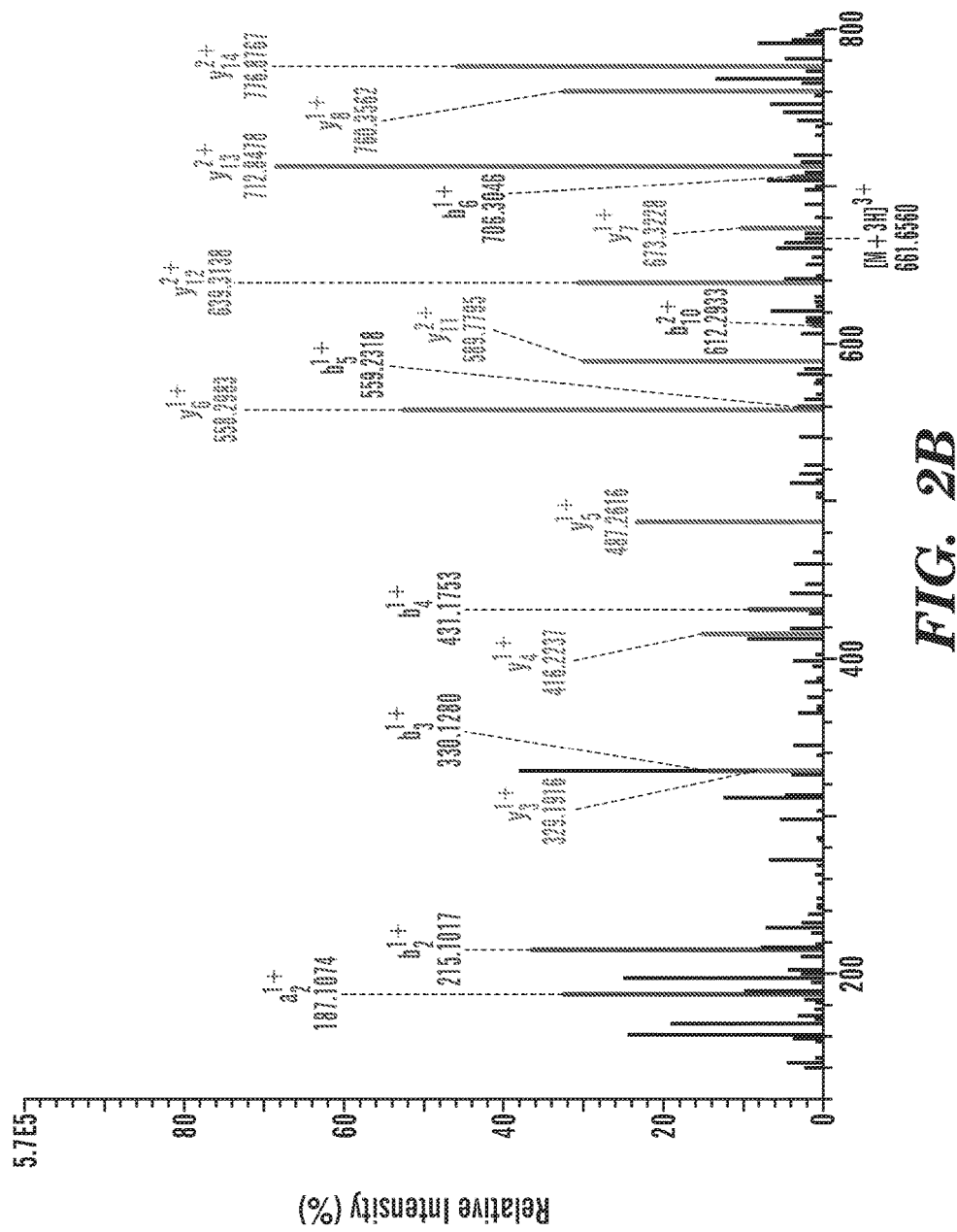
Figure 2B:
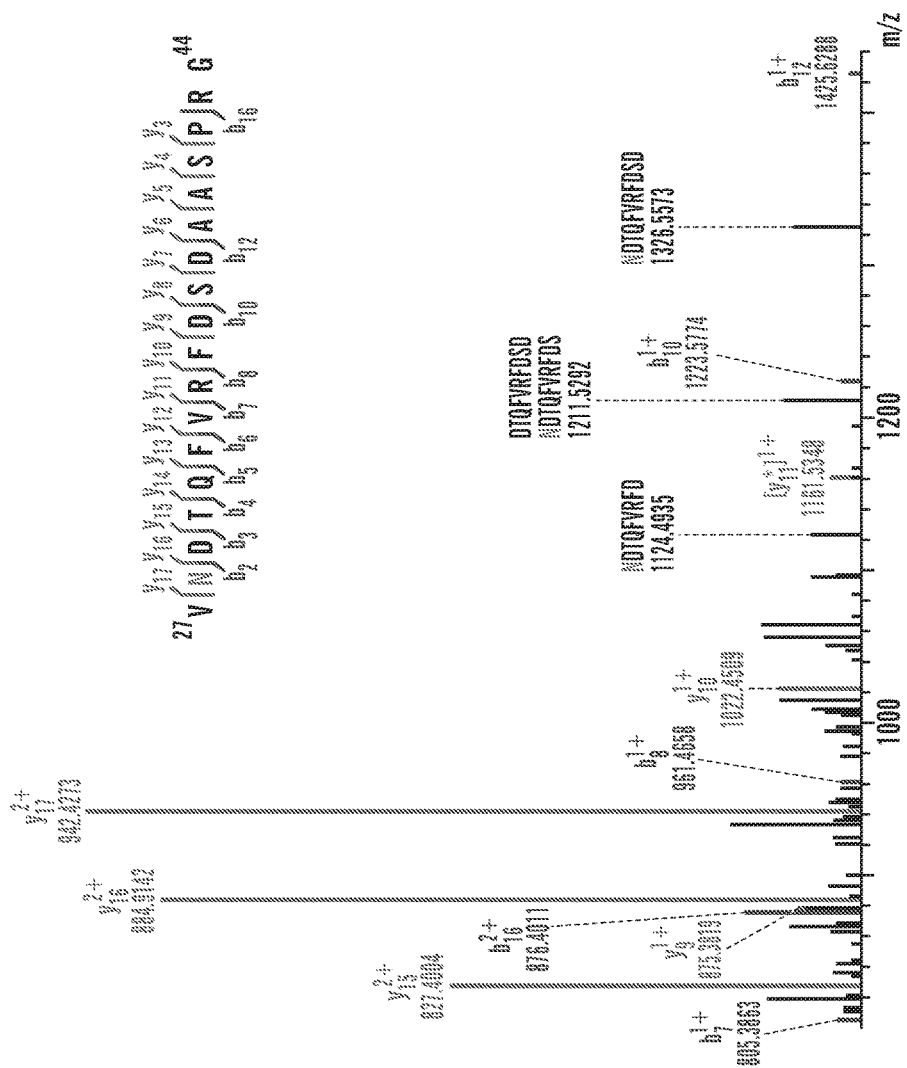
Figure 3A:
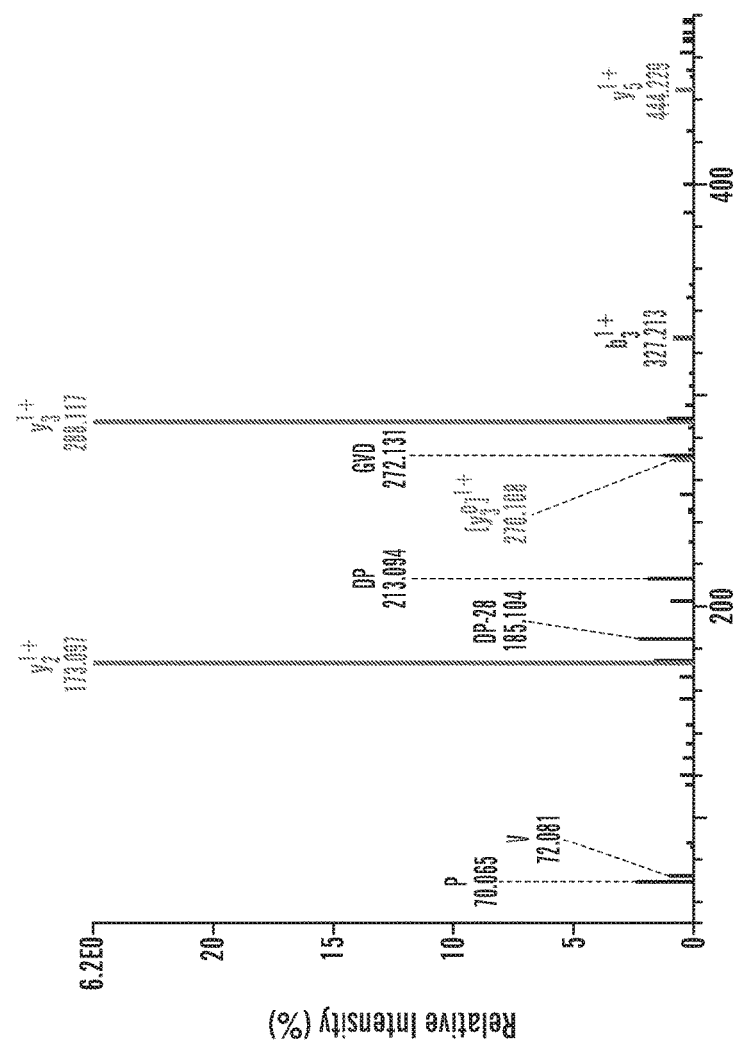
FIGS. 3A-3F show Tandem mass spectra for HLA-DR-presented peptides identified to be immunogenic in patients with RA or LA.
Figure 3A:
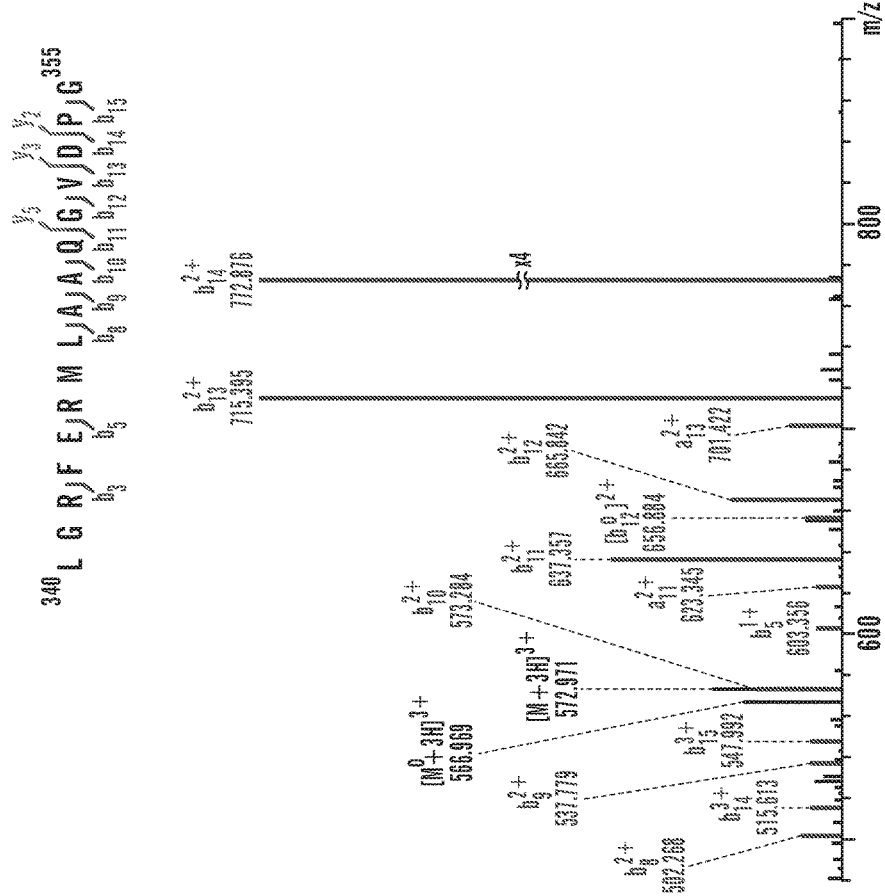
Figure 3B:
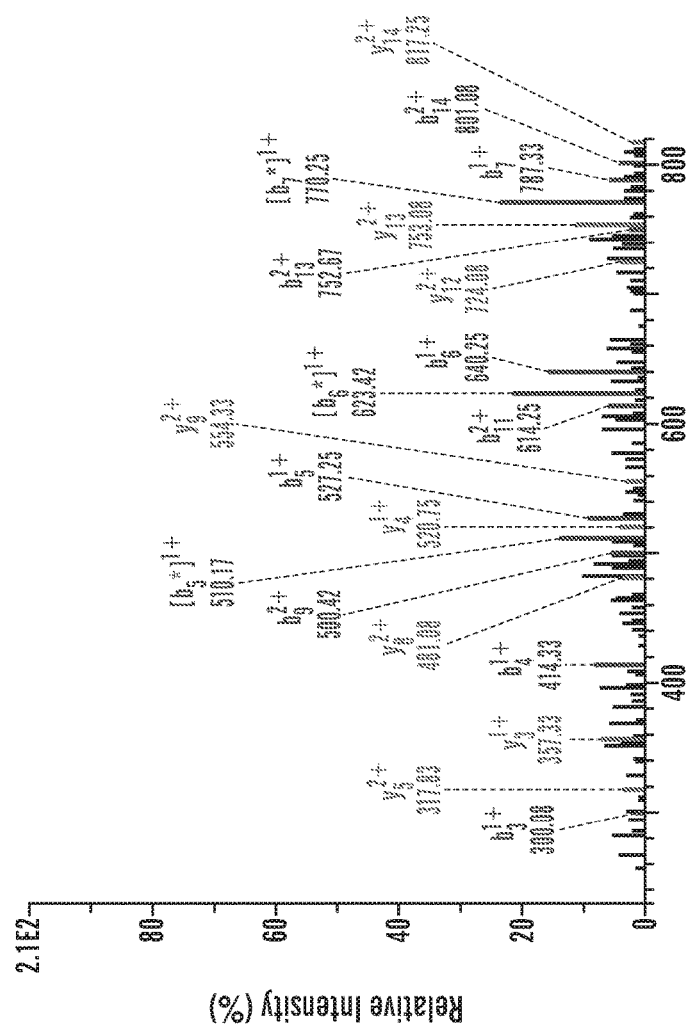
Figure 3B:
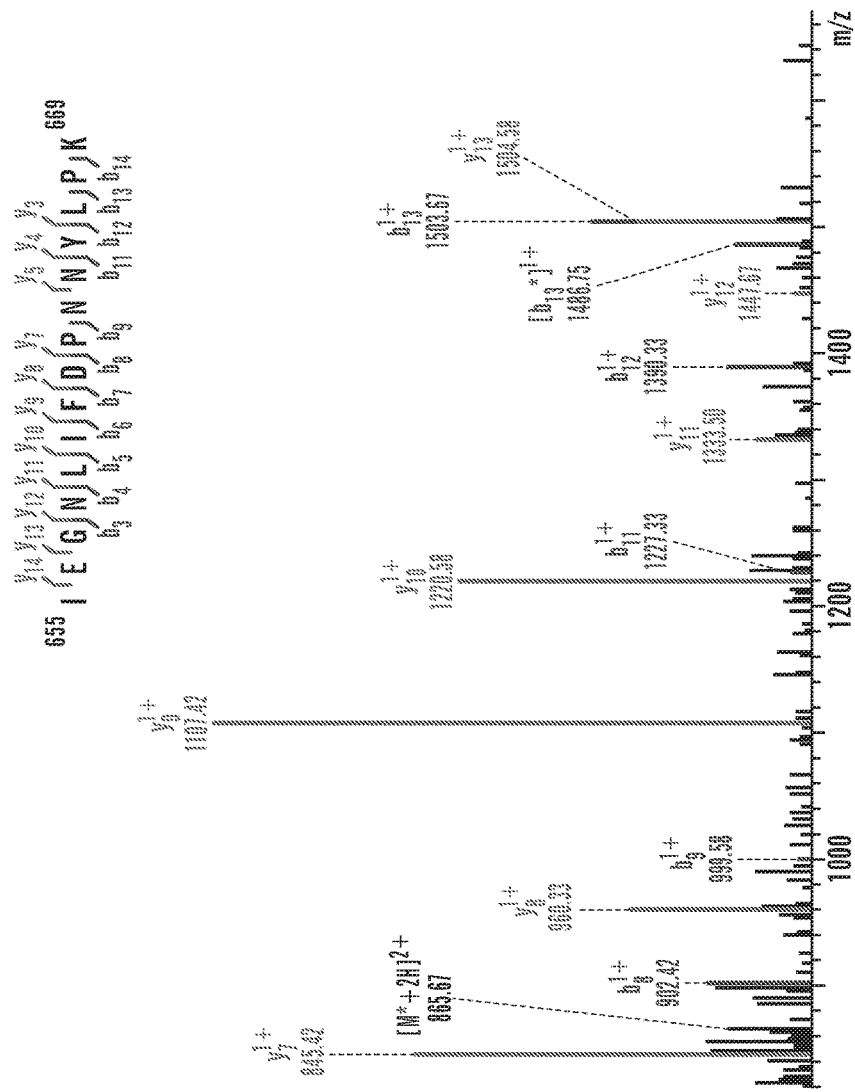
Figure 3C:
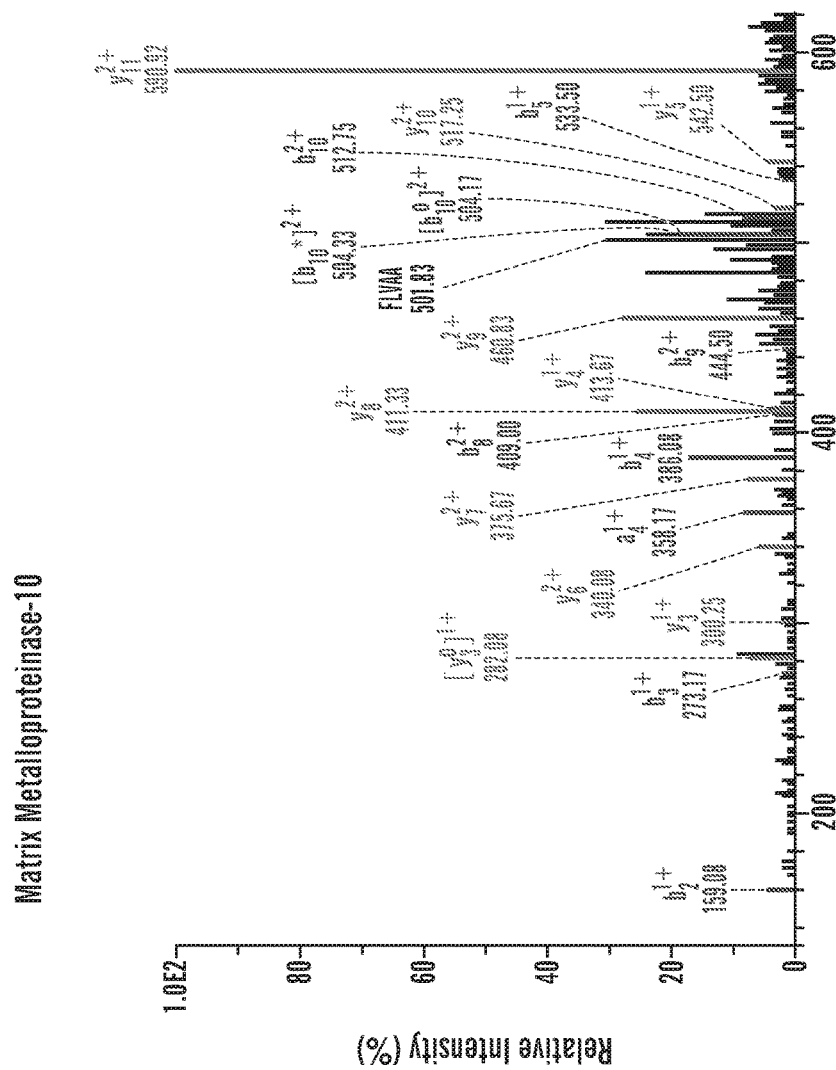
Figure 3C:
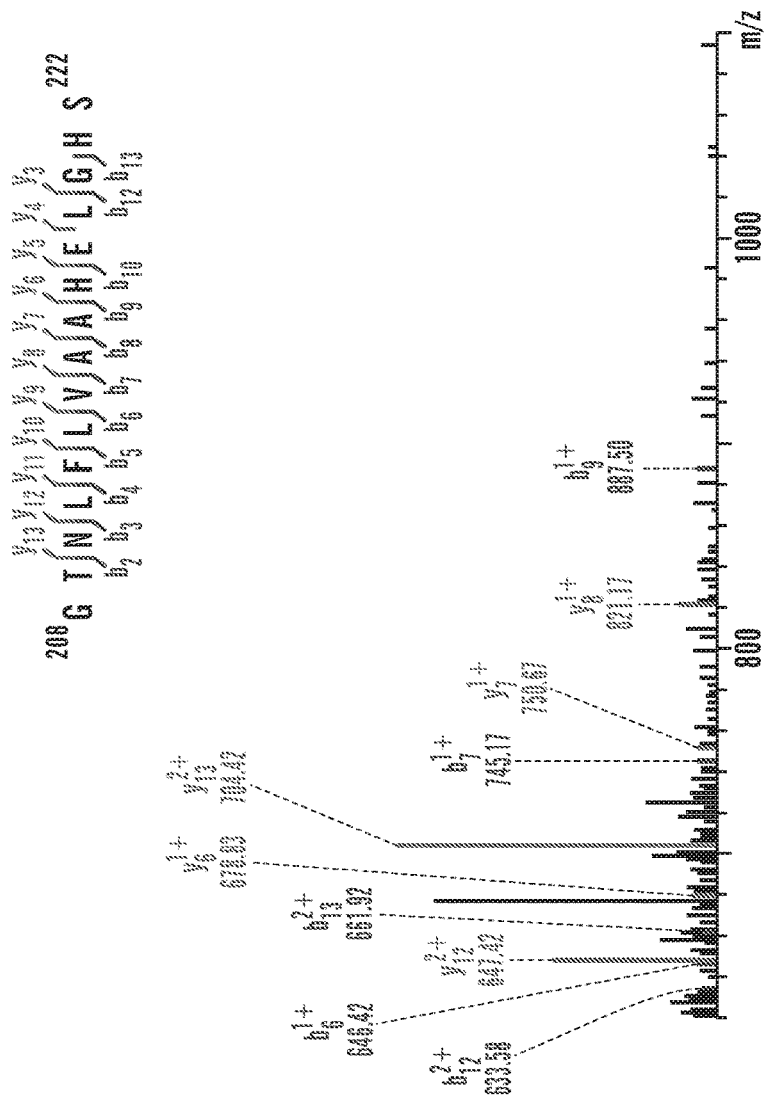
Figure 3D:
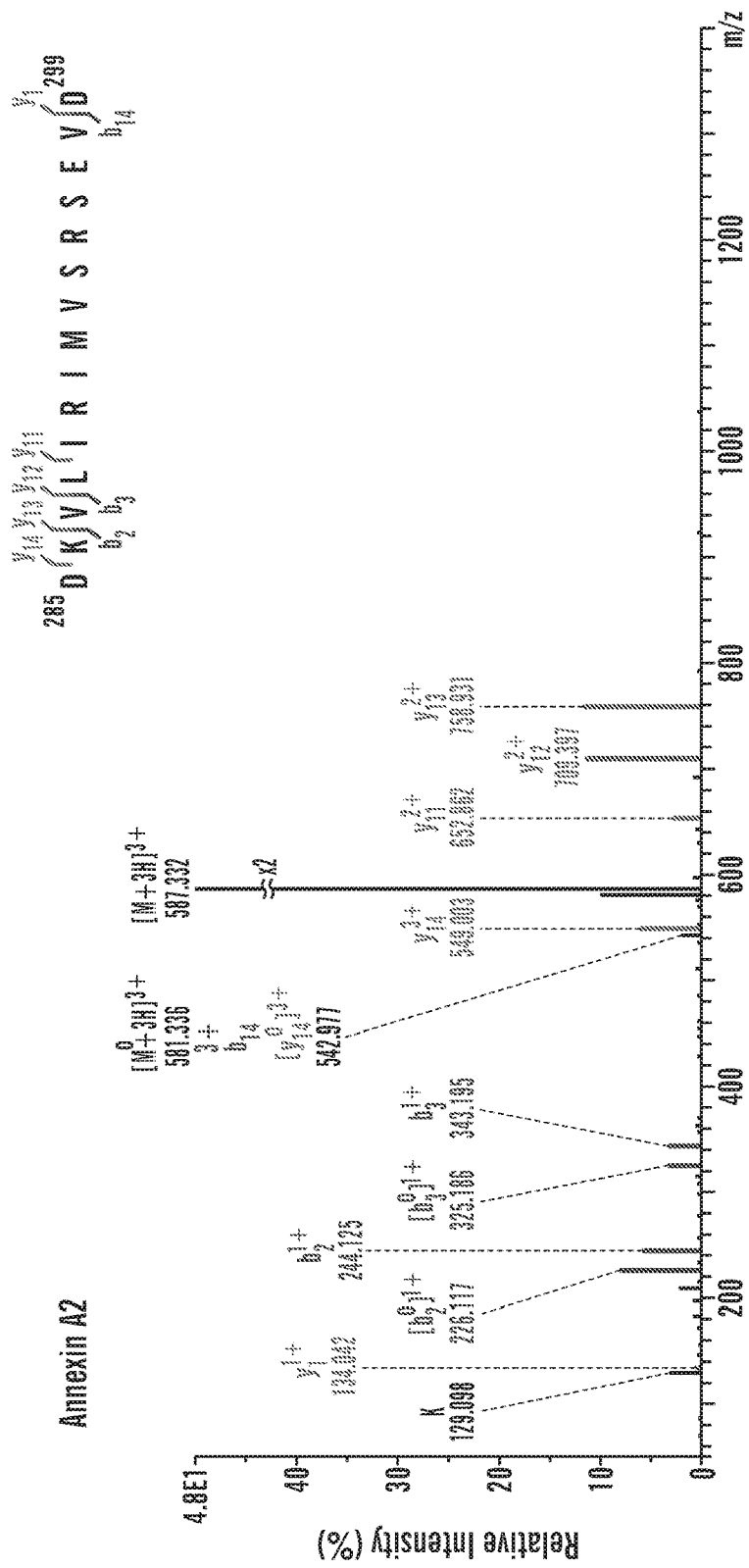
Figure 3E:
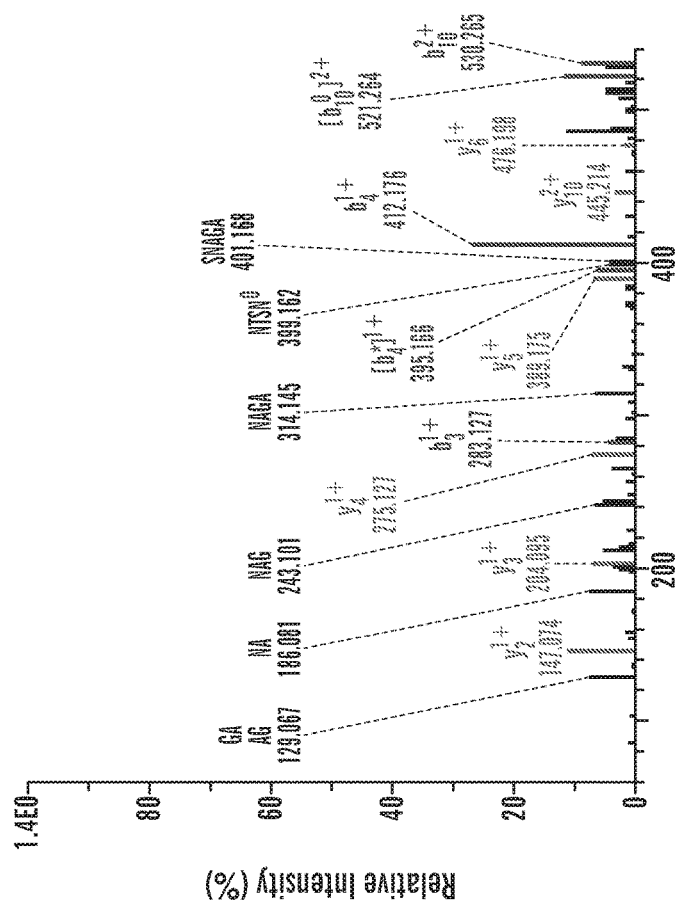
Figure 3E:
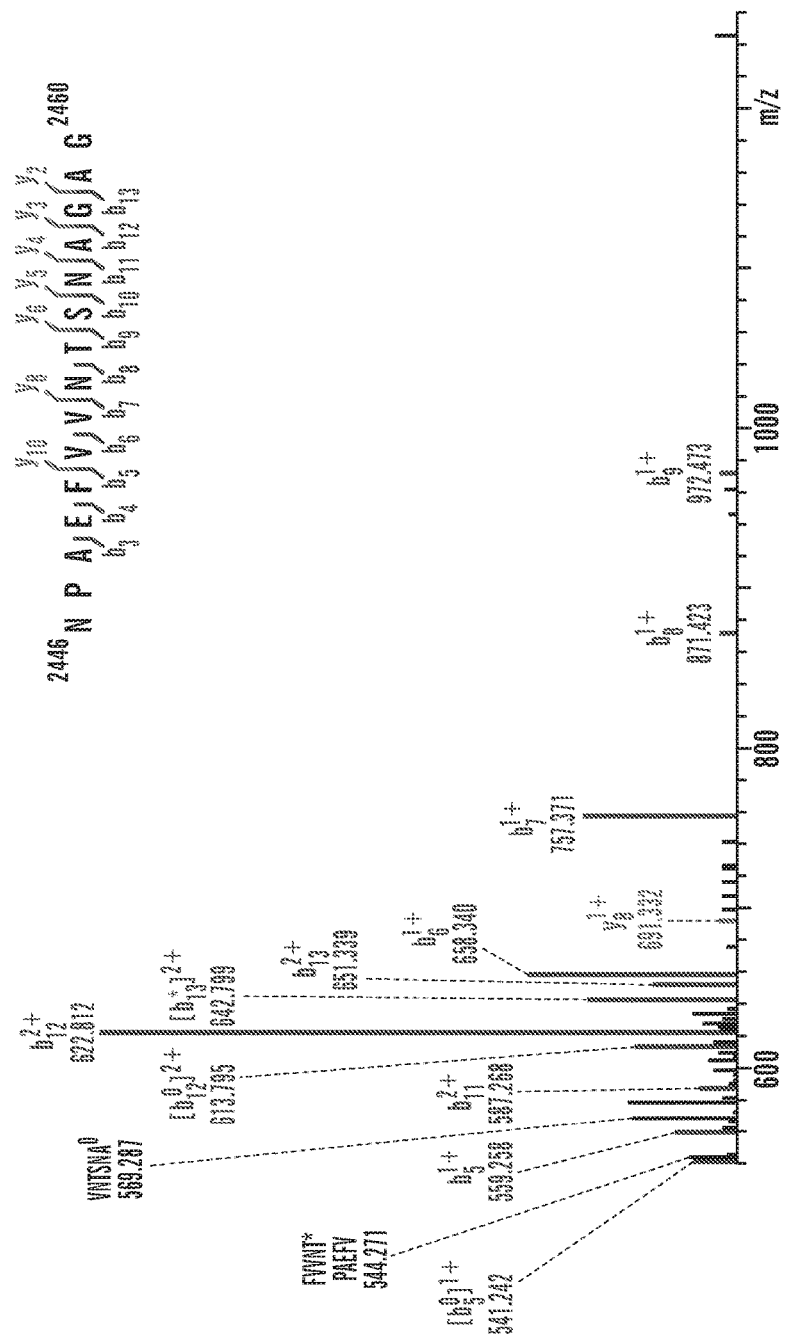
Figure 3F:
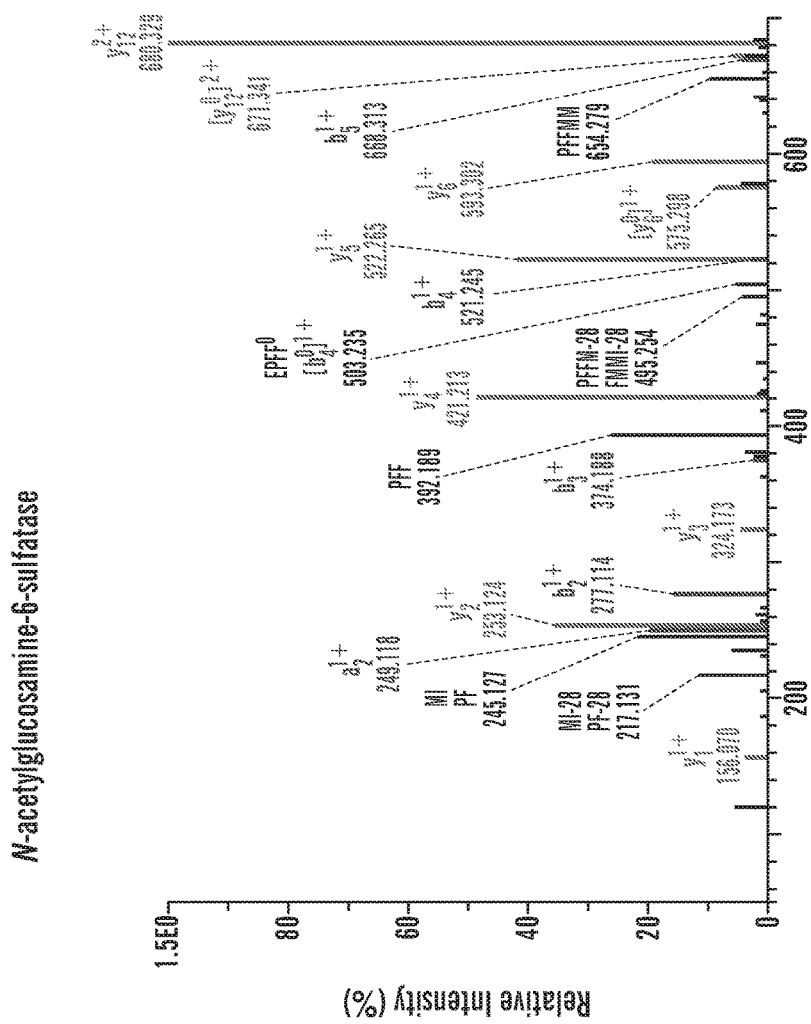
Figure 3F:
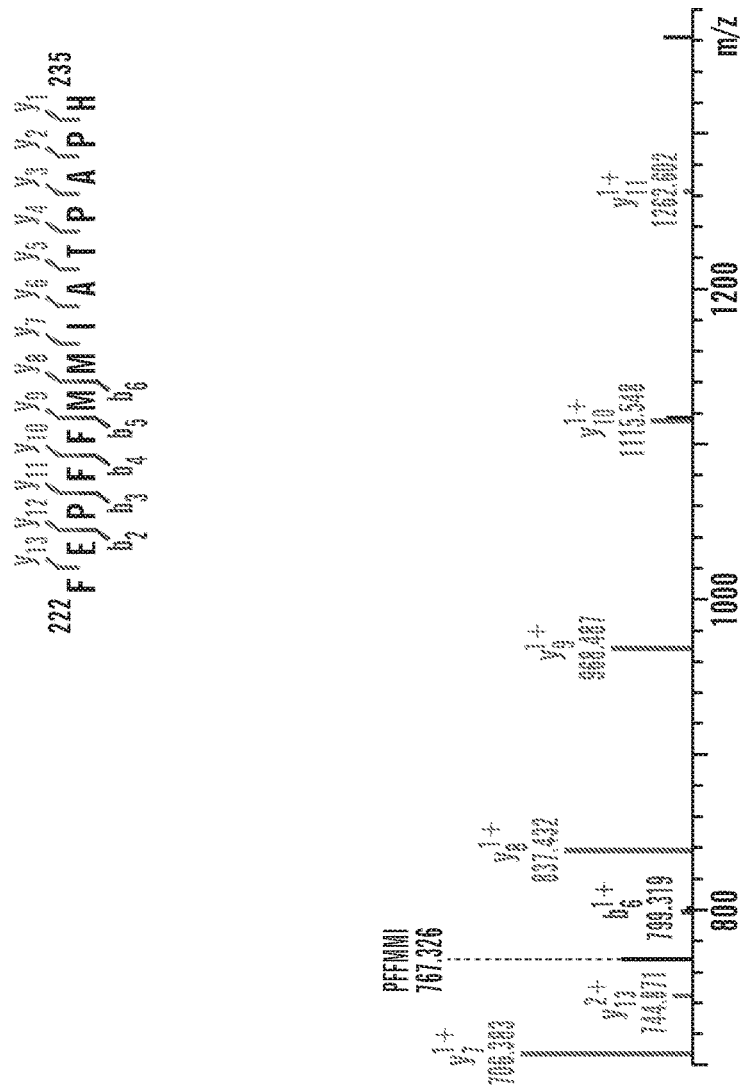
Figures 5A, 5B:
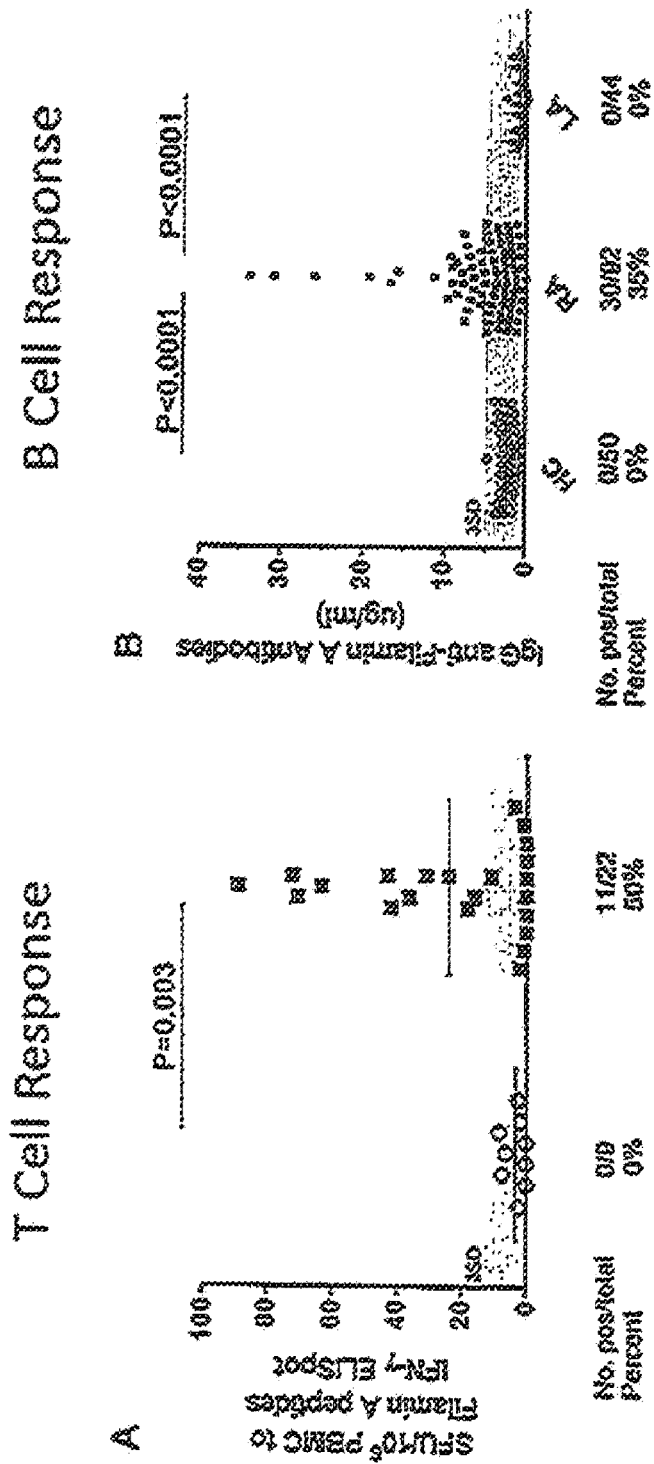
FIGS. 5A-5B are plots showing T and B cell autoreactivity to Filamin A.
Figures 6A, 6B:
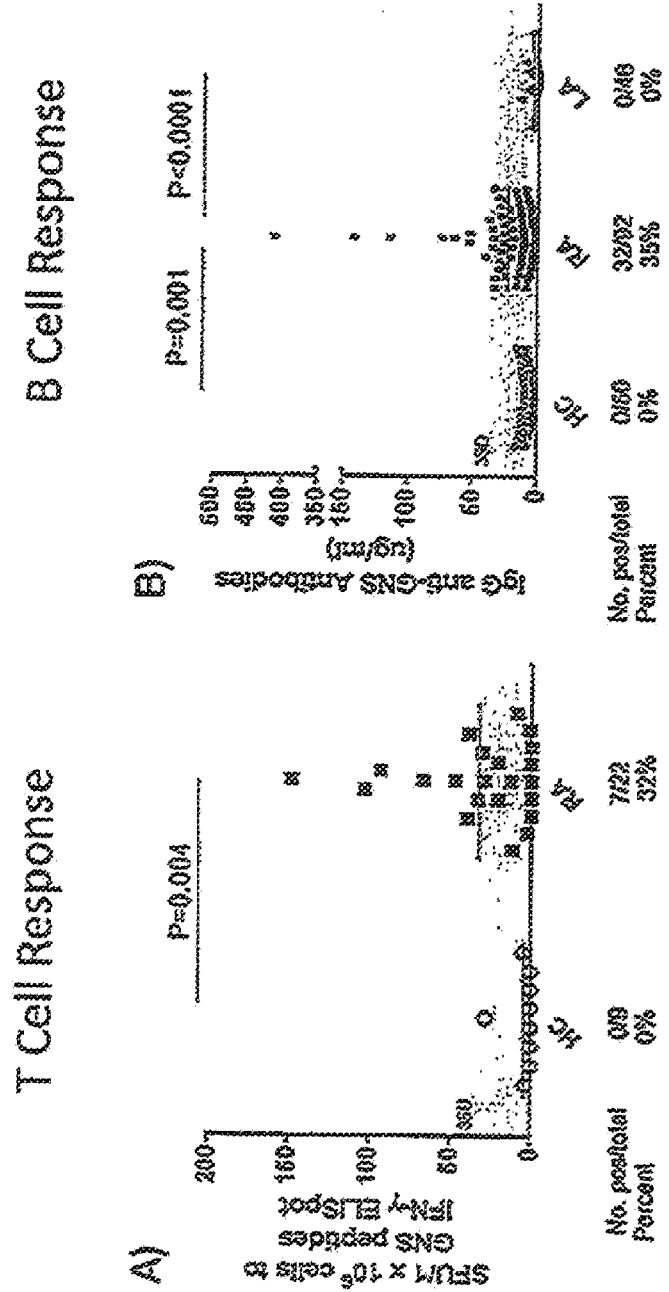
FIGS. 6A-6B are plots showing T and B cell autoreactivity to N-acetylglucosamine-6-sulfatase.
Figure 7:
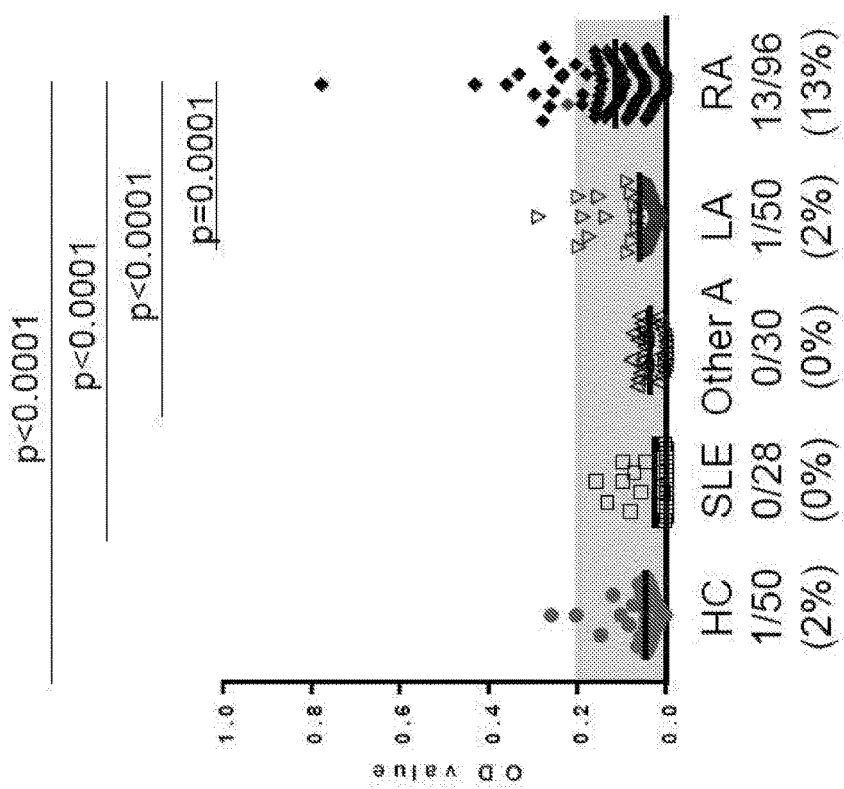
FIG. 7 shows serum levels of GNS protein determined by sandwich ELISA. Positivity was calculated as >3SD above the mean of normal control (area above the shaded region). HC, healthy control; SLE, systemic lupus; Other A, psoriatic arthritis, ankylosing spondylitis, osteoarthritis; LA, Lyme arthritis; RA, rheumatoid arthritis. 13% of RA patients had high serum GNS protein levels.
Figure 8:
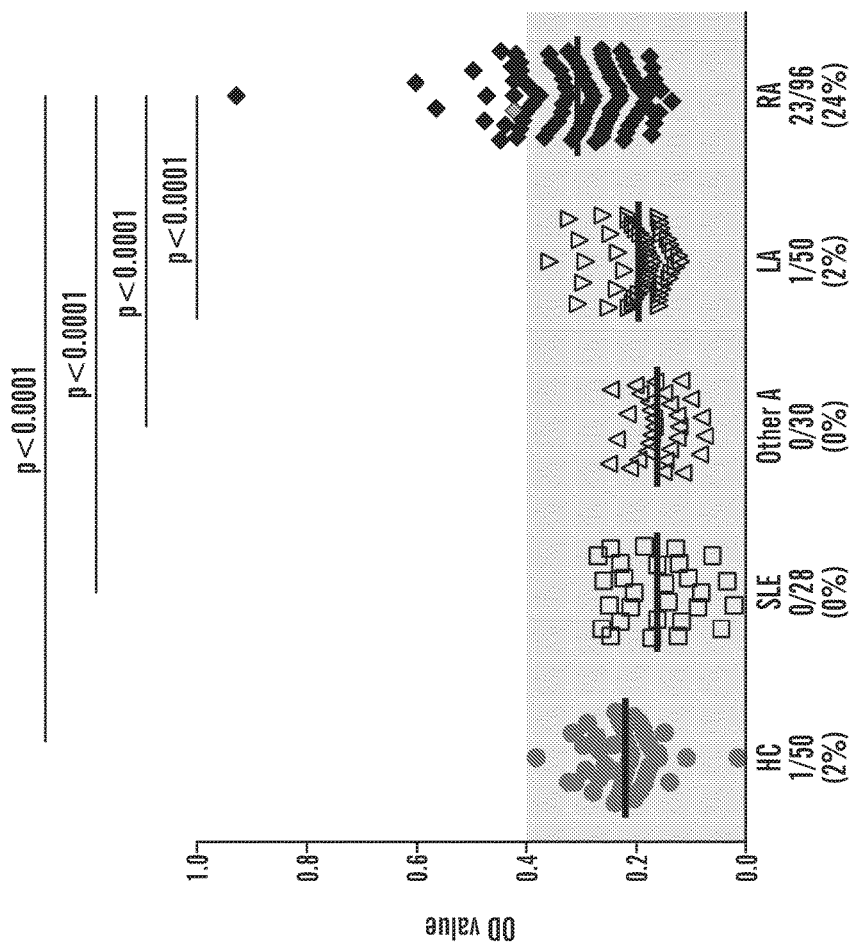
FIG. 8 shows serum levels of filamin A protein determined by sandwich ELISA. Positivity was calculated as >3SD above the mean of normal control (area above the shaded region). HC, healthy control; SLE, systemic lupus; Other A, psoriatic arthritis, ankylosing spondylitis, osteoarthritis; LA, Lyme arthritis; RA, rheumatoid arthritis. 24% of RA patients had high serum filamin A protein levels.

For example, arginine conversion to citrulline at R8 of the peptide VNDTQFVRFDSDAASPRG (SEQ ID NO: 5), that corresponds to residues 27 to 44 in the source protein B6V6K3 MHC class I antigen (fragment), which was originally detected in the ST of patient RA3, was assigned as the citrullinated peptide by two protein database search programs during analysis of LC-MS/MS data acquired on the LTQ-Orbitrap XL MS. However, since conversion of arginine to citrulline and hydrolysis of asparagine to aspartic acid result in the same change in elemental composition and thus to the same peptide mass shift, the molecular weight change and partial sequence coverage should not be considered definitive. In this case, the signal for the MS/MS spectrum shown in FIG. 2A was recorded using the low resolution ion trap of the LTQ-Orbitrap XL MS; the series of sequence-determining fragment ions was incomplete and left room for ambiguity. The fragment ion at m/z 589.9 matches both the y11 ions of arginine to citrulline modification and hydrolysis of asparagine to aspartic acid modification within 0.5 Da error tolerances. Therefore, despite the agreement of the two database searches, it was really not possible to distinguish between these two post-translational modifications on the basis of these data. Later, when we had the opportunity to apply targeted tandem MS on the Q Exactive plus MS, the full series of high accuracy, high abundance diagnostic fragment ions allowed unambiguous assignment of the modification as asparagine deamidation at N2 (FIG. 2B). Similar results were obtained for each of the other tentative assignments of citrullination that had been based on low resolution MS/MS spectra containing incomplete ion series.

Identification of Immunogenic peptides and source proteins—In five of the eight patients for whom sample testing have been completed, one to two immunogenic peptides (T cell epitopes) were identified from the peptides identified from each patient. When these peptides or their source proteins were tested for reactivity with PBMC or serum samples from many patients, it was found that 10-50% of RA or LA patients had T and/or B cell reactivity with each immunogenic peptide or its source protein. The immunological data and key MS/MS data for each individual autoantigen have been shown in references (22-26), the contents of which are incorporated herein in their entireties. Here, in an effort to integrate and make available the full mass spectrometry dataset, presented are complete list of peptides identified from each patient that correspond to assignments indicated on the MS/MS spectra. The peptides found to be immunogenic were derived from the source proteins endothelial cell growth factor (ECGF) (22), apolipoprotein B-100 (apoB-100) (23), matrix metalloproteinase-10 (MMP-10) (24) in LA; from annexin A2 in both RA and LA (25) and from N-acetylglucosamine-6-sulfatase and filamin A in RA (26). The MS/MS spectra and peptide sequences determined for these autoantigens are shown in FIG. 3.

The immunogenic HLA-DR-presented peptide derived from filamin A was identified in both ST and PBMC, whereas the peptides from ECGF, apoB-100, annexin A2, and N-acetylglucosamine-6-sulfatase were identified only in ST. Although annexin A2 had been previously shown to serve as an autoantigen in several rheumatic diseases, including about 10% of patients with RA (59), it had not been previously identified as an autoantigen in LA (25). Likewise, neither of the other three autoantigens in LA (ECGF, MMP-10, and apoB-100) nor the two in RA (N-acetylglucosamine 6-sulfatase and filamin A) had been previously identified as autoantigens in those diseases. Moreover, for proteins in this group that had been reported to be immunogenic prior to this investigation, the precise epitopes had not previously been determined.

In 14 patients with antibiotic-refractory LA, ST was available for histopathologic correlations with autoantibody responses. Autoantibody reactivity with endothelial cell growth factor correlated strongly with obliterative microvascular lesions (36) anti-apoB-100 autoantibodies correlated with greater numbers and activation of endothelial cells and more synovial fibroblast proliferation (23) anti-MMP-10 autoantibodies correlated with measures of cell proliferation, including greater synovial lining layer thickness and greater numbers of synovial fibroblasts (24) and anti-annexin A2 autoantibodies correlated with greater synovial fibroblast proliferation (25). Thus, the identification of T cell epitopes led to the identification of B cell responses that correlated with pathophysiological consequences.

Discussion

In this study, large numbers of HLA-DR-presented peptides are identified directly from clinical samples of ST, SFMC or PBMC of patients with RA or LA. The challenge inherent in this approach exceeds that presented by the already difficult task of identifying HLA-DR-presented peptides in tissue culture systems, in which large numbers of a single cell type can be grown and harvested for analysis. Nevertheless, it was the impressive success that had been realized from tissue culture studies which led to undertaking the direct identification from clinical samples that are reported herein. Tandem mass spectrometry was first used to identify MHC molecules in well-defined tissue culture systems (32); for such analyses, at least $5\times10^8$ cells expressing $2\times10^5$ MHC molecules per cell was regarded as the minimum sample requirement (43). Current reports from the Hunt group and other groups continue to improve and exploit this strategy very effectively to identify very large numbers of MHC- or HLA-bound peptides. These studies have identified both MHC Class I and Class II antigenic peptides in various tumor types, and have probed the mechanisms underlying the generation of HLA-presented peptides (37-39). However, the repertoire of HLA-DR-presented peptides in tissue culture systems contains many peptides derived from source proteins in the tissue culture medium (40, 41). It is thus quite different from direct analysis of clinical samples, as we have found (30). Previously, in vivo presented peptides have been identified in patients' spleen (44), colon (45), kidney (46), pooled bronchiolavage fluid (47), thyroid (48), or thymus (49). These studies, on average, have identified only ~20-40 peptides per sample, and in some instances, samples from different patients needed to be pooled to identify peptides. An important exception was the identification of thousands of peptides, including some cancer-related peptides, presented by soluble HLA complexes that were immunoprecipitated from the plasma of patients and healthy controls (33). In previous study of two patients each with RA or LA, in which samples were analyzed using the QSTAR mass spectrometer, >80 non-redundant peptides were identified in each ST sample (30). In comparison, when the same type of strategy was applied to the sample obtained from our most recent patient, use of the Q Exactive plus MS led to the identification of 801 non-redundant peptides, a substantial increase. Even with recent increases in sensitivity and improvements in data analysis tools, identification of HLA-DR-presented peptides by LC-MS/MS still offers technical challenges. First, not all HLA-DR complexes are quantitatively recovered from a given sample. Additionally, some of the isolated peptides have low ionization efficiency and/or are not selected for MS/MS analysis, and not all spectra can be assigned by the search algorithms, due to low signal intensity, incomplete component resolution, and/or the presence of unusual PTMs. However, as shown here, the performance of MS/MS instruments and search algorithms continues to move forward (60).

In the current study, the greater sensitivity now available was taken advantage of, by analyzing not only ST, but also SFMC and PBMC as additional sources of in vivo HLA-DR-presented peptides that can be determined in individual patients. Although a substantial number of the peptides identified were the same in ST as in SFMC or, to a lesser extent, in PBMC, a number of unique peptides were only identified in SFMC or PBMC. As expected, the number of peptides identified in ST was greater than in SFMC or PBMC. Yet, 67% of the peptides identified in SFMC were also found in ST, and 55% of the peptides identified in PBMC were found in ST. Therefore, the analyses of SFMC and PBMC each provided a window into the ST repertoire, but also yielded antigenic peptides not found in ST. The data herein indicate that a more complete picture in an individual patient can be obtained by analyzing tissue or fluids from more than one site. The addition of SFMC and/or PBMC to the analytical scheme has three advantages. First, a more complete picture of an individual patient can be obtained by analyzing samples from multiple sites. Second, since ST can usually only be obtained from patients who undergo surgical procedures, frequently late in the disease, use of SFMC and/or PBMC allows evaluation of patients early in the disease when immune responses may be more robust. Third, given that ST is usually not available, one may obtain at least some information about events in ST, the target of the immune response in chronic inflammatory forms of arthritis. Thus, the testing of SFMC or PBMC opens up the possibility of testing a broader spectrum of patients at earlier stages of their diseases, and increasing the yield of information about immune reactivity in individual patients.

In RA patients, HLA-DR-presented peptides were identified from many source proteins previously reported to be autoantigens in RA, including vimentin, enolase, fibrinogen and collagen. Interestingly, peptides from many of these same source proteins were frequently found in the joints of LA patients, where they are not known to be immunogenic. In RA, many proteins that contain citrulline have been identified, the non-standard amino acid that results from the enzymatic post-translational modification of arginine, such as vimentin, enolase, fibrinogen, collagen, fibronectin, calreticulin, etc. (11, 61-67). Antibodies to these or other citrullinated proteins, known as ACPA, are strongly associated with RA, particularly in patients with HLA-DR alleles that encode for the RA shared epitope (11-13), a highly homologous amino acid sequence at positions 70-74 (Q K/R RAA) in the B1 chain of the HLA-DR molecule. These residues contribute to the P4 anchoring pocket, giving it an overall positive charge. A disease-linked peptide containing citrulline (neutral R-group) has been shown to have greater affinity for the HLA shared epitope in the P4 pocket, as compared to the unmodified analog that contains arginine (positively charged R-group); this citrullinated peptide has been reported to induce T cell activation in DR4-IE transgenic mice (11). Therefore, the MS/MS spectra herein were searched carefully for evidence of peptides that could contain arginine-to-citrulline conversions. Our search algorithms assigned several peptides as forms containing citrulline residues. However, closer manual inspection of the initially obtained spectra and targeted tandem mass spectra recorded on the Q Exactive plus MS, the most advanced instrument employed in this study, determined that, for each of these peptides, the one-Dalton gain was actually due to deamidation at asparagine. The search algorithms did not distinguish correctly between these two different post-translational modifications because they result in the same peptide mass, and the initial MS/MS spectra contained incomplete series of fragment ions that lacked diagnostic peaks between the residues in question. Asparagine deamidation, in addition to being the product of biological processes, can also result from exposure of the sample to high temperature and/or low pH (68), the very conditions used to elute peptides from the MHC molecules, and thus this modification could, in some cases, be an artifact generated during sample processing. A library of citrullinated proteins has been compiled via LC-MS/MS analysis of RA patients' synovial tissue/fluid (69, 70). Manual search of our LC-MS/MS data according to this inventory did not result in the detection of any citrullinated HLA-DR-presented peptide.

In conclusion, the data disclosed herein show that LC-MS/MS is now sensitive enough to identify large numbers of HLA-DR-presented peptides directly from clinical samples of ST, SFMC and PBMC in individual patients with chronic inflammatory arthritis. In present study, discovery-based LC-MS/MS identification of HLA-DR-presented peptides from an individual patient's tissues or fluids, provided a bridge for the identification of novel autoimmune responses. Of the three autoantigens identified in RA patients, only one had been described previously, and all of the four autoantigens identified in LA patients were novel. A principal advantage of autoantigen identification starting with an immunogenic T cell epitope is that it often focuses the search on more broadly applicable T and B cell responses in many patients that result in sustained high-titer autoantibodies, and these responses correlate with pathophysiological consequences. Furthermore, the identification of in vivo HLA-DR-presented peptides from PBMC, which can be readily obtained from any patient, offers a precision, personalized approach for the identification of potentially pathogenic immune responses in a patient with any immune-mediated disease.

Materials and Methods

Study Patients—The study was approved by the Human Investigations Committee at Massachusetts General Hospital, and all participants gave written informed consent. The five RA patients met the 2010 criteria of the American College of Rheumatology/European League against Rheumatism (ACR/EULAR) definition for the diagnosis of rheumatoid arthritis (50), and the eight LA patients met the criteria of the Centers for Disease Control and Prevention for the diagnosis of Lyme disease (51). All eight LA patients had antibiotic-refractory LA, defined as persistent arthritis for ≥three months after the start of ≥two months of appropriate oral antibiotic therapy and ≥one month of IV antibiotic therapy (52). In LA patients, synovial tissue was obtained at the time of therapeutic, arthroscopic synovectomies, and, in RA patients, the tissue was collected at the time of synovectomy or joint replacement surgery. Sufficient quantities of SFMC were available for analysis in six patients and PBMC were available in four patients.

ST, SFMC, and PBMC Preparation—All the reagents were purchased from Sigma-Aldrich (St. Louis, Mo.) except where noted. ST samples (8-10 g) were prepared using the protocol described previously in reference (30), the contents of which are incorporated hereby in its entirety. Heparinized SFMC and PBMC (~3 to $8 \times 10^7$ cells) were obtained by Ficoll-Hypaque (MP Biomedicals) separation and stored in liquid nitrogen prior to analysis. On the day of purification, SFMC and PBMC samples were quickly thawed by placing in a 37° C. water bath for two minutes. Cells were washed twice in phosphate buffered saline (PBS) (Life Technologies) by centrifuging at 800×g for 10 min. The pellet was re-suspended with 10 mL lysis buffer: 150 mM sodium chloride, 20 mM tris(hydroxymethyl)aminomethane•HCl (pH 8.0), 5 mM ethylenediaminetetraacetic acid disodium solution, 0.04% sodium azide, 1 mM 4-(2-aminoethyl)benzenesulfonyl fluoride•HCl, 10 µg/mL leupeptin, 10 µg/mL pepstatin A, 5 µg/mL aprotinin, and 1% 3-[(3-cholamidopropyl)dimethylammonio]-1-propanesulfonate. Immunoaffinity purifications of HLA-DR complexes from SFMC and PBMC were performed using the protocol previously described for synovial tissue samples in reference (30).

LC-MS/MS—High performance LC-MS/MS was performed on purified HLA-DR-presented peptides after desalting using $C_{18}$ ZipTip (Millipore, Billerica, Mass.). The methods used for each mass spectrometer are described below.

LTQ-Orbitrap XL mass spectrometer—A nanoAcquity UPLC system (Waters Corp., Milford, Mass.) was coupled to an LTQ-Orbitrap XL MS (ThermoFisher Scientific, San Jose, Calif.) through a TriVersa.

NanoMate ion source (Advion, Ithaca, N.Y.)—Peptide enrichment was performed with a trapping column (180 μm×20 mm, 5 μm 100 Å Symmetry $C_{18}$, Waters Corp) at a flow rate of 15 μL/min for 1 min, and separation was achieved with a capillary column (150 μm×10 cm, 1.7 λm 130 Å BEH $C_{18}$, Waters Corp). Buffer A contained 1% acetonitrile (ACN) and 0.1% formic acid in water, and buffer B contained 1% water and 0.1% formic acid in ACN. A linear gradient of buffer B from 2% to 40% over 52 min was used at a flow rate of 0.5 μL/min.

The capillary voltage was set to 1.7 kV using the NanoMate, and the capillary temperature was set to 120° C. The mass spectra were recorded over the range m/z 300-2000 at a resolution of 60,000 (the width of the peak at half its maximum height at m/z 300) at a scan rate of approximately 1.2 s/spectrum. Tandem MS was performed for the five most abundant, multiply-charged species in the mass spectra that had a signal intensity threshold of 8000 NL. The normalized collision energy for CID was set to 35%, and helium was used as the collision gas. MS/MS spectra were recorded with the LTQ XL linear ion trap. All spectra were recorded in profile mode. Two to five LC-MS/MS runs were performed for each sample, and all the RAW files for each sample were combined into one Mascot generic file using Proteome Discoverer 1.3 software (ThermoFisher Scientific).

Q Exactive plus mass spectrometer—A nanoAcquity UPLC system was coupled to a Q Exactive plus MS (ThermoFisher Scientific, San Jose, Calif.) through a TriVersa NanoMate ion source. The same peptide enrichment and separation columns, HPLC solvents and gradients, and NanoMate capillary voltage and temperature used on the LTQ-Orbitrap XL MS were applied on the Q Exactive plus MS. Survey MS scans were recorded over the range m/z 400-2000 with a resolution of 70,000 (at m/z 300). The 15 most abundant, multiply-charged ions were selected for higher-energy collisional induced dissociation (HCD) MS/MS with a resolution of 17,500, an isolation width of 1.5 m/z, and a normalized collision energy of 27%. All spectra were recorded in profile mode. One LC-MS/MS run was performed for each sample, and the RAW file for each sample was converted to a Mascot generic file using Proteome Discoverer 1.3 software (ThermoFisher Scientific).

6550 iFunnel QTOF LC/MS—Two 1260 HPLC systems were coupled to a 6550 iFunnel QTOF MS through a chip cube interface (Agilent Technologies, Santa Clara, Calif.). A Polaris-HR-3C18 chip was used for peptide enrichment and separation. The flow rate on the enrichment column was set at 2 μL/min with sample flush volume set as 4 μL. With the same solvents used on the Waters UPLC systems, a gradient of buffer B (from 2% to 5% over 0.1 min, 5% to 20% over 74.9 min, 20% to 40% over 10 min, 40% to 90% over 10 min, held at 90% buffer B for 5 min, returned to 2% buffer B and held for 10 min) was used at a flow rate of 0.3 μL/min for peptide separation. The capillary voltage was set to 1.7 to 1.95 kV, and the gas temperature was set to 225° C. The survey mass spectra were recorded over the range m/z 295-1700 with acquisition rate of 8 spectra/second. Tandem mass spectra were recorded over the range m/z 50-1700 with an acquisition rate of 3 spectra/second. Precursor ion isolation was performed with a narrow isolation window of 1.3 m/z. Tandem MS was performed for the 20 most abundant, multiply-harged species in the mass spectra that had a signal intensity threshold of 5000 counts or a relative threshold of 0.001%. The collision energy for CID was set using the formula [3.1×(m/z)/100+1] for doubly charged precursor ions and [3.6×(m/z)/100−4.8] for triply and higher charged precursor ions. Active exclusion was enabled after recording one tandem spectrum and released after 0.15 min. All spectra were recorded in the centroid mode. One to two LC-MS/MS runs were performed for each sample, and all the data files for each sample were combined into one Mascot generic file using MassHunter Qualitative Analysis B.05.00 (Agilent Technologies, Santa Clara, Calif.).

Protein Database Searching—In previous study, the International Protein Index (IPI) database (72,155 protein sequences) was used to identify HLA-DR-presented peptides from ST samples from two patients each with RA or LA (identified here as patients RA1, RA2, LA1 and LA2 (30). Because the IPI database is now closed and no longer maintained, the spectra obtained for the samples from these four patients were reanalyzed using the UniProt protein database (95,500 entries, August 2010) and the findings were compared to our previous study reference (30). Using the UniProt database, ~96-98% of the peptides identified were the same as those previously assigned using the IPI database. Since an SFMC sample from LA2, and SFMC and PBMC samples from RA2 were available for analysis in this study, the re-analyzed LC-MS/MS data from ST of RA1, RA2, LA1, and LA2 were included here for comparison of the HLA-DR-presented peptides repertoires in ST, SFMC, and PBMC. In the current study, HLA-DR-presented self-peptides were identified by searching the Mascot generic file from each sample against the UniProt human database concatenated with a decoy database. The decoy databases were generated by randomizing each protein sequence in the database using the Perl script decoy.pl (Matrix Science). Mascot 2.4.0 (Matrix Science), OMSSA Browser 2.1.1 (NCBI), and X!Tandem tandem-win-12-10-01-1 (The Global Proteome Machine Organization www.thegpm.org) were used for database searches. For inclusion of a peptide sequence in our database, a consensus match was required (assignment of the sequence by >two search engines) or a match by only one program that was judged acceptable upon review by two experts. Cysteinylation of cysteine, deamidation of glutamine and asparagine, pyroglutamic acid from amino-terminal glutamine and glutamic acid, and oxidation of methionine were specified as the variable modifications in all searches. S-cysteinylated peptides have been identified in MHC class I- and class II-presented peptides (53-56) and in our previous study (30). In addition, the conversion of arginine to citrulline was included as a variable post-translational modification; peaks exhibiting the difference in molecular weight corresponding to arginine vs. citrulline (Δ=0.98402 Da) were searched for each arginine residue in the database.

For data acquired using the LTQ-Orbitrap XL MS, precursor ion error tolerance was set as 0.01 Da and fragment ion error tolerance was set as 0.5 Da; for data acquired using Q Exactive plus MS, precursor ion error tolerance was set as 10 ppm and fragment ion error tolerance was set as 20 mmu; for data acquired using 6550 iFunnel QTOF MS, precursor ion error tolerance was set as 20 ppm and fragment ion error tolerance was set as 50 mmu. "No enzyme" was specified for all the protein database searches. Mascot score cutoff was set at ≥20; OMSSA e-value cutoff was set to ≤0.01; and X!Tandem e-value cutoff was set at ≤10. In addition, consensus identifications of peptides by at least two search programs were correlated using a Microsoft Access query. Over the course of the study, UniProt human protein database was continuously updated. To validate the results obtained with the UniProt database presented herein, the spectra obtained from a recent PBMC sample from an RA patient were reanalyzed using a Swiss-Prot protein database (20,100 entries, January 2016) and 93% of the peptides identified with the updated database were the same as those assigned using the UniProt database used here.

Removal of redundant peptide sequences—The endogenous HLA-DR-presented peptides derived from the same source protein often contain overlapping sequences with different peptide lengths. For example, $^{116}$DHLKYVMLPVA$^{126}$ (SEQ ID NO: 10), $^{116}$DHLKYVMLPVAD$^{127}$ (SEQ ID NO: 11), and 116DHLKYVMLPVADQ$^{128}$ (SEQ ID NO: 12) from HP protein (accession Q6PEJ8) were all identified from ST of LA8, and $^{116}$DHLKYVMLPVA$^{126}$ (SEQ ID NO: 13) and $^{116}$DHLKYVMLPVAD$^{127}$ (SEQ ID NO: 14) were considered redundant peptides of 116DHLKYVMLPVADQ$^{128}$ (SEQ ID NO: 15). To address this issue, the lists of identified consensus peptides were submitted to software generated in-house that collates and sets aside redundant peptides that have amino acid sequences that overlap in a core sequence. Peptide sequences with at least six continuous overlapping amino acid residues were considered redundant, and the peptide with the longest amino acid sequence was output from the software program. This software was also used to compare the consensus peptides among different samples. Peptide sequences with at least six continuous overlapping amino acid residues were considered consensus.

Identification of source proteins—All of the consensus peptides identified by at least two protein database search engines, and peptides assigned by a single program whose identifications passed close manual inspection, were submitted to another software program generated in-house, that screens the peptide sequences against the UniProt human protein database (not including decoy sequences). All the accession numbers of the source proteins containing the screened peptide sequence are displayed as a text string concatenating the accession numbers by semicolons in Microsoft Excel. This search showed that a number of identified peptides could be derived from more than one source protein, the consensus source proteins among different samples were correlated by matching the text strings containing protein accession numbers using a Microsoft Access query. The mass spectrometry proteomics data have been deposited to the ProteomeXchange Consortium (57) via the PRIDE partner repository with the dataset identifier PXD003051.

Determinations of immunogenicity of peptides and source proteins—For the translational component of the protocol, all non-redundant peptides identified by LC-MS/MS were synthesized and evaluated against the matching patient's PBMC using ELISpot assays. Immunogenic peptides were then tested for T cell reactivity by ELISpot assay, and the source proteins of the peptides were assayed for B cell responses by ELISA in many patients and control subjects. To date, the determinations of peptide immunogenicity have been completed for three RA and in five LA patients (22-26). Further such analyses are ongoing.

Statistics—All p values are two-tailed. A p value of ≤0.05 was considered statistically significant.

Example 3—ELISPOT Assays can be Performed with GNS and/or Filamin A Peptides Suspected of Being Autoantigens in a Subject Enzyme-linked immunosorbent spot (ELISPOT) assays are performed using ELISpot$^{plus}$ for human IFN-γ kits (Mabtech Inc., #3420-2AW-Plus). Briefly, PBMC collected using Ficoll-Hypaque density centrifugation and stored in liquid nitrogen are thawed quickly and plated in round bottom, 96-well plates (Costar, #3799) at 2×10$^5$ per well in 200 μl of complete media (RPMI-1640, 2 mM glutamine, 100 units/ml penicillin 100 μg/ml streptomycin, 10 mM HEPES (all from Invitrogen) and 10% human AB serum (Cellgrow). Full length protein or shorter peptide fragments are added at a concentration of 1 μM in duplicate wells. Positive and negative controls consist of 1% PHA (Invitrogen, #10576-015) and no antigen, respectively. After 5 days at 37° C. and 5% $CO_2$, cells are transferred to ELISPOT plates (Mabtech), previously coated with IFN-γ capture antibody, and incubated overnight. All subsequent steps are performed as detailed in the manufacturer's protocol. Images of wells are captured using ImmunoSpot series 3B analyzer and spots counted using ImmunoSpot 5.0 academic software (Cellular Technology Limited).

Example 4—ELISA Assays can be Performed with GNS and/or Filamin A Peptides Suspected of Being Autoantigens in a Subject Serum anti-peptide antibody ELISA: EasyWash ELISA plates (CoStar) are coated with 100 μl of 0.5 μg/ml carrier free, recombinant human GNS and/or filamin A full length protein or peptide fragments dissolved in PBS and incubated overnight at 4° C. All subsequent steps are performed at room temperature with plates on a platform shaker set at 200 rpm. The next day, plates are washed three times with PBST (phosphate buffered saline and 0.05% Tween-20) then incubated with 200 μl of blocking buffer (5% nonfat dry milk in PBST) for 1 hr. Afterwards, wells are washed three times with PBST and 100 μl of each patient's serum sample diluted 1/100 with blocking buffer is added to individual wells and incubated for 1 hr. As a control, serum from eight healthy subjects is added to each plate to be used for inter-plate standardization. After three more washes with PBST, 100 μl goat anti-human IgG conjugated to horseradish peroxidase (KPL #074-1006) diluted 1:7500 in blocking buffer is added to each well and incubated for 1 hr. Plates are then washed three times with PBST, followed by three times with PBS and incubated with 100 μl of a 1:1 mixture of the substrate 3,3',5,5'-tetramethylbenzidine and 0.01% hydrogen peroxide (TMB substrate reagent kit, #555214) (BD Biosciences). The reaction is stopped after 3 min with 100 μl of 2N sulfuric acid (LabChem Inc., #LC25790-2). Absorbance values ($OD_{450}$) for each well were determined using a microplate reader (Bio-Rad, model 550).

Synovial Fluid Autoantigen Sandwich ELISA:

EasyWash ELISA plates are coated with 50 μl of the capture antibody, goat anti-human autoantigen (human GNS and/or filamin A full length protein or peptide fragments) diluted in PBS (5 μg/ml) and incubated overnight at 4° C. All subsequent steps are performed at room temperature. The next day, plates are washed three times with PBS and incubated with blocking buffer for 30 min. Afterwards, plates are washed three times with PBS and 100 μl of each patients' synovial fluid sample diluted 1:10 with blocking buffer are added to individual wells and incubated for 2 hr. In order to quantify results, recombinant human autoantigen serially diluted with blocking buffer is also added to each plate to generate a standard curve. After washing the plates three times, wells are filled with 150 μl of blocking buffer, gently vortexed and washed again three times with PBS to ensure removal of all unbound proteins. Plates are then incubated with 50 μl of the mouse anti-human autoantigen antibody diluted in blocking buffer (5 ng/ml) for 2 hr. Plates are again washed with PBS and 50 μl of the detection antibody, goat anti-mouse IgG conjugated to horse radish peroxidase (Santa Cruz, #SC-2005) diluted in blocking buffer (1:1000) is added to plates and incubated for 1 hr. After plates are washed three times with PBS, 100 μl of TMB was added for ~6 min and then the reaction is stopped with 100 μl of 2N sulfuric acid. Plates are read as described above.

Example 5—Immunoblotting can be Performed with GNS and/or Filamin A Peptides Suspected of Being Autoantigens in a Subject Autoantigen (e.g, human GNS and/or filamin A full length protein or peptide fragments, such as human recombinant autoantigen) 12 μg is electrophoresed through a 10% mini-PROTEAN TGX gels (Bio-Rad) then transferred to nitrocellulose membranes. All subsequent steps are performed at room temperature with rocking. Membranes are cut into strips, individually placed into eight channel reservoir liners (Costar, #4878) and incubated for 1 hr in 1.5 ml blocking buffer (5% nonfat dry milk, 0.1% Tween-20 in 20 mM Tris, 500 mM sodium chloride; pH 7.5). Afterwards, strips are washed three times for 1 min intervals with rinse buffer (0.1% Tween-20 in 20 mM Tris, 500 mM sodium chloride; pH 7.5) and each individual strip is incubated for 1 hr with patient's serum diluted 1:100 in blocking buffer. Strips are again washed three times with rinse buffer and incubated for 1 hr with goat anti-human IgG antibody conjugated to alkaline phosphatase (KPL, #4751-1006) diluted 1:2000 in blocking buffer. Strips are washed three times with rinse buffer and another three times with 20 mM Tris, 500 mM sodium chloride; pH 7.5. Bands are visualized by incubation with NBT/BCIP substrate solution (Roche Diagnostics GmbH, #11681451001) for 3-5 min after which the strips are washed with copious amounts of water to stop the reaction. Bands are considered positive if darker than the pre-determined positive control sample included in each assay.

REFERENCES

1. McDevitt, H. O. and Bodmer, W. F. HL-A, immune-response genes, and disease *Lancet* 1974, 1, 1269-1275.
2. Takemura, S., Braun, A., Crowson, C., Kurtin, P. J., Cofield, R. H., O'Fallon, W. M., Goronzy, J. J. and Weyand, C. M. Lymphoid neogenesis in rheumatoid synovitis *J Immunol* 2001, 167, 1072-1080.
3. Steere, A. C., Duray, P. H. and Butcher, E. C. Spirochetal antigens and lymphoid cell surface markers in Lyme synovitis. Comparison with rheumatoid synovium and tonsillar lymphoid tissue *Arthritis Rheum* 1988, 31, 487-495.
4. Plenge, R. M. Rheumatoid arthritis genetics: 2009 update *Curr Rheumatol Rep* 2009, 11, 351-356.
5. Stefanova, I., Dorfman, J. R., Tsukamoto, M. and Germain, R. N. On the role of self-recognition in T cell responses to foreign antigen *Immunol Rev* 2003, 191, 97-106.
6. Gregersen, P. K., Silver, J. and Winchester, R. J. The shared epitope hypothesis. An approach to understanding the molecular genetics of susceptibility to rheumatoid arthritis *Arthritis Rheum* 1987, 30, 1205-1213.
7. Holoshitz, J. The rheumatoid arthritis HLA-DRB1 shared epitope *Curr Opin Rheumatol* 2010, 22, 293-298.
8. Berglin, E., Johansson, T., Sundin, U., Jidell, E., Wadell, G., Hallmans, G. and Rantapaa-Dahlqvist, S. Radiological outcome in rheumatoid arthritis is predicted by presence of antibodies against cyclic citrullinated peptide before and at disease onset, and by IgA-RF at disease onset *Ann Rheum Dis* 2006, 65, 453-458.
9. de Vries-Bouwstra, J. K., Goekoop-Ruiterman, Y. P., Verpoort, K. N., Schreuder, G. M., Ewals, J. A., Terwiel, J. P., Ronday, H. K., Kerstens, P. J., Toes, R. E., de Vries, R. R., Breedveld, F. C., Dijkmans, B. A., Huizinga, T. W. and Allaart, C. F. Progression of joint damage in early rheumatoid arthritis: association with HLA-DRB1, rheumatoid factor, and anti-citrullinated protein antibodies in relation to different treatment strategies *Arthritis Rheum* 2008, 58, 1293-1298.
10. Pratesi, F., Petit Teixeira, E., Sidney, J., Michou, L., Puxeddu, I., Sette, A., Cornelis, F. and Migliorini, P. HLA shared epitope and ACPA: just a marker or an active player? *Autoimmun Rev* 2013, 12, 1182-1187.
11. Hill, J. A., Southwood, S., Sette, A., Jevnikar, A. M., Bell, D. A. and Cairns, E. Cutting edge: the conversion of arginine to citrulline allows for a high-affinity peptide interaction with the rheumatoid arthritis-associated HLA-DRB1*0401 MHC class II molecule *J Immunol* 2003, 171, 538-541.
12. Snir, O., Widhe, M., von Spee, C., Lindberg, J., Padyukov, L., Lundberg, K., Engstrom, A., Venables, P. J., Lundeberg, J., Holmdahl, R., Klareskog, L. and Malmstrom, V. Multiple antibody reactivities to citrullinated antigens in sera from patients with rheumatoid arthritis: association with HLA-DRB1 alleles *Ann Rheum Dis* 2009, 68, 736-743.
13. Huizinga, T. W., Amos, C. I., van der Helm-van Mil, A. H., Chen, W., van Gaalen, F. A., Jawaheer, D., Schreuder, G. M., Wener, M., Breedveld, F. C., Ahmad, N., Lum, R. F., de Vries, R. R., Gregersen, P. K., Toes, R. E. and Criswell, L. A. Refining the complex rheumatoid arthritis phenotype based on specificity of the HLA-DRB1 shared epitope for antibodies to citrullinated proteins *Arthritis Rheum* 2005, 52, 3433-3438.
14. Steere, A. C. Lyme disease *N Engl J Med* 2001, 345, 115-125.
15. Steere, A. C., Schoen, R. T. and Taylor, E. The clinical evolution of Lyme arthritis *Ann Intern Med* 1987, 107, 725-731.
16. Steere, A. C., Levin, R. E., Molloy, P. J., Kalish, R. A., Abraham, J. H., 3rd, Liu, N. Y. and Schmid, C. H. Treatment of Lyme arthritis *Arthritis Rheum* 1994, 37, 878-888.
17. Steere, A. C. and Angelis, S. M. Therapy for Lyme arthritis: strategies for the treatment of antibiotic-refractory arthritis *Arthritis Rheum* 2006, 54, 3079-3086.
18. Shin, J. J., Glickstein, L. J. and Steere, A. C. High levels of inflammatory chemokines and cytokines in joint fluid and synovial tissue throughout the course of antibiotic-refractory lyme arthritis *Arthritis Rheum* 2007, 56, 1325-1335.
19. Strle, K., Shin, J. J., Glickstein, L. J. and Steere, A. C. Association of a Toll-like receptor 1 polymorphism with heightened Th1 inflammatory responses and antibiotic-refractory Lyme arthritis *Arthritis Rheum* 2012, 64, 1497-1507.
20. Shen, S., Shin, J. J., Strle, K., McHugh, G., Li, X., Glickstein, L. J., Drouin, E. E. and Steere, A. C. Treg cell numbers and function in patients with antibiotic-refractory or antibioticresponsive Lyme arthritis *Arthritis Rheum* 2010, 62, 2127-2137.
21. Vudattu, N. K., Strle, K., Steere, A. C. and Drouin, E. E. Dysregulation of CD4+CD25(high) T cells in the synovial fluid of patients with antibiotic-refractory Lyme arthritis *Arthritis Rheum* 2013, 65, 1643-1653.

22. Drouin, E. E., Seward, R. J., Strle, K., McHugh, G., Katchar, K., Londono, D., Yao, C., Costello, C. E. and Steere, A. C. A novel human autoantigen, endothelial cell growth factor, is a target of T and B cell responses in patients with Lyme disease *Arthritis Rheum* 2013, 65, 186-196.
23. Crowley, J. T., Drouin, E. E., Pianta, A., Strle, K., Wang, Q., Costello, C. E. and Steere, A. C. A highly expressed human protein, apolipoprotein B-100, serves as an autoantigen in a subgroup of patients with Lyme disease *J Infect Dis* 2015, doi 10.1093/infdis/jiv1310.
24. Crowley, J. T., Strle, K., Drouin, E. E., Pianta, A., Arvikar, S. L., Wang, Q., Costello, C. E. and Steere, A. C. Matrix metalloproteinase-10 is a target of T and B cell responses that correlate with synovial pathology in patients with antibiotic-refractory Lyme arthritis. *J Autoimmun.* 2016, 69, 24-37.
25. Pianta, A., Drouin, E. E., Crowley, J. T., Arvikar, S., Strle, K., Costello, C. E. and Steere, A. C. Annexin A2 is a target of T and B cell responses associated with synovial fibroblast proliferation in patients with antibiotic-refractory Lyme arthritis. *Clin Immunol* 2015, 160, 336-341.
26. Pianta, A., Drouin, E. E., Wang, Q., Arvikar, S., Costello, C. E. and Steere, A. C. Identification of N-acetylglucosamine-6-sulfatase and filamin A as novel targets of autoimmune T and B cell responses in rheumatoid arthritis. *Ann Rheum Dis* 2015, 74S, 112.
27. Steere, A. C., Klitz, W., Drouin, E. E., Falk, B. A., Kwok, W. W., Nepom, G. T. and Baxter-Lowe, L. A. Antibiotic-refractory Lyme arthritis is associated with HLA-DR molecules that bind a *Borrelia burgdorferi* peptide *J Exp Med* 2006, 203, 961-971.
28. Moret, F. M., Hack, C. E., van der Wurff-Jacobs, K. M., de Jager, W., Radstake, T. R., Lafeber, F. P. and van Roon, J. A. Intra-articular CD1c-expressing myeloid dendritic cells from rheumatoid arthritis patients express a unique set of T cell-attracting chemokines and spontaneously induce Th1, Th17 and Th2 cell activity *Arthritis Res Ther* 2013, 15, R155.
29. Katchar, K., Drouin, E. E. and Steere, A. C. Natural killer cells and natural killer T cells in Lyme arthritis *Arthritis Res Ther* 2013, 15, R183.
30. Seward, R. J., Drouin, E. E., Steere, A. C. and Costello, C. E. Peptides presented by HLA-DR molecules in synovia of patients with rheumatoid arthritis or antibiotic-refractory Lyme arthritis *Mol Cell Proteomics* 2011, 10, M110 002477.
31. Biemann, K. Appendix 5. Nomenclature for peptide fragment ions (positive ions) *Methods Enzymol* 1990, 193, 886-887.
32. Hunt, D. F., Henderson, R. A., Shabanowitz, J., Sakaguchi, K., Michel, H., Sevilir, N., Cox, A. L., Appella, E. and Engelhard, V. H. Characterization of peptides bound to the class I MHC molecule HLA-A2.1 by mass spectrometry *Science* 1992, 255, 1261-1263.
33. Bassani-Sternberg, M., Barnea, E., Beer, I., Avivi, I., Katz, T. and Admon, A. Soluble plasma HLA peptidome as a potential source for cancer biomarkers *Proc Natl Acad Sci USA* 2010, 107, 18769-18776.
34. Alvarez-Navarro, C., Cragnolini, J. J., Dos Santos, H. G., Barnea, E., Admon, A., Morreale, A. and Lopez de Castro, J. A. Novel HLA-B27-restricted epitopes from Chlamydia trachomatis generated upon endogenous processing of bacterial proteins suggest a role of molecular mimicry in reactive arthritis *J Biol Chem* 2013, 288, 25810-25825.
35. Bassani-Sternberg, M., Pletscher-Frankild, S., Jensen, L. J. and Mann, M. Mass spectrometry of human leukocyte antigen class I peptidomes reveals strong effects of protein abundance and turnover on antigen presentation *Mol Cell Proteomics* 2015, 14, 658-673.
36. Londono, D., Cadavid, D., Drouin, E. E., Strle, K., McHugh, G., Aversa, J. M. and Steere, A. C. Antibodies to endothelial cell growth factor and obliterative microvascular lesions in the synovium of patients with antibiotic-refractory lyme arthritis *Arthritis & Rheumatology* 2014, 66, 2124-2133.
37. Cobbold, M., De La Pena, H., Norris, A., Polefrone, J. M., Qian, J., English, A. M., Cummings, K. L., Penny, S., Turner, J. E., Cottine, J., Abelin, J. G., Malaker, S. A., Zarling, A. L., Huang, H. W., Goodyear, O., Freeman, S. D., Shabanowitz, J., Pratt, G., Craddock, C., Williams, M. E., Hunt, D. F. and Engelhard, V. H. MHC class I-associated phosphopeptides are the targets of memory-like immunity in leukemia *Sci Transl Med* 2013, 5, 203ra125.
38. Li, Y., Depontieu, F. R., Sidney, J., Salay, T. M., Engelhard, V. H., Hunt, D. F., Sette, A., Topalian, S. L. and Mariuzza, R. A. Structural basis for the presentation of tumor-associated MHC class II-restricted phosphopeptides to CD4+ T cells *J Mol Biol* 2010, 399, 596-603.
39. Guasp, P., Alvarez-Navarro, C., Gomez-Molina, P., Martin-Esteban, A., Marcilla, M., Barnea, E., Admon, A. and Lopez de Castro, J. A. The Peptidome of Behcet's Disease-Associated HLA-B*51:01 Includes Two Subpeptidomes Differentially Shaped by Endoplasmic Reticulum Aminopeptidase 1 *Arthritis & Rheumatology* 2016, 68, 505-515.
40. Chicz, R. M., Urban, R. G., Gorga, J. C., Vignali, D. A., Lane, W. S. and Strominger, J. L. Specificity and promiscuity among naturally processed peptides bound to HLA-DR alleles *J Exp Med* 1993, 178, 27-47.
41. Lippolis, J. D., White, F. M., Marto, J. A., Luckey, C. J., Bullock, T. N., Shabanowitz, J., Hunt, D. F. and Engelhard, V. H. Analysis of MHC class II antigen processing by quantitation of peptides that constitute nested sets *J Immunol* 2002, 169, 5089-5097.
42. Caron, E., Espona, L., Kowalewski, D. J., Schuster, H., Ternette, N., Alpizar, A., Schittenhelm, R. B., Ramarathinam, S. H., Lindestam Arlehamn, C. S., Chiek Koh, C., Gillet, L. C., Rabsteyn, A., Navarro, P., Kim, S., Lam, H., Sturm, T., Marcilla, M., Sette, A., Campbell, D. S., Deutsch, E. W., Moritz, R. L., Purcell, A. W., Rammensee, H. G., Stevanovic, S. and Aebersold, R. An open-source computational and data resource to analyze digital maps of immunopeptidomes *Elife* 2015, 4, doi: 10.7554/eLife.07661.
43. Caron, E., Kowalewski, D. J., Chiek Koh, C., Sturm, T., Schuster, H. and Aebersold, R. Analysis of Major Histocompatibility Complex (MHC) Immunopeptidomes Using Mass Spectrometry *Mol Cell Proteomics* 2015, 14, 3105-3117.
44. Gordon, R. D., Young, J. A., Rayner, S., Luke, R. W., Crowther, M. L., Wordsworth, P., Bell, J., Hassall, G., Evans, J., Hinchliffe, S. A. and et al. Purification and characterization of endogenous peptides extracted from HLA-DR isolated from the spleen of a patient with rheumatoid arthritis *Eur J Immunol* 1995, 25, 1473-1476.
45. Oshitani, N., Hato, F., Kitagawa, S., Maeda, K., Higuchi, K., Matsumoto, T. and Arakawa, T. Analysis of intestinal HLA-DR bound peptides and dysregulated immune responses to enteric flora in the pathogenesis of inflammatory bowel disease *Int J Mol Med* 2003, 11, 99-104.
46. Dengjel, J., Nastke, M. D., Gouttefangeas, C., Gitsioudis, G., Schoor, O., Altenberend, F., Muller, M., Kramer, B., Missiou, A., Sauter, M., Hennenlotter, J., Wernet, D., Stenzl, A., Rammensee, H. G., Klingel, K. and Stevanovic, S. Unexpected abundance of HLA class II presented peptides in primary renal cell carcinomas *Clin Cancer Res* 2006, 12, 4163-4170.
47. Wahlstrom, J., Dengjel, J., Persson, B., Duyar, H., Rammensee, H. G., Stevanovic, S., Eklund, A., Weissert, R. and Grunewald, J. Identification of HLA-DR-bound peptides presented by human bronchoalveolar lavage cells in sarcoidosis *J Clin Invest* 2007, 117, 3576-3582.
48. Muixi, L., Carrascal, M., Alvarez, I., Daura, X., Marti, M., Armengol, M. P., Pinilla, C., Abian, J., Pujol-Borrell, R. and Jaraquemada, D. Thyroglobulin peptides associate in vivo to HLA-DR in autoimmune thyroid glands *J Immunol* 2008, 181, 795-807.
49. Collado, J. A., Alvarez, I., Ciudad, M. T., Espinosa, G., Canals, F., Pujol-Borrell, R., Carrascal, M., Abian, J. and Jaraquemada, D. Composition of the HLA-DR-associated human thymus peptidome *Eur J Immunol* 2013, 43, 2273-2282.
50. Aletaha, D., Neogi, T., Silman, A. J., Funovits, J., Felson, D. T., Bingham, C. O., 3rd, Birnbaum, N. S., Burmester, G. R., Bykerk, V. P., Cohen, M. D., Combe, B., Costenbader, K. H., Dougados, M., Emery, P., Ferraccioli, G., Hazes, J. M., Hobbs, K., Huizinga, T. W., Kavanaugh, A., Kay, J., Kvien, T. K., Laing, T., Mease, P., Menard, H. A., Moreland, L. W., Naden, R. L., Pincus, T., Smolen, J. S., Stanislawska-Biernat, E., Symmons, D., Tak, P. P., Upchurch, K. S., Vencovsky, J., Wolfe, F. and Hawker, G. 2010 Rheumatoid arthritis classification criteria: an American College of Rheumatology/European League Against Rheumatism collaborative initiative *Arthritis Rheum* 2010, 62, 2569-2581.
51. Wharton, M., Chorba, T. L., Vogt, R. L., Morse, D. L. and Buehler, J. W. Case definitions for public health surveillance *MMWR Recomm Rep* 1990, 39, 1-43.
52. Steere, A. C. and Glickstein, L. Elucidation of Lyme arthritis *Nat Rev Immunol* 2004, 4, 143-152.
53. Chen, W., Yewdell, J. W., Levine, R. L. and Bennink, J. R. Modification of cysteine residues in vitro and in vivo affects the immunogenicity and antigenicity of major histocompatibility complex class I-restricted viral determinants *J Exp Med* 1999, 189, 1757-1764.
54. Hague, M. A., Hawes, J. W. and Blum, J. S. Cysteinylation of MHC class II ligands: peptide endocytosis and reduction within APC influences T cell recognition *J Immunol* 2001, 166, 4543-4551.
55. Meadows, L., Wang, W., den Haan, J. M., Blokland, E., Reinhardus, C., Drijfhout, J. W., Shabanowitz, J., Pierce, R., Agulnik, A. I., Bishop, C. E., Hunt, D. F., Goulmy, E. and Engelhard, V. H. The HLA-A*0201-restricted H-Y antigen contains a posttranslationally modified cysteine that significantly affects T cell recognition *Immunity* 1997, 6, 273-281.
56. Pierce, R. A., Field, E. D., den Haan, J. M., Caldwell, J. A., White, F. M., Marto, J. A., Wang, W., Frost, L. M., Blokland, E., Reinhardus, C., Shabanowitz, J., Hunt, D. F., Goulmy, E. and Engelhard, V. H. Cutting edge: the HLA-A*0101-restricted HY minor histocompatibility antigen originates from DFFRY and contains a cysteinylated cysteine residue as identified by a novel mass spectrometric technique *J Immunol* 1999, 163, 6360-6364.
57. Vizcaino, J. A., Deutsch, E. W., Wang, R., Csordas, A., Reisinger, F., Rios, D., Dianes, J. A., Sun, Z., Farrah, T., Bandeira, N., Binz, P. A., Xenarios, I., Eisenacher, M., Mayer, G., Gatto, L., Campos, A., Chalkley, R. J., Kraus, H. J., Albar, J. P., Martinez-Bartolome, S., Apweiler, R., Omenn, G. S., Martens, L., Jones, A. R. and Hermjakob, H. ProteomeXchange provides globally coordinated proteomics data submission and dissemination *Nat Biotechnol* 2014, 32, 223-226.
58. Behera, A. K., Hildebrand, E., Szafranski, J., Hung, H. H., Grodzinsky, A. J., Lafyatis, R., Koch, A. E., Kalish, R., Perides, G., Steere, A. C. and Hu, L. T. Role of aggrecanase 1 in Lyme arthritis *Arthritis Rheum* 2006, 54, 3319-3329.
59. Salle, V., Maziere, J. C., Smail, A., Cevallos, R., Maziere, C., Fuentes, V., Tramier, B., Makdassi, R., Choukroun, G., Vittecoq, O., Goeb, V. and Ducroix, J. P. Anti-annexin II antibodies in systemic autoimmune diseases and antiphospholipid syndrome *J Clin Immunol* 2008, 28, 291-297.
60. Zhang, B., Pirmoradian, M., Chernobrovkin, A. and Zubarev, R. A. DeMix workflow for efficient identification of cofragmented peptides in high resolution data-dependent tandem mass spectrometry *Mol Cell Proteomics* 2014, 13, 3211-3223.
61. Vossenaar, E. R., Despres, N., Lapointe, E., van der Heijden, A., Lora, M., Senshu, T., van Venrooij, W. J. and Menard, H. A. Rheumatoid arthritis specific anti-Sa antibodies target citrullinated vimentin *Arthritis Res Ther* 2004, 6, R142-150.
62. Kinloch, A., Tatzer, V., Wait, R., Peston, D., Lundberg, K., Donatien, P., Moyes, D., Taylor, P. C. and Venables, P. J. Identification of citrullinated alpha-enolase as a candidate autoantigen in rheumatoid arthritis *Arthritis Res Ther* 2005, 7, R1421-1429.
63. Takizawa, Y., Suzuki, A., Sawada, T., Ohsaka, M., Inoue, T., Yamada, R. and Yamamoto, K. Citrullinated fibrinogen detected as a soluble citrullinated autoantigen in rheumatoid arthritis synovial fluids *Ann Rheum Dis* 2006, 65, 1013-1020.
64. Burkhardt, H., Sehnert, B., Bockermann, R., Engstrom, A., Kalden, J. R. and Holmdahl, R. Humoral immune response to citrullinated collagen type II determinants in early rheumatoid arthritis *Eur J Immunol* 2005, 35, 1643-1652.
65. van Beers, J. J., Willemze, A., Stammen-Vogelzangs, J., Drijfhout, J. W., Toes, R. E. and Pruijn, G. J. Anti-citrullinated fibronectin antibodies in rheumatoid arthritis are associated with human leukocyte antigen-DRB1 shared epitope alleles *Arthritis Res Ther* 2012, 14, R35.
66. Ling, S., Cline, E. N., Haug, T. S., Fox, D. A. and Holoshitz, J. Citrullinated calreticulin potentiates rheumatoid arthritis shared epitope signaling *Arthritis Rheum* 2013, 65, 618-626.
67. Spengler, J., Lugonja, B., Ytterberg, A. J., Zubarev, R. A., Creese, A. J., Pearson, M. J., Grant, M. M., Milward, M., Lundberg, K., Buckley, C. D., Filer, A., Raza, K., Cooper, P. R., Chapple, I. L. and Scheel-Toellner, D. Release of Active Peptidyl Arginine Deiminases by Neutrophils Can Explain Production of Extracellular Citrullinated Autoantigens in Rheumatoid Arthritis Synovial Fluid *Arthritis & Rheumatology* 2015, 67, 3135-3145.
68. Pace, A. L., Wong, R. L., Zhang, Y. T., Kao, Y. H. and Wang, Y. J. Asparagine deamidation dependence on buffer type, pH, and temperature *J Pharm Sci* 2013, 102, 1712-1723.
69. van Beers, J. J., Schwarte, C. M., Stammen-Vogelzangs, J., Oosterink, E., Bozic, B. and Pruijn, G. J. The rheumatoid arthritis synovial fluid citrullinome reveals novel citrullinated epitopes in apolipoprotein E, myeloid nuclear differentiation antigen, and beta-actin *Arthritis Rheum* 2013, 65, 69-80.

70. Ytterberg, A. J., Joshua, V., Reynisdottir, G., Tarasova, N. K., Rutishauser, D., Ossipova, E., Haj Hensvold, A., Eklund, A., Skold, C. M., Grunewald, J., Malmstrom, V., Jakobsson, P. J., Ronnelid, J., Padyukov, L., Zubarev, R. A., Klareskog, L. and Catrina, A. I. Shared immunological targets in the lungs and joints of patients with rheumatoid arthritis: identification and validation *Ann Rheum Dis* 2015, 74, 1772-1777.

71. Asquith D L, Miller A M, McInnes I B, Liew F Y. Animal models of rheumatoid arthritis. Eur J Immunol. 2009 August; 39(8):2040-4.

72. Arnett F C, Edworthy S M, Bloch D A, et al: The American Rheumatism Association 1987 revised criteria for the classification of rheumatoid arthritis. Arthritis Rheum. 1988, 31: 315-324.

73. Aletaha D, Neogi T, Silman A J, et al. 2010 Rheumatoid arthritis classification criteria: an American College of Rheumatology/European League against Rheumatism collaborative initiative. Ann Rheum Dis 2010; 69:1580-1588.

The invention claimed is:

1. A method of treating rheumatoid arthritis in a subject comprising:
   (a) receiving the results of an assay that indicates an increase in the level of IFNγ secretion and/or T cell proliferation following contact of a biological sample from the subject with one or more of filamin-A and N-acetylglucosamine-6-sulfatase whole protein or polypeptide fragments compared with an appropriate control sample; or
   (b) receiving the results of an assay that indicates an increase in the level of immunocomplexes following contact of a biological sample from the subject with one or more of filamin-A and N-acetylglucosamine-6-sulfatase, whole protein or polypeptide fragments compared to an appropriate control sample; and
   (c) administering to the subject one or more of a non-steroidal anti-inflammatory drug (NSAIDs), a steroid, a disease modifying anti-rheumatic drug (DMARD), adalimumab, etanercept, abatacept, anakinra, cimzia, golimumab, infliximab, tocilizumab and tofacitinib.

2. The method of claim 1, wherein the subject has been or is further tested for one or more of rheumatoid factor, anti-citrullinated protein antibodies (ACPA), and one or more HLA-DR alleles.

3. The method of claim 1, wherein the subject is at risk for, or is suspected of having, rheumatoid arthritis.

4. The method of claim 1, wherein prior to step (a) the biological sample is obtained from a subject at risk for, suspected of having or has rheumatoid arthritis.

5. The method of claim 1, wherein the biological sample is peripheral blood, serum, synovial tissue, synovial fluid, peripheral blood mononuclear cells (PBMC), or synovial fluid mononuclear cells (SFMC) from the subject.

6. The method of claim 1, wherein the appropriate control is a biological sample from a healthy subject.

7. The method of claim 2, wherein the HLA-DR allele is HLA-DRB1*0101 and/or HLA-DRB1*0401, and/or HLA-DRB1*0405, and/or HLA-DRB1*0408, and/or HLA-DRB1*1501.

8. The method of claim 1, wherein the polypeptide fragment of filamin-A comprises the amino acid sequence NPAEFVVNTSNAGAG (SEQ ID NO: 1) or an antigenic portion thereof.

9. The method of claim 1, wherein the polypeptide fragment of N-acetylglucosamine-6-sulfatase comprises the amino acid sequence of FEPFFMMIATPAPH (SEQ ID NO: 2) or an antigenic portion thereof.

10. The method of claim 1, wherein the assay in step (b) is an enzyme-linked immunosorbent assay (ELISA), agglutination test, direct immunofluorescence assay, indirect immunofluorescence assay, or an immunoblot assay.

11. The method of claim 1, wherein the assay in step (a) is an immunospot test or proliferation assay.

12. The method of claim 1, wherein the results received are of step (b) and the assay of step (b) comprises:
   (a) contacting a biological sample with filamin-A protein or a polypeptide fragment thereof; and/or
   (b) contacting a biological sample with N-acetylglucosamine-6-sulfatase protein or a polypeptide fragment thereof; and
   (c) detecting an increase in the level of immunocomplexes of an antibody in the biological sample with the filamin-A protein or polypeptide fragment thereof or N-acetylglucosamine-6-sulfatase protein or polypeptide fragment thereof.

* * * * *

SEQUENCE LISTING

```
<160> NUMBER OF SEQ ID NOS: 16

<210> SEQ ID NO 1
<211> LENGTH: 15
<212> TYPE: PRT
<213> ORGANISM: Homo sapiens

<400> SEQUENCE: 1

Asn Pro Ala Glu Phe Val Val Asn Thr Ser Asn Ala Gly Ala Gly
1               5                   10                  15

<210> SEQ ID NO 2
<211> LENGTH: 14
<212> TYPE: PRT
<213> ORGANISM: Homo sapiens

<400> SEQUENCE: 2

Phe Glu Pro Phe Phe Met Met Ile Ala Thr Pro Ala Pro His
1               5                   10

<210> SEQ ID NO 3
<211> LENGTH: 552
<212> TYPE: PRT
<213> ORGANISM: Homo sapiens

<400> SEQUENCE: 3

Met Arg Leu Leu Pro Leu Ala Pro Gly Arg Leu Arg Gly Ser Pro
1               5                   10                  15

Arg His Leu Pro Ser Cys Ser Pro Ala Leu Leu Leu Val Leu Gly
                20                  25                  30

Gly Cys Leu Gly Val Phe Gly Val Ala Ala Gly Thr Arg Arg Pro Asn
                35                  40                  45

Val Val Leu Leu Leu Thr Asp Asp Gln Asp Glu Val Leu Gly Gly Met
                50                  55                  60

Thr Pro Leu Lys Lys Thr Lys Ala Leu Ile Gly Glu Met Gly Met Thr
65                  70                  75                  80

Phe Ser Ser Ala Tyr Val Pro Ser Ala Leu Cys Cys Pro Ser Arg Ala
                85                  90                  95

Ser Ile Leu Thr Gly Lys Tyr Pro His Asn His His Val Val Asn Asn
                100                 105                 110

Thr Leu Glu Gly Asn Cys Ser Ser Lys Ser Trp Gln Lys Ile Gln Glu
        115                 120                 125

Pro Asn Thr Phe Pro Ala Ile Leu Arg Ser Met Cys Gly Tyr Gln Thr
        130                 135                 140

Phe Phe Ala Gly Lys Tyr Leu Asn Glu Tyr Gly Ala Pro Asp Ala Gly
145                 150                 155                 160

Gly Leu Glu His Val Pro Leu Gly Trp Ser Tyr Trp Tyr Ala Leu Glu
                165                 170                 175
```

```
Lys Asn Ser Lys Tyr Tyr Asn Tyr Thr Leu Ser Ile Asn Gly Lys Ala
                180                 185                 190

Arg Lys His Gly Glu Asn Tyr Ser Val Asp Tyr Leu Thr Asp Val Leu
            195                 200                 205

Ala Asn Val Ser Leu Asp Phe Leu Asp Tyr Lys Ser Asn Phe Glu Pro
        210                 215                 220

Phe Phe Met Met Ile Ala Thr Pro Ala Pro His Ser Pro Trp Thr Ala
225                 230                 235                 240

Ala Pro Gln Tyr Gln Lys Ala Phe Gln Asn Val Phe Ala Pro Arg Asn
                245                 250                 255

Lys Asn Phe Asn Ile His Gly Thr Asn Lys His Trp Leu Ile Arg Gln
                260                 265                 270

Ala Lys Thr Pro Met Thr Asn Ser Ser Ile Gln Phe Leu Asp Asn Ala
                275                 280                 285

Phe Arg Lys Arg Trp Gln Thr Leu Leu Ser Val Asp Asp Leu Val Glu
        290                 295                 300

Lys Leu Val Lys Arg Leu Glu Phe Thr Gly Glu Leu Asn Asn Thr Tyr
305                 310                 315                 320

Ile Phe Tyr Thr Ser Asp Asn Gly Tyr His Thr Gly Gln Phe Ser Leu
                325                 330                 335

Pro Ile Asp Lys Arg Gln Leu Tyr Glu Phe Asp Ile Lys Val Pro Leu
                340                 345                 350

Leu Val Arg Gly Pro Gly Ile Lys Pro Asn Gln Thr Ser Lys Met Leu
                355                 360                 365

Val Ala Asn Ile Asp Leu Gly Pro Thr Ile Leu Asp Ile Ala Gly Tyr
        370                 375                 380

Asp Leu Asn Lys Thr Gln Met Asp Gly Met Ser Leu Leu Pro Ile Leu
385                 390                 395                 400

Arg Gly Ala Ser Asn Leu Thr Trp Arg Ser Asp Val Leu Val Glu Tyr
                405                 410                 415

Gln Gly Glu Gly Arg Asn Val Thr Asp Pro Thr Cys Pro Ser Leu Ser
                420                 425                 430

Pro Gly Val Ser Gln Cys Phe Pro Asp Cys Val Cys Glu Asp Ala Tyr
                435                 440                 445

Asn Asn Thr Tyr Ala Cys Val Arg Thr Met Ser Ala Leu Trp Asn Leu
        450                 455                 460

Gln Tyr Cys Glu Phe Asp Asp Gln Glu Val Phe Val Glu Val Tyr Asn
465                 470                 475                 480

Leu Thr Ala Asp Pro Asp Gln Ile Thr Asn Ile Ala Lys Thr Ile Asp
                485                 490                 495

Pro Glu Leu Leu Gly Lys Met Asn Tyr Arg Leu Met Met Leu Gln Ser
                500                 505                 510

Cys Ser Gly Pro Thr Cys Arg Thr Pro Gly Val Phe Asp Pro Gly Tyr
            515                 520                 525

Arg Phe Asp Pro Arg Leu Met Phe Ser Asn Arg Gly Ser Val Arg Thr
        530                 535                 540

Arg Arg Phe Ser Lys His Leu Leu
545                 550

<210> SEQ ID NO 4
<211> LENGTH: 2647
<212> TYPE: PRT
<213> ORGANISM: Homo sapiens
```

<400> SEQUENCE: 4

```
Met Ser Ser Ser His Ser Arg Ala Gly Gln Ser Ala Ala Gly Ala Ala
1               5                   10                  15

Pro Gly Gly Gly Val Asp Thr Arg Asp Ala Glu Met Pro Ala Thr Glu
            20                  25                  30

Lys Asp Leu Ala Glu Asp Ala Pro Trp Lys Lys Ile Gln Gln Asn Thr
        35                  40                  45

Phe Thr Arg Trp Cys Asn Glu His Leu Lys Cys Val Ser Lys Arg Ile
    50                  55                  60

Ala Asn Leu Gln Thr Asp Leu Ser Asp Gly Leu Arg Leu Ile Ala Leu
65              70                  75                  80

Leu Glu Val Leu Ser Gln Lys Lys Met His Arg Lys His Asn Gln Arg
                85                  90                  95

Pro Thr Phe Arg Gln Met Gln Leu Glu Asn Val Ser Val Ala Leu Glu
            100                 105                 110

Phe Leu Asp Arg Glu Ser Ile Lys Leu Val Ser Ile Asp Ser Lys Ala
        115                 120                 125

Ile Val Asp Gly Asn Leu Lys Leu Ile Leu Gly Leu Ile Trp Thr Leu
    130                 135                 140

Ile Leu His Tyr Ser Ile Ser Met Pro Met Trp Asp Glu Glu Glu Asp
145             150                 155                 160

Glu Glu Ala Lys Lys Gln Thr Pro Lys Gln Arg Leu Leu Gly Trp Ile
                165                 170                 175

Gln Asn Lys Leu Pro Gln Leu Pro Ile Thr Asn Phe Ser Arg Asp Trp
            180                 185                 190

Gln Ser Gly Arg Ala Leu Gly Ala Leu Val Asp Ser Cys Ala Pro Gly
        195                 200                 205

Leu Cys Pro Asp Trp Asp Ser Trp Asp Ala Ser Lys Pro Val Thr Asn
    210                 215                 220

Ala Arg Glu Ala Met Gln Gln Ala Asp Asp Trp Leu Gly Ile Pro Gln
225             230                 235                 240

Val Ile Thr Pro Glu Glu Ile Val Asp Pro Asn Val Asp Glu His Ser
                245                 250                 255

Val Met Thr Tyr Leu Ser Gln Phe Pro Lys Ala Lys Leu Lys Pro Gly
            260                 265                 270

Ala Pro Leu Arg Pro Lys Leu Asn Pro Lys Lys Ala Arg Ala Tyr Gly
        275                 280                 285

Pro Gly Ile Glu Pro Thr Gly Asn Met Val Lys Lys Arg Ala Glu Phe
    290                 295                 300

Thr Val Glu Thr Arg Ser Ala Gly Gln Gly Glu Val Leu Val Tyr Val
305             310                 315                 320

Glu Asp Pro Ala Gly His Gln Glu Glu Ala Lys Val Thr Ala Asn Asn
                325                 330                 335

Asp Lys Asn Arg Thr Phe Ser Val Trp Tyr Val Pro Glu Val Thr Gly
            340                 345                 350

Thr His Lys Val Thr Val Leu Phe Ala Gly Gln His Ile Ala Lys Ser
        355                 360                 365

Pro Phe Glu Val Tyr Val Asp Lys Ser Gln Gly Asp Ala Ser Lys Val
    370                 375                 380

Thr Ala Gln Gly Pro Gly Leu Glu Pro Ser Gly Asn Ile Ala Asn Lys
385             390                 395                 400

Thr Thr Tyr Phe Glu Ile Phe Thr Ala Gly Ala Gly Thr Gly Glu Val
                405                 410                 415
```

```
Glu Val Val Ile Gln Asp Pro Met Gly Gln Lys Gly Thr Val Glu Pro
                420                 425                 430

Gln Leu Glu Ala Arg Gly Asp Ser Thr Tyr Arg Cys Ser Tyr Gln Pro
            435                 440                 445

Thr Met Glu Gly Val His Thr Val His Val Thr Phe Ala Gly Val Pro
        450                 455                 460

Ile Pro Arg Ser Pro Tyr Thr Val Thr Val Gly Gln Ala Cys Asn Pro
465                 470                 475                 480

Ser Ala Cys Arg Ala Val Gly Arg Gly Leu Gln Pro Lys Gly Val Arg
                485                 490                 495

Val Lys Glu Thr Ala Asp Phe Lys Val Tyr Thr Lys Gly Ala Gly Ser
            500                 505                 510

Gly Glu Leu Lys Val Thr Val Lys Gly Pro Lys Gly Glu Glu Arg Val
        515                 520                 525

Lys Gln Lys Asp Leu Gly Asp Gly Val Tyr Gly Phe Glu Tyr Tyr Pro
    530                 535                 540

Met Val Pro Gly Thr Tyr Ile Val Thr Ile Thr Trp Gly Gly Gln Asn
545                 550                 555                 560

Ile Gly Arg Ser Pro Phe Glu Val Lys Val Gly Thr Glu Cys Gly Asn
                565                 570                 575

Gln Lys Val Arg Ala Trp Gly Pro Gly Leu Glu Gly Gly Val Val Gly
            580                 585                 590

Lys Ser Ala Asp Phe Val Val Glu Ala Ile Gly Asp Asp Val Gly Thr
        595                 600                 605

Leu Gly Phe Ser Val Glu Gly Pro Ser Gln Ala Lys Ile Glu Cys Asp
    610                 615                 620

Asp Lys Gly Asp Gly Ser Cys Asp Val Arg Tyr Trp Pro Gln Glu Ala
625                 630                 635                 640

Gly Glu Tyr Ala Val His Val Leu Cys Asn Ser Glu Asp Ile Arg Leu
                645                 650                 655

Ser Pro Phe Met Ala Asp Ile Arg Asp Ala Pro Gln Asp Phe His Pro
            660                 665                 670

Asp Arg Val Lys Ala Arg Gly Pro Gly Leu Glu Lys Thr Gly Val Ala
        675                 680                 685

Val Asn Lys Pro Ala Glu Phe Thr Val Asp Ala Lys His Gly Gly Lys
    690                 695                 700

Ala Pro Leu Arg Val Gln Val Gln Asp Asn Glu Gly Cys Pro Val Glu
705                 710                 715                 720

Ala Leu Val Lys Asp Asn Gly Asn Gly Thr Tyr Ser Cys Ser Tyr Val
                725                 730                 735

Pro Arg Lys Pro Val Lys His Thr Ala Met Val Ser Trp Gly Gly Val
            740                 745                 750

Ser Ile Pro Asn Ser Pro Phe Arg Val Asn Val Gly Ala Gly Ser His
        755                 760                 765

Pro Asn Lys Val Lys Val Tyr Gly Pro Gly Val Ala Lys Thr Gly Leu
    770                 775                 780

Lys Ala His Glu Pro Thr Tyr Phe Thr Val Asp Cys Ala Glu Ala Gly
785                 790                 795                 800

Gln Gly Asp Val Ser Ile Gly Ile Lys Cys Ala Pro Gly Val Val Gly
                805                 810                 815

Pro Ala Glu Ala Asp Ile Asp Phe Asp Ile Ile Arg Asn Asp Asn Asp
            820                 825                 830
```

```
Thr Phe Thr Val Lys Tyr Thr Pro Arg Gly Ala Gly Ser Tyr Thr Ile
            835                 840                 845

Met Val Leu Phe Ala Asp Gln Ala Thr Pro Thr Ser Pro Ile Arg Val
    850                 855                 860

Lys Val Glu Pro Ser His Asp Ala Ser Lys Val Lys Ala Glu Gly Pro
865                 870                 875                 880

Gly Leu Ser Arg Thr Gly Val Glu Leu Gly Lys Pro Thr His Phe Thr
                885                 890                 895

Val Asn Ala Lys Ala Ala Gly Lys Gly Lys Leu Asp Val Gln Phe Ser
        900                 905                 910

Gly Leu Thr Lys Gly Asp Ala Val Arg Asp Val Asp Ile Ile Asp His
            915                 920                 925

His Asp Asn Thr Tyr Thr Val Lys Tyr Thr Pro Val Gln Gln Gly Pro
    930                 935                 940

Val Gly Val Asn Val Thr Tyr Gly Gly Asp Pro Ile Pro Lys Ser Pro
945                 950                 955                 960

Phe Ser Val Ala Val Ser Pro Ser Leu Asp Leu Ser Lys Ile Lys Val
                965                 970                 975

Ser Gly Leu Gly Glu Lys Val Asp Val Gly Lys Asp Gln Glu Phe Thr
        980                 985                 990

Val Lys Ser Lys Gly Ala Gly Gly Gln Gly Lys Val Ala Ser Lys Ile
            995                 1000                1005

Val Gly Pro Ser Gly Ala Ala Val Pro Cys Lys Val Glu Pro Gly
    1010                1015                1020

Leu Gly Ala Asp Asn Ser Val Val Arg Phe Leu Pro Arg Glu Glu
    1025                1030                1035

Gly Pro Tyr Glu Val Glu Val Thr Tyr Asp Gly Val Pro Val Pro
    1040                1045                1050

Gly Ser Pro Phe Pro Leu Glu Ala Val Ala Pro Thr Lys Pro Ser
    1055                1060                1065

Lys Val Lys Ala Phe Gly Pro Gly Leu Gln Gly Gly Ser Ala Gly
    1070                1075                1080

Ser Pro Ala Arg Phe Thr Ile Asp Thr Lys Gly Ala Gly Thr Gly
    1085                1090                1095

Gly Leu Gly Leu Thr Val Glu Gly Pro Cys Glu Ala Gln Leu Glu
    1100                1105                1110

Cys Leu Asp Asn Gly Asp Gly Thr Cys Ser Val Ser Tyr Val Pro
    1115                1120                1125

Thr Glu Pro Gly Asp Tyr Asn Ile Asn Ile Leu Phe Ala Asp Thr
    1130                1135                1140

His Ile Pro Gly Ser Pro Phe Lys Ala His Val Val Pro Cys Phe
    1145                1150                1155

Asp Ala Ser Lys Val Lys Cys Ser Gly Pro Gly Leu Glu Arg Ala
    1160                1165                1170

Thr Ala Gly Glu Val Gly Gln Phe Gln Val Asp Cys Ser Ser Ala
    1175                1180                1185

Gly Ser Ala Glu Leu Thr Ile Glu Ile Cys Ser Glu Ala Gly Leu
    1190                1195                1200

Pro Ala Glu Val Tyr Ile Gln Asp His Gly Asp Gly Thr His Thr
    1205                1210                1215

Ile Thr Tyr Ile Pro Leu Cys Pro Gly Ala Tyr Thr Val Thr Ile
    1220                1225                1230

Lys Tyr Gly Gly Gln Pro Val Pro Asn Phe Pro Ser Lys Leu Gln
```

```
                1235                 1240                 1245
Val Glu Pro Ala Val Asp Thr Ser Gly Val Gln Cys Tyr Gly Pro
    1250                 1255                 1260
Gly Ile Glu Gly Gln Gly Val Phe Arg Glu Ala Thr Thr Glu Phe
    1265                 1270                 1275
Ser Val Asp Ala Arg Ala Leu Thr Gln Thr Gly Gly Pro His Val
    1280                 1285                 1290
Lys Ala Arg Val Ala Asn Pro Ser Gly Asn Leu Thr Glu Thr Tyr
    1295                 1300                 1305
Val Gln Asp Arg Gly Asp Gly Met Tyr Lys Val Glu Tyr Thr Pro
    1310                 1315                 1320
Tyr Glu Glu Gly Leu His Ser Val Asp Val Thr Tyr Asp Gly Ser
    1325                 1330                 1335
Pro Val Pro Ser Ser Pro Phe Gln Val Pro Val Thr Glu Gly Cys
    1340                 1345                 1350
Asp Pro Ser Arg Val Arg Val His Gly Pro Gly Ile Gln Ser Gly
    1355                 1360                 1365
Thr Thr Asn Lys Pro Asn Lys Phe Thr Val Glu Thr Arg Gly Ala
    1370                 1375                 1380
Gly Thr Gly Gly Leu Gly Leu Ala Val Glu Gly Pro Ser Glu Ala
    1385                 1390                 1395
Lys Met Ser Cys Met Asp Asn Lys Asp Gly Ser Cys Ser Val Glu
    1400                 1405                 1410
Tyr Ile Pro Tyr Glu Ala Gly Thr Tyr Ser Leu Asn Val Thr Tyr
    1415                 1420                 1425
Gly Gly His Gln Val Pro Gly Ser Pro Phe Lys Val Pro Val His
    1430                 1435                 1440
Asp Val Thr Asp Ala Ser Lys Val Lys Cys Ser Gly Pro Gly Leu
    1445                 1450                 1455
Ser Pro Gly Met Val Arg Ala Asn Leu Pro Gln Ser Phe Gln Val
    1460                 1465                 1470
Asp Thr Ser Lys Ala Gly Val Ala Pro Leu Gln Val Lys Val Gln
    1475                 1480                 1485
Gly Pro Lys Gly Leu Val Glu Pro Val Asp Val Asp Asn Ala
    1490                 1495                 1500
Asp Gly Thr Gln Thr Val Asn Tyr Val Pro Ser Arg Glu Gly Pro
    1505                 1510                 1515
Tyr Ser Ile Ser Val Leu Tyr Gly Asp Glu Glu Val Pro Arg Ser
    1520                 1525                 1530
Pro Phe Lys Val Lys Val Leu Pro Thr His Asp Ala Ser Lys Val
    1535                 1540                 1545
Lys Ala Ser Gly Pro Gly Leu Asn Thr Thr Gly Val Pro Ala Ser
    1550                 1555                 1560
Leu Pro Val Glu Phe Thr Ile Asp Ala Lys Asp Ala Gly Glu Gly
    1565                 1570                 1575
Leu Leu Ala Val Gln Ile Thr Asp Pro Glu Gly Lys Pro Lys Lys
    1580                 1585                 1590
Thr His Ile Gln Asp Asn His Asp Gly Thr Tyr Thr Val Ala Tyr
    1595                 1600                 1605
Val Pro Asp Val Thr Gly Arg Tyr Thr Ile Leu Ile Lys Tyr Gly
    1610                 1615                 1620
Gly Asp Glu Ile Pro Phe Ser Pro Tyr Arg Val Arg Ala Val Pro
    1625                 1630                 1635
```

```
Thr Gly Asp Ala Ser Lys Cys Thr Val Thr Val Ser Ile Gly Gly
    1640                1645                1650

His Gly Leu Gly Ala Gly Ile Gly Pro Thr Ile Gln Ile Gly Glu
    1655                1660                1665

Glu Thr Val Ile Thr Val Asp Thr Lys Ala Ala Gly Lys Gly Lys
    1670                1675                1680

Val Thr Cys Thr Val Cys Thr Pro Asp Gly Ser Glu Val Asp Val
    1685                1690                1695

Asp Val Val Glu Asn Glu Asp Gly Thr Phe Asp Ile Phe Tyr Thr
    1700                1705                1710

Ala Pro Gln Pro Gly Lys Tyr Val Ile Cys Val Arg Phe Gly Gly
    1715                1720                1725

Glu His Val Pro Asn Ser Pro Phe Gln Val Thr Ala Leu Ala Gly
    1730                1735                1740

Asp Gln Pro Ser Val Gln Pro Pro Leu Arg Ser Gln Gln Leu Ala
    1745                1750                1755

Pro Gln Tyr Thr Tyr Ala Gln Gly Gly Gln Gln Thr Trp Ala Pro
    1760                1765                1770

Glu Arg Pro Leu Val Gly Val Asn Gly Leu Asp Val Thr Ser Leu
    1775                1780                1785

Arg Pro Phe Asp Leu Val Ile Pro Phe Thr Ile Lys Lys Gly Glu
    1790                1795                1800

Ile Thr Gly Glu Val Arg Met Pro Ser Gly Lys Val Ala Gln Pro
    1805                1810                1815

Thr Ile Thr Asp Asn Lys Asp Gly Thr Val Thr Val Arg Tyr Ala
    1820                1825                1830

Pro Ser Glu Ala Gly Leu His Glu Met Asp Ile Arg Tyr Asp Asn
    1835                1840                1845

Met His Ile Pro Gly Ser Pro Leu Gln Phe Tyr Val Asp Tyr Val
    1850                1855                1860

Asn Cys Gly His Val Thr Ala Tyr Gly Pro Gly Leu Thr His Gly
    1865                1870                1875

Val Val Asn Lys Pro Ala Thr Phe Thr Val Asn Thr Lys Asp Ala
    1880                1885                1890

Gly Glu Gly Gly Leu Ser Leu Ala Ile Glu Gly Pro Ser Lys Ala
    1895                1900                1905

Glu Ile Ser Cys Thr Asp Asn Gln Asp Gly Thr Cys Ser Val Ser
    1910                1915                1920

Tyr Leu Pro Val Leu Pro Gly Asp Tyr Ser Ile Leu Val Lys Tyr
    1925                1930                1935

Asn Glu Gln His Val Pro Gly Ser Pro Phe Thr Ala Arg Val Thr
    1940                1945                1950

Gly Asp Asp Ser Met Arg Met Ser His Leu Lys Val Gly Ser Ala
    1955                1960                1965

Ala Asp Ile Pro Ile Asn Ile Ser Glu Thr Asp Leu Ser Leu Leu
    1970                1975                1980

Thr Ala Thr Val Val Pro Pro Ser Gly Arg Glu Glu Pro Cys Leu
    1985                1990                1995

Leu Lys Arg Leu Arg Asn Gly His Val Gly Ile Ser Phe Val Pro
    2000                2005                2010

Lys Glu Thr Gly Glu His Leu Val His Val Lys Lys Asn Gly Gln
    2015                2020                2025
```

```
His Val Ala Ser Ser Pro Ile Pro Val Val Ile Ser Gln Ser Glu
2030                2035                2040

Ile Gly Asp Ala Ser Arg Val Arg Val Ser Gly Gln Gly Leu His
2045                2050                2055

Glu Gly His Thr Phe Glu Pro Ala Glu Phe Ile Ile Asp Thr Arg
2060                2065                2070

Asp Ala Gly Tyr Gly Gly Leu Ser Leu Ser Ile Glu Gly Pro Ser
2075                2080                2085

Lys Val Asp Ile Asn Thr Glu Asp Leu Glu Asp Gly Thr Cys Arg
2090                2095                2100

Val Thr Tyr Cys Pro Thr Glu Pro Gly Asn Tyr Ile Ile Asn Ile
2105                2110                2115

Lys Phe Ala Asp Gln His Val Pro Gly Ser Pro Phe Ser Val Lys
2120                2125                2130

Val Thr Gly Glu Gly Arg Val Lys Glu Ser Ile Thr Arg Arg Arg
2135                2140                2145

Arg Ala Pro Ser Val Ala Asn Val Gly Ser His Cys Asp Leu Ser
2150                2155                2160

Leu Lys Ile Pro Glu Ile Ser Ile Gln Asp Met Thr Ala Gln Val
2165                2170                2175

Thr Ser Pro Ser Gly Lys Thr His Glu Ala Glu Ile Val Glu Gly
2180                2185                2190

Glu Asn His Thr Tyr Cys Ile Arg Phe Val Pro Ala Glu Met Gly
2195                2200                2205

Thr His Thr Val Ser Val Lys Tyr Lys Gly Gln His Val Pro Gly
2210                2215                2220

Ser Pro Phe Gln Phe Thr Val Gly Pro Leu Gly Glu Gly Gly Ala
2225                2230                2235

His Lys Val Arg Ala Gly Gly Pro Gly Leu Glu Arg Ala Glu Ala
2240                2245                2250

Gly Val Pro Ala Glu Phe Ser Ile Trp Thr Arg Glu Ala Gly Ala
2255                2260                2265

Gly Gly Leu Ala Ile Ala Val Glu Gly Pro Ser Lys Ala Glu Ile
2270                2275                2280

Ser Phe Glu Asp Arg Lys Asp Gly Ser Cys Gly Val Ala Tyr Val
2285                2290                2295

Val Gln Glu Pro Gly Asp Tyr Glu Val Ser Val Lys Phe Asn Glu
2300                2305                2310

Glu His Ile Pro Asp Ser Pro Phe Val Val Pro Val Ala Ser Pro
2315                2320                2325

Ser Gly Asp Ala Arg Arg Leu Thr Val Ser Ser Leu Gln Glu Ser
2330                2335                2340

Gly Leu Lys Val Asn Gln Pro Ala Ser Phe Ala Val Ser Leu Asn
2345                2350                2355

Gly Ala Lys Gly Ala Ile Asp Ala Lys Val His Ser Pro Ser Gly
2360                2365                2370

Ala Leu Glu Glu Cys Tyr Val Thr Glu Ile Asp Gln Asp Lys Tyr
2375                2380                2385

Ala Val Arg Phe Ile Pro Arg Glu Asn Gly Val Tyr Leu Ile Asp
2390                2395                2400

Val Lys Phe Asn Gly Thr His Ile Pro Gly Ser Pro Phe Lys Ile
2405                2410                2415

Arg Val Gly Glu Pro Gly His Gly Gly Asp Pro Gly Leu Val Ser
```

```
            2420                2425                2430

Ala Tyr Gly Ala Gly Leu Glu Gly Gly Val Thr Gly Asn Pro Ala
    2435                2440                2445

Glu Phe Val Val Asn Thr Ser Asn Ala Gly Ala Gly Ala Leu Ser
    2450                2455                2460

Val Thr Ile Asp Gly Pro Ser Lys Val Lys Met Asp Cys Gln Glu
    2465                2470                2475

Cys Pro Glu Gly Tyr Arg Val Thr Tyr Thr Pro Met Ala Pro Gly
    2480                2485                2490

Ser Tyr Leu Ile Ser Ile Lys Tyr Gly Gly Pro Tyr His Ile Gly
    2495                2500                2505

Gly Ser Pro Phe Lys Ala Lys Val Thr Gly Pro Arg Leu Val Ser
    2510                2515                2520

Asn His Ser Leu His Glu Thr Ser Ser Val Phe Val Asp Ser Leu
    2525                2530                2535

Thr Lys Ala Thr Cys Ala Pro Gln His Gly Ala Pro Gly Pro Gly
    2540                2545                2550

Pro Ala Asp Ala Ser Lys Val Val Ala Lys Gly Leu Gly Leu Ser
    2555                2560                2565

Lys Ala Tyr Val Gly Gln Lys Ser Ser Phe Thr Val Asp Cys Ser
    2570                2575                2580

Lys Ala Gly Asn Asn Met Leu Leu Val Gly Val His Gly Pro Arg
    2585                2590                2595

Thr Pro Cys Glu Glu Ile Leu Val Lys His Val Gly Ser Arg Leu
    2600                2605                2610

Tyr Ser Val Ser Tyr Leu Leu Lys Asp Lys Gly Glu Tyr Thr Leu
    2615                2620                2625

Val Val Lys Trp Gly Asp Glu His Ile Pro Gly Ser Pro Tyr Arg
    2630                2635                2640

Val Val Val Pro
    2645

<210> SEQ ID NO 5
<211> LENGTH: 18
<212> TYPE: PRT
<213> ORGANISM: Homo sapiens

<400> SEQUENCE: 5

Val Asn Asp Thr Gln Phe Val Arg Phe Asp Ser Asp Ala Ala Ser Pro
1               5                   10                  15

Arg Gly

<210> SEQ ID NO 6
<211> LENGTH: 16
<212> TYPE: PRT
<213> ORGANISM: Homo sapiens

<400> SEQUENCE: 6

Leu Gly Arg Phe Glu Arg Met Leu Ala Ala Gln Gly Val Asp Pro Gly
1               5                   10                  15

<210> SEQ ID NO 7
<211> LENGTH: 15
<212> TYPE: PRT
<213> ORGANISM: Homo sapiens

<400> SEQUENCE: 7
```

```
Ile Glu Gly Asn Leu Ile Phe Asp Pro Asn Asn Tyr Leu Pro Lys
1               5                   10                  15

<210> SEQ ID NO 8
<211> LENGTH: 15
<212> TYPE: PRT
<213> ORGANISM: Homo sapiens

<400> SEQUENCE: 8

Gly Thr Asn Leu Phe Leu Val Ala Ala His Glu Leu Gly His Ser
1               5                   10                  15

<210> SEQ ID NO 9
<211> LENGTH: 15
<212> TYPE: PRT
<213> ORGANISM: Homo sapiens

<400> SEQUENCE: 9

Asp Lys Val Leu Ile Arg Ile Met Val Ser Arg Ser Glu Val Asp
1               5                   10                  15

<210> SEQ ID NO 10
<211> LENGTH: 11
<212> TYPE: PRT
<213> ORGANISM: Homo sapiens

<400> SEQUENCE: 10

Asp His Leu Lys Tyr Val Met Leu Pro Val Ala
1               5                   10

<210> SEQ ID NO 11
<211> LENGTH: 12
<212> TYPE: PRT
<213> ORGANISM: Homo sapiens

<400> SEQUENCE: 11

Asp His Leu Lys Tyr Val Met Leu Pro Val Ala Asp
1               5                   10

<210> SEQ ID NO 12
<211> LENGTH: 13
<212> TYPE: PRT
<213> ORGANISM: Homo sapiens

<400> SEQUENCE: 12

Asp His Leu Lys Tyr Val Met Leu Pro Val Ala Asp Gln
1               5                   10

<210> SEQ ID NO 13
<211> LENGTH: 11
<212> TYPE: PRT
<213> ORGANISM: Homo sapiens

<400> SEQUENCE: 13

Asp His Leu Lys Tyr Val Met Leu Pro Val Ala
1               5                   10

<210> SEQ ID NO 14
<211> LENGTH: 12
<212> TYPE: PRT
<213> ORGANISM: Homo sapiens

<400> SEQUENCE: 14

Asp His Leu Lys Tyr Val Met Leu Pro Val Ala Asp
1               5                   10
```

```
<210> SEQ ID NO 15
<211> LENGTH: 13
<212> TYPE: PRT
<213> ORGANISM: Homo sapiens

<400> SEQUENCE: 15

Asp His Leu Lys Tyr Val Met Leu Pro Val Ala Asp Gln
1               5                   10

<210> SEQ ID NO 16
<211> LENGTH: 5
<212> TYPE: PRT
<213> ORGANISM: Homo sapiens
<220> FEATURE:
<221> NAME/KEY: MOD_RES
<222> LOCATION: (2)..(2)
<223> OTHER INFORMATION: Lys or Arg

<400> SEQUENCE: 16

Gln Xaa Arg Ala Ala
1               5
```